United States Patent
Fan et al.

(10) Patent No.: US 11,111,432 B2
(45) Date of Patent: Sep. 7, 2021

(54) TRIANGULAR CARBON QUANTUM DOTS AND COMPOSITIONS AND USES THEREOF

(71) Applicant: BEIJING NORMAL UNIVERSITY, Beijing (CN)

(72) Inventors: Louzhen Fan, Beijing (CN); Fanglong Yuan, Beijing (CN); Shihe Yang, Beijing (CN); Zifan Xi, Beijing (CN)

(73) Assignee: BEIJING NORMAL UNIVERSITY, Beijing (CN)

( * ) Notice: Subject to any disclaimer, the term of this patent is extended or adjusted under 35 U.S.C. 154(b) by 0 days.

(21) Appl. No.: 15/749,763

(22) PCT Filed: Jan. 2, 2018

(86) PCT No.: PCT/CN2018/070022
§ 371 (c)(1),
(2) Date: Feb. 1, 2018

(87) PCT Pub. No.: WO2019/134068
PCT Pub. Date: Jul. 11, 2019

(65) Prior Publication Data
US 2020/0354630 A1    Nov. 12, 2020

(51) Int. Cl.
*C09K 11/65* (2006.01)
*H01L 33/20* (2010.01)
*B82Y 15/00* (2011.01)
*B82Y 20/00* (2011.01)
*B82Y 30/00* (2011.01)
*B82Y 40/00* (2011.01)
*H01L 33/26* (2010.01)
*H01L 51/50* (2006.01)

(52) U.S. Cl.
CPC .............. *C09K 11/65* (2013.01); *H01L 33/20* (2013.01); *B82Y 15/00* (2013.01); *B82Y 20/00* (2013.01); *B82Y 30/00* (2013.01); *B82Y 40/00* (2013.01); *H01L 33/26* (2013.01); *H01L 51/502* (2013.01)

(58) Field of Classification Search
CPC ....... C09K 11/65; H01L 33/20; H01L 51/502; B82Y 15/00; B82Y 20/00; B82Y 30/00; B82Y 40/00
USPC .............................. 549/453; 257/40; 438/99
See application file for complete search history.

(56) References Cited

U.S. PATENT DOCUMENTS

| | | | |
|---|---|---|---|
| 4,771,689 A | 9/1988 | Arzoumanian et al. | |
| 8,735,175 B2 | 5/2014 | Geddes | |
| 2012/0074393 A1* | 3/2012 | Wurthner et al. | C07D 519/00 548/453 |

FOREIGN PATENT DOCUMENTS

| | | |
|---|---|---|
| CN | 103274388 A | 9/2013 |
| CN | 104046353 A | 9/2014 |
| CN | 105012962 A | 11/2015 |

(Continued)

OTHER PUBLICATIONS

International Search Report for international patent application PCT/CN2018/070022, dated Sep. 25, 2018, 3 pages.

(Continued)

*Primary Examiner* — Thinh T Nguyen
(74) *Attorney, Agent, or Firm* — Rimon, P.C.

(57) ABSTRACT

Provided herein are triangular carbon quantum dots with narrow bandwidth emission, methods of making them, and methods of using such triangular carbon quantum dots, such as in multicolored LED displays.

29 Claims, 38 Drawing Sheets

(56) References Cited

FOREIGN PATENT DOCUMENTS

CN 106978168 A 7/2017
WO 02059414 A3 2/2003

OTHER PUBLICATIONS

Written Opinion of the International Searching Authority for international patent application PCT/CN2018/070022, dated Sep. 25, 2018, 3 pages.
International Preliminary Report on Patentability for PCT/CN2018/070022, dated Jul. 7, 2020, 4 pages.

* cited by examiner

TRIANGULAR CARBON QUANTUM DOTS AND COMPOSITIONS AND USES THEREOF

CROSS-REFERENCE TO RELATED APPLICATION

This application is a U.S. National Phase Application of International Patent Application No. PCT/CN2018/070022 having an international filing date of Jan. 2, 2018, the disclosure of which is herein incorporated by reference in its entirety for all purposes.

TECHNICAL FIELD

Provided herein are triangular carbon quantum dots (T-CQDs) with narrow bandwidth emission, methods of making them, and methods of using such triangular carbon quantum dots, such as in multicolored LED displays.

BACKGROUND

Getting light from carbon has long been a dream of the scientific community. Carbon-based highly efficient light-emitting materials will not only raise the prospect of the next-generation technological frontiers of carbon photonics and optoelectronics, but also offer an alternative to traditional semiconductor inorganic quantum dots (QDs) such as the $Cd^{2+}/Pb^{2+}$-based QDs in light-emitting applications taking advantage of carbon's high stability, low cost, high abundance and environment-friendliness[1-7]. The discovery of room temperature light emission from quantum sized carbon (<10 nm) in 2006[8] triggered intensive researches on light-emitting carbon quantum dots (CQDs) to realize their wide potential applications[9-14]. In the last few years, great progress has been made in designing and synthesizing highly tunable bandgap fluorescent CQDs with a quantum yield (QY) as high as 75%, even comparable to the best performing $Cd^{2+}/Pb^{2+}$-based QDs, through a variety of strategies such as heteroatom doping, surface engineering or passivation, and product separation and purification[15-18]. Meanwhile, the wide potential optoelectronic applications of the CQDs have also been demonstrated[17-23]. For instance, light-emitting diodes (LEDs) from blue to red based on the bandgap fluorescent CQDs have been reported most recently[18], laying a solid foundation for the development of a new display technology based on the CQDs. However, such CQDs are widely known for emitting light with poor color-purity with a broad bandwidth (full width at half maximum (FWHM)>80 nm),[15-19,23] inferior to the narrow bandwidth emission of $Cd^{2+}/Pb^{2+}$-based QDs (FWHM<40 nm), which severely hinders the application of CQDs-based LEDs in high color-purity displays[24,25].

The exact mechanism of the broadband fluorescence spectra of CQDs has been a longstanding unsettled issue. It has been generally believed that the broadband fluorescence spectra of CQDs stem from a broad size distribution. However, even after narrowing the size distribution through elaborate separation and purification, the fluorescence spectra still remains broad (FWHM>80 nm)[15-19,26]. This indicates that the broadband fluorescence spectra cannot be simply ascribed to the dot size polydispersity, but may be intrinsic to the CQDs. For instance, the complex nonradiative excited-state relaxation processes arising from specific structure-associated phenomena, such as self-localized charges and surface defect trapped carriers observed in traditional inorganic QDs, are probably the main origin of the broadband fluorescence spectra of CQDs[1-3]. The former can be considered as transient defects formed in the excited states where photogenerated charge carriers are stabilized through large-amplitude vibrations and distortions driven by strong electron-phonon coupling[27-29], while the latter is usually induced by the numerous electron-withdrawing oxygen-containing groups such as carboxyl, carbonyl and epoxy groups at edge or basal plane sites of the $CQDs^{26,30-33}$. Consequently, weakening the electron-phonon coupling and reducing the surface defects by structural engineering may be a feasible way to realize narrow bandwidth emission of CQDs with high color-purity.

SUMMARY

Provided in some aspects, the present disclosure describes a triangular carbon quantum dot containing a conjugated triangular structure that includes at least four aromatic rings. In some embodiments, the conjugated triangular structure includes a side functional group. In some embodiments, the content of carbon atoms in the triangular carbon quantum dot is 50 weight % or more.

In some embodiments of the triangular carbon quantum dots described herein, the conjugated triangular structure contains a 6-member aromatic core ring fused to at least three aromatic rings, 6 ring atoms of the core ring being two ring atoms of each of the at least three aromatic rings. In some embodiments of any of the triangular carbon quantum dots described herein, the conjugated triangular structure contains a single 6-member aromatic core ring fused to the at least three aromatic rings. In some embodiments of any of the triangular carbon quantum dots described herein, the conjugated triangular structure contains a plurality of the 6-member aromatic core rings fused to the at least three aromatic rings. In some embodiments of any of the triangular carbon quantum dots described herein, the conjugated triangular structure contains at least 4, 10, 19 or 34 or more 6-member aromatic core rings fused to the at least three aromatic rings. In some embodiments of any of the triangular carbon quantum dots described herein, each of the at least three aromatic rings fused to the core ring is a 6-member aromatic ring.

In some embodiments of any of the triangular carbon quantum dots described herein, the core ring is formed by conjugation of at least three aromatic ring precursors. In some embodiments, at least one of the aromatic ring precursors is a substituted benzene. In other embodiments, each of the at least three aromatic ring precursors is a substituted benzene.

In some embodiments of any of the triangular carbon quantum dots described herein, at least one of the three aromatic ring precursors is selected from the group consisting of benzene-1,3,5-triol (phloroglucinol), resorcinol, 5-aminobenzene-1,3-diol, 5-(dimethylamino)benzene-1,3-diol, 5-(diethylamino)benzene-1,3-diol, 5-(dipropylamino)benzene-1,3-diol, 5-(methylthio)benzene-1,3-diol, 5-methoxybenzene-1,3-diol, 3,5-dihydroxyphenylboronic acid, pyridine-3,5-diol, phosphinine-3,5-diol, and borinine-3,5-diol.

In some embodiments of any of the triangular carbon quantum dots described herein, at least one of the aromatic ring precursors contains a hetero aromatic ring. In some embodiments, the hetero aromatic ring contains one or more heteroatoms selected from the group consisting of N, P, and B.

In some embodiments of any of the triangular carbon quantum dots described herein, the at least three aromatic rings contain the same aromatic ring. In other embodiments, the at least three aromatic rings contain different aromatic rings.

In some embodiments, the triangular carbon quantum dots described herein are prepared by solvothermal synthesis using at least three precursor molecules each containing an aromatic ring. In some embodiments, each of the precursor molecules contains a 6-member aromatic ring.

In some embodiments of any of the triangular carbon quantum dots described herein, each of the precursor molecules is a compound having a structure of Formula A:

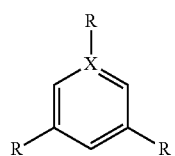

(A)

wherein X is selected from the group consisting of C, N, P, and B; and each R is independently selected from the group consisting of —OR$^a$, —NR$^b$R$^c$, —SR$^d$, —COOR$^e$, and —B(OR$^f$)(OR$^g$), wherein R$^a$, R$^b$, R$^c$, R$^d$, R$^e$, R$^f$ and R$^g$ are each independently H or C$_{1-6}$alkyl, or R may be absent. In some embodiments, each R is independently selected from the group consisting of hydroxy, amino, dimethylamino, diethylamino, dipropylamino, methylthio, methoxy, and —B(OH)$_2$, or R may be absent. In some embodiments, each of the precursor molecules is selected from the group consisting of

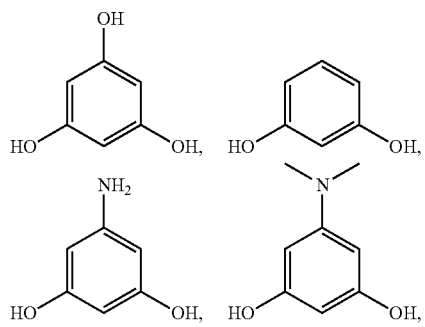

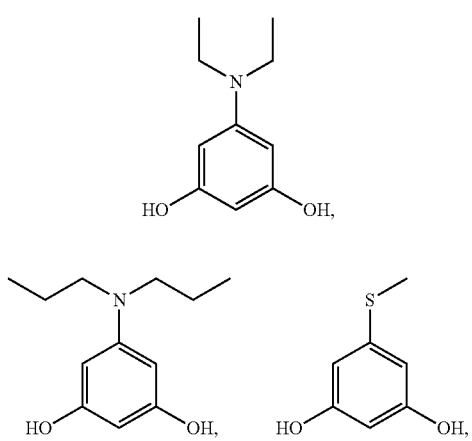

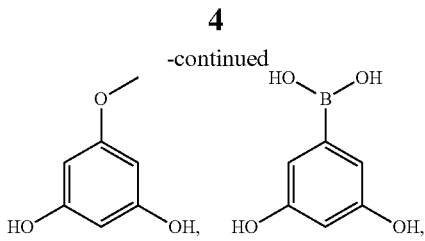

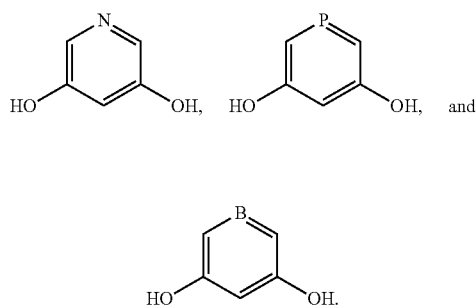

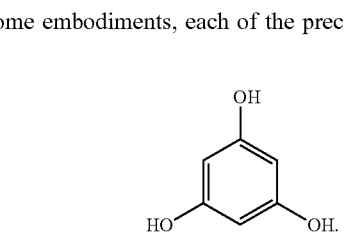

In some embodiments, each of the precursor molecules is

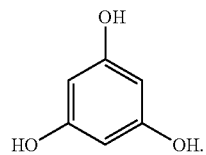

In some embodiments of any of the triangular carbon quantum dots described herein, the precursor molecules are used to form a conjugated triangular structure containing a structure of Formula I:

(I)

wherein
each R is independently selected from the group consisting of —OR$^a$, —NR$^b$R$^c$, —SR$^d$, COOR$^e$, and —B(OR$^f$)(OR$^g$), wherein R$^a$, R$^b$, R$^c$, R$^d$, R$^e$, R$^f$ and R$^g$ are each independently H or C$_{1-6}$alkyl; and/or
the structure of Formula I serves as a core structure for further conjugation with the precursor molecules to form a larger conjugated triangular structure.

In some embodiments of any of the triangular carbon quantum dots described herein, the precursor molecules are used to form a conjugated triangular structure containing a structure of Formula I-A:

(I-A)

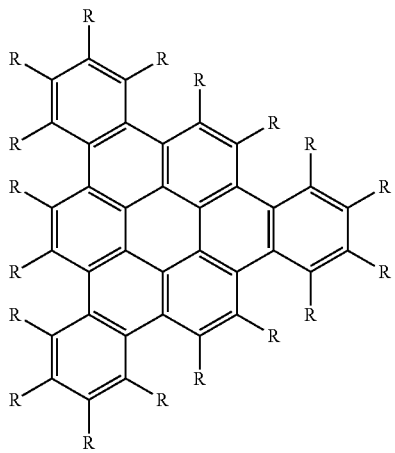

wherein
each R is independently selected from the group consisting of —OR$^a$, —NR$^b$R$^c$, —SR$^d$, COOR$^e$, and —B(OR$^f$)(OR$^g$), wherein R$^a$, R$^b$, R$^c$, R$^d$, R$^e$, R$^f$ and R$^g$ are each independently H or C$_{1-6}$alkyl; and/or
the structure of Formula I-A serves as a core structure for further conjugation with the precursor molecules to form a larger conjugated triangular structure.

In some embodiments of any of the triangular carbon quantum dots described herein, the precursor molecules are used to form a conjugated triangular structure containing a structure of Formula I-B:

(I-B)

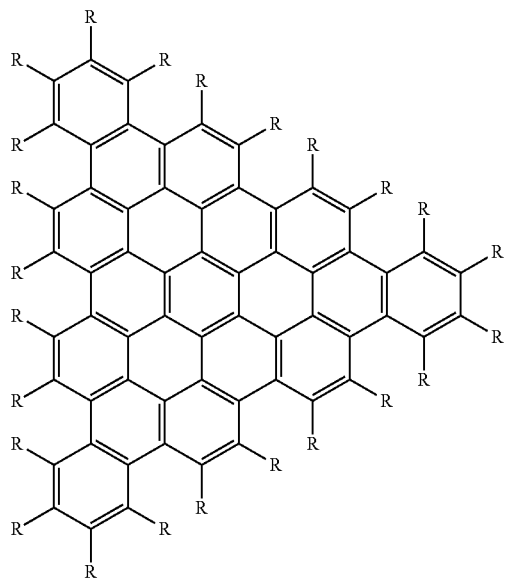

wherein
each R is independently selected from the group consisting of —OR$^a$, —NR$^b$R$^c$, —SR$^d$, COOR$^e$, and —B(OR$^f$)(OR$^g$), wherein R$^a$, R$^b$, R$^c$, R$^d$, R$^e$, R$^f$ and R$^g$ are each independently H or C$_{1-6}$alkyl; and/or
the structure of Formula I-B serves as a core structure for further conjugation with the precursor molecules to form a larger conjugated triangular structure.

In some embodiments of any of the triangular carbon quantum dots described herein, the precursor molecules are used to form a conjugated triangular structure comprising a structure of Formula II:

(II)

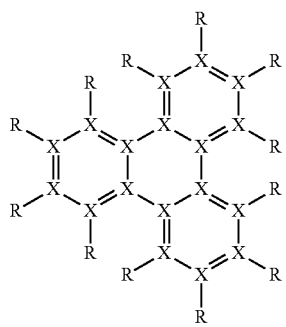

wherein
each X is independently selected from the group consisting of C, N, P, and B;
each R is independently selected from the group consisting of —OR$^a$, —NR$^b$R$^c$, —SR$^d$, COOR$^e$, and —B(OR$^f$)(OR$^g$), wherein R$^a$, R$^b$, R$^c$, R$^d$, R$^e$, R$^f$ and R$^g$ are each independently H or C$_{1-6}$alkyl, or R is absent; and/or
the structure of Formula II serves as a core structure for further conjugation with the precursor molecules to form a larger conjugated triangular structure.

In some embodiments of any of the triangular carbon quantum dots described herein, the precursor molecules are used to form a conjugated triangular structure comprising a structure of Formula II-A:

(II-A)

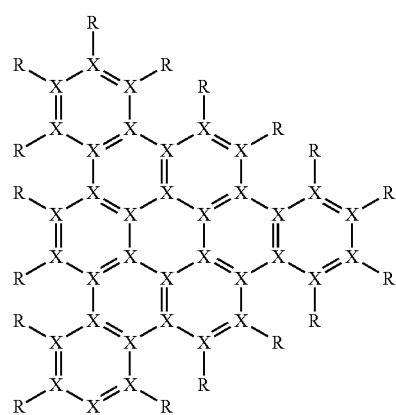

wherein
each X is independently selected from the group consisting of C, N, P, and B;
each R is independently selected from the group consisting of —OR$^a$, —NR$^b$R$^c$, —SR$^d$, COOR$^e$, and —B(OR$^f$)(OR$^g$), wherein R$^a$, R$^b$, R$^c$, R$^d$, R$^e$, R$^f$ and R$^g$ are each independently H or C$_{1-6}$alkyl, or R is absent; and/or
the structure of Formula II-A serves as a core structure for further conjugation with the precursor molecules to form a larger conjugated triangular structure.

In some embodiments of any of the triangular carbon quantum dots described herein, the precursor molecules are used to form a conjugated triangular structure comprising a structure of Formula II-B:

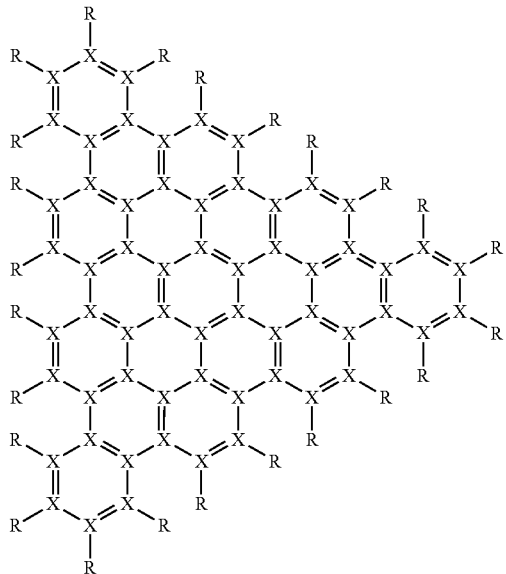

(II-B)

wherein
each X is independently selected from the group consisting of C, N, P, and B;
each R is independently selected from the group consisting of —OR$^a$, —NR$^b$R$^c$, —SR$^d$, COOR$^e$, and —B(OR$^f$)(OR$^g$), wherein R$^a$, R$^b$, R$^c$, R$^d$, R$^e$, R$^f$ and R$^g$ are each independently H or C$_{1-6}$alkyl, or R is absent; and/or
the structure of Formula II-B serves as a core structure for further conjugation with the precursor molecules to form a larger conjugated triangular structure.

In some embodiments of any of the triangular carbon quantum dots described herein, each pair of adjacent R groups in the structure of Formula I, Formula I-A, Formula I-B, Formula II, Formula II-A, or Formula II-Bare configured to form additional 6-membered rings, thereby creating a larger conjugated triangular structure. In some embodiments, the triangular carbon quantum dot is doped with N, S, P, B or O.

In some embodiments of any of the triangular carbon quantum dots described herein, triangular carbon quantum dot has an emission peak ranging from about 400 nm to about 700 nm. In some embodiments, the triangular carbon quantum dot has a full width at half maximum (FWHM) ranging from about 20 nm to about 70 nm.

In some embodiments of any of the triangular carbon quantum dots described herein, the triangular carbon quantum dot has a size or diameter ranging from about 1 nm to about 6 nm. In some embodiments, the triangular carbon quantum dot has a quantum yield (QY) ranging from about 50% to about 75%.

In some embodiments of any of the triangular carbon quantum dots described herein, the triangular carbon quantum dot has an emission peak ranging from about 460 nm to about 480 nm and a size or diameter ranging from about 1.8 nm to about 2.0 nm. In some embodiments, the triangular carbon quantum dot has an emission peak ranging from about 500 nm to about 520 nm and a size or diameter ranging from about 2.2 nm to about 2.5 nm. In some embodiments, the triangular carbon quantum dot has an emission peak ranging from about 530 nm to about 550 nm and a size or diameter ranging from about 2.9 nm to about 3.1 nm. In some embodiments, the triangular carbon quantum dot has an emission peak ranging from about 590 nm to about 610 nm and a size or diameter ranging from about 3.8 nm to about 4.1 nm.

Provided in some aspects are methods for preparing a triangular carbon quantum dot of any of the embodiments described herein. In some embodiments, the method of preparing a triangular carbon quantum dot described herein involves solvothermal synthesis using at least three precursor molecules each containing an aromatic ring, e.g., a 6-member aromatic ring, to form a triangular carbon quantum dot.

In some embodiments of any of the methods described herein, the method involves forming a conjugated triangular structure of Formula I

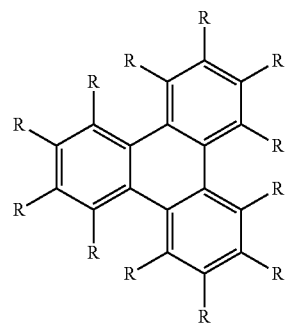

(I)

by solvothermal synthesis using precursor molecules of Formula A-1:

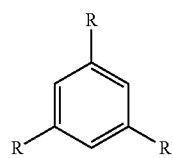

(A-1)

wherein each R is independently selected from the group consisting of —OR$^a$, —NR$^b$R$^c$, —SR$^d$, COOR$^e$, and —B(OR$^f$)(OR$^g$), wherein R$^a$, R$^b$, R$^c$, R$^d$, R$^e$, R$^f$ and R$^g$ are each independently H or C$_{1-6}$alkyl.

In some embodiments of any of the methods described herein, the method involves forming a conjugated triangular structure of Formula I-A

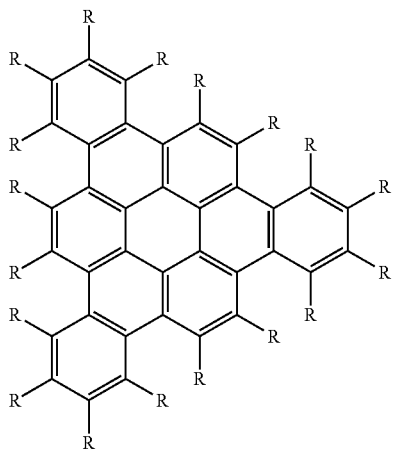

by solvothermal synthesis using precursor molecules of Formula A-1:

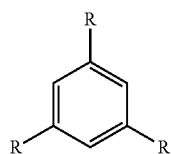
(A-1)

wherein each R is independently selected from the group consisting of —OR$^a$, —NR$^b$R$^c$, —SR$^d$, COOR$^e$, and —B(OR$^f$)(OR$^g$), wherein R$^a$, R$^b$, R$^c$, R$^d$, R$^e$, R$^f$ and R$^g$ are each independently H or C$_{1-6}$alkyl.

In some embodiments of any of the methods described herein, the method involves forming a conjugated triangular structure of Formula I-B (I-B)

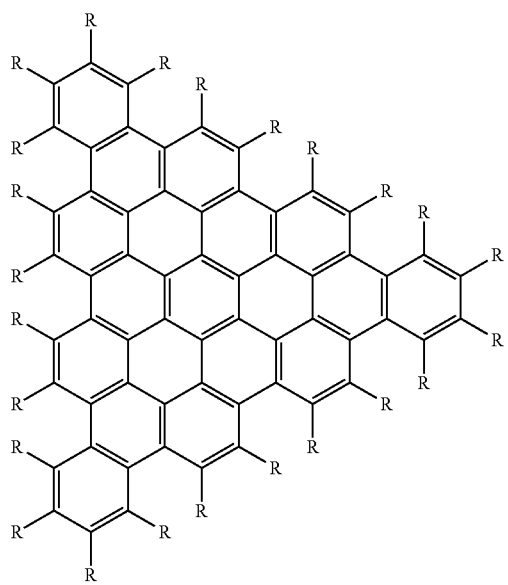

by solvothermal synthesis using precursor molecules of Formula A-1:

wherein each R is independently selected from the group consisting of —OR$^a$, —NR$^b$R$^c$, —SR$^d$, COOR$^e$, and —B(OR$^f$)(OR$^g$), wherein R$^a$, R$^b$, R$^c$, R$^d$, R$^e$, R$^f$ and R$^g$ are each independently H or C$_{1-6}$alkyl.

In some embodiments of any of the methods described herein, the method further involves conjugating the structure of Formula I, Formula I-A or Formula I-B as a core structure with the precursor molecules of Formula A to form a larger conjugated triangular structure. In some embodiments of any of the methods described herein, each pair of adjacent R groups in the structure of Formula I, Formula I-A or Formula I-B are conjugated with the precursor molecules of Formula A to form additional 6-membered rings, thereby creating a larger conjugated triangular structure.

In some embodiments of any of the methods described herein, the method involves forming a conjugated triangular structure of Formula II (II)

by solvothermal synthesis using precursor molecules of Formula A:

(A)

wherein each X is independently selected from the group consisting of C, N, P, and B; and each R is independently selected from the group consisting of —OR$^a$, —NR$^b$R$^c$, —SR$^d$, COOR$^e$, and —B(OR$^f$)(OR$^g$), wherein R$^a$, R$^b$, R$^c$, R$^d$, R$^e$, R$^f$ and R$^g$ are each independently H or C$_{1-6}$alkyl, or R may be absent.

In some embodiments of any of the methods described herein, the method involves forming a conjugated triangular structure of Formula II-A by solvothermal synthesis using precursor molecules of Formula A:

(II-A)

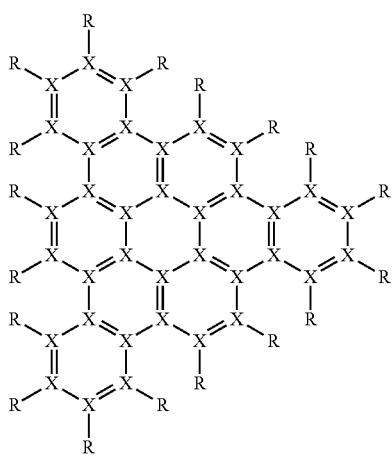

(A)

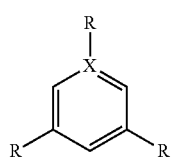

wherein
each X is independently selected from the group consisting of C, N, P, and B; and
each R is independently selected from the group consisting of —OR$^a$, —NR$^b$R$^c$, —SR$^d$, COOR$^e$, and —B(OR$^f$)(OR$^g$), wherein R$^a$, R$^b$, R$^c$, R$^d$, R$^e$, R$^f$ and R$^g$ are each independently H or C$_{1-6}$alkyl, or R may be absent.

In some embodiments of any of the methods described herein, the method involves forming a conjugated triangular structure of Formula II-B (II-B)

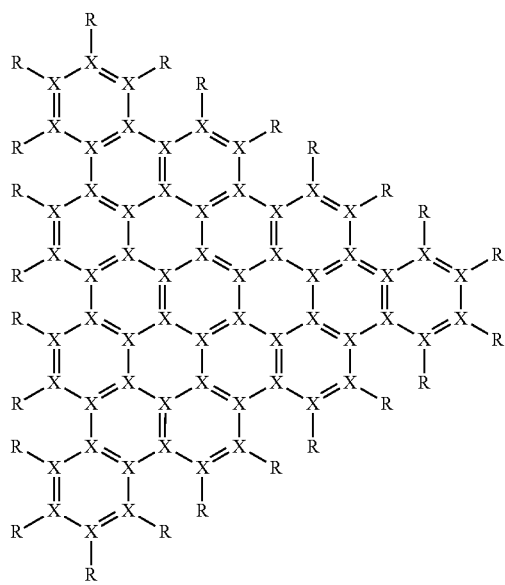

by solvothermal synthesis using precursor molecules of Formula A:

(A)

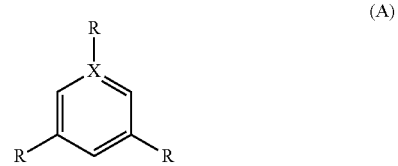

wherein
each X is independently selected from the group consisting of C, N, P, and B; and
each R is independently selected from the group consisting of —OR$^a$, —NR$^b$R$^c$, —SR$^d$, COOR$^e$, and —B(OR$^f$)(OR$^g$), wherein R$^a$, R$^b$, R$^c$, R$^d$, R$^e$, R$^f$ and R$^g$ are each independently H or C$_{1-6}$alkyl, or R may be absent.

In some embodiments of any of the methods described herein, the method further involves conjugating the structure of Formula II, Formula II-A, or Formula II-B as a core structure with the precursor molecules of Formula A or Formula A-1 to form a larger conjugated triangular structure. In some embodiments of any of the methods described herein, each pair of adjacent R groups in the structure of Formula II, Formula II-A or Formula II-B are conjugated with the precursor molecules of Formula A or Formula A-1 to form additional 6-membered rings, thereby creating a larger conjugated triangular structure.

In some embodiments of any of the methods described herein, the method involves each of the precursor molecules of Formula A is selected from the group consisting of

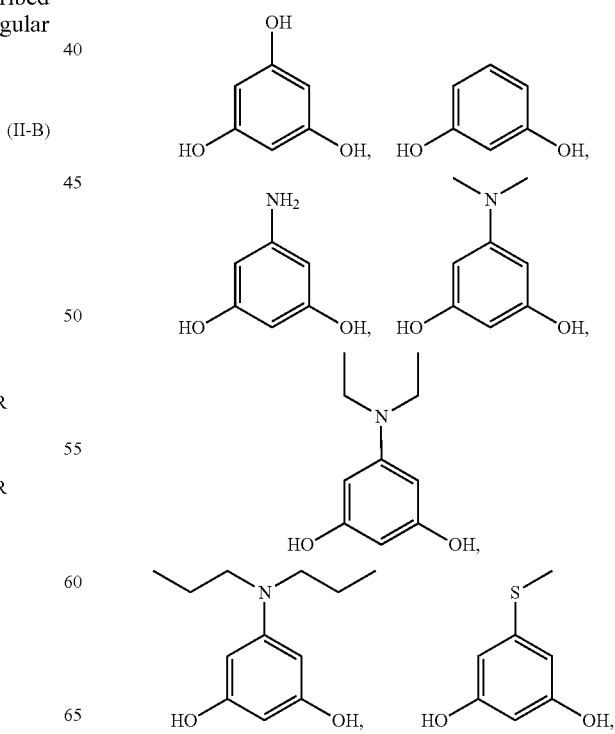

-continued

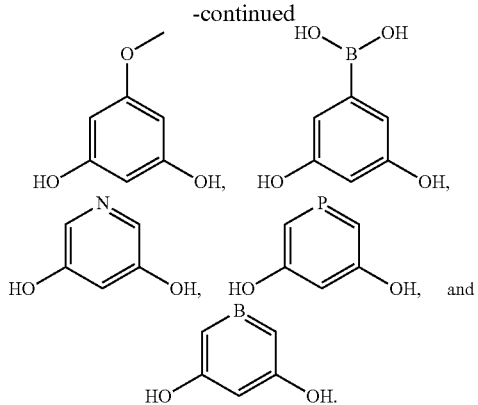

In some embodiments, the precursor molecule of Formula A is

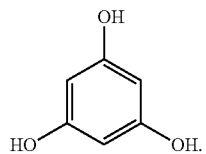

In some embodiments of any of the methods described herein, the method involves dissolving or dispersing the precursor molecules of Formula A in a solvent to form a solution or a mixture and heating the solution or mixture at a temperature from about 100° C. to about 300° C. for a time from about 10 minutes to about 72 hours. In some embodiments, the solvent is water, a $C_{1-10}$ alcohol, e.g., ethanol, an amide, e.g., formamide or N,N-dimethyl formamide, a ketone, e.g., acetone, or a sulfoxide, e.g., dimethylsulfoxide. In some embodiments, the precursor molecules are conjugated to form conjugated triangular structure in the presence of a conjugation catalyst. In some embodiments, the conjugation catalyst is an acid, e.g., sulfuric acid, phosphoric acid, or hydrochloric acid. In some embodiments of any of the methods described herein, the method involves using a neutralizing agent to neutralize the conjugation catalyst. In some embodiments, the neutralizing agent is a base, e.g., sodium hydroxide, potassium hydroxide, sodium carbonate, or potassium carbonate.

In some embodiments of any of the methods described herein, the method further involves isolating or purifying a triangular carbon quantum dot. In some embodiments, the triangular carbon quantum dot is isolated or purified via filtration, centrifugation, chromatography, e.g., column chromatography, gel-electrophoresis, or dialysis.

Provided in some embodiments are methods for preparing a triangular carbon quantum dot that involve: 1) dissolving phloroglucinol in ethanol to form a solution: 2) heating the solution at about 140° C. for about 9 hours: 3) cooling the solution to a lower temperature, e.g., room temperature; and 4) isolating or purifying a triangular carbon quantum dot from the solution, e.g., via chromatography or column chromatography.

Provided in some embodiments are methods for preparing a triangular carbon quantum dot that involve: 1) dissolving phloroglucinol in ethanol to form a solution; 2) heating the solution at about 200° C. for about 24 hours; 3) cooling the solution to a lower temperature, e.g., room temperature; and 4) isolating or purifying a triangular carbon quantum dot from the solution, e.g., via chromatography or column chromatography.

Provided in other embodiments are methods for preparing a triangular carbon quantum dot that involve: 1) dissolving phloroglucinol in ethanol to form a solution: 2) adding a conjugation catalyst, e.g., sulfuric acid, to the solution: 3) heating the solution at about 200° C. for about 2 hours; 4) cooling the solution to a lower temperature, e.g., room temperature and neutralizing the conjugation catalyst with a neutralizing agent, e.g., a base; and 5) isolating or purifying a triangular carbon quantum dot from the solution, e.g., via chromatography or column chromatography.

In yet other embodiments, provided are methods for preparing a triangular carbon quantum dot that involve: 1) dissolving phloroglucinol in ethanol to form a solution: 2) adding a conjugation catalyst, e.g., sulfuric acid, to the solution: 3) heating the solution at about 200° C. for about 5 hours; 4) cooling the solution to a lower temperature, e.g., room temperature and neutralizing the conjugation catalyst with a neutralizing agent, e.g., a base; and 5) isolating or purifying a triangular carbon quantum dot from the solution, e.g., via chromatography or column chromatography.

Provided in certain aspects are triangular carbon quantum dots that are prepared by a method of any of the embodiments described herein.

Also provided herein are articles of manufacturer containing a triangular carbon quantum dot of any of the embodiments described herein. In some embodiments, the article of manufacture is configured for imaging, sensing, catalytic, delivering, displaying, optronic, lighting, or computing application. In some embodiments, the imaging application is a biological or chemical imaging application. In some embodiments, the sensing application is a biological or chemical sensing application. In some embodiments, the catalytic application is a biological, chemical, photo, or electro catalytic application. In some embodiments, the delivering application is a biological or chemical delivering application, e.g., drug delivering application.

In some embodiments of any of the articles of manufacturer described herein, the article of manufacture is a polymer. In some embodiments, the article of manufacture is included in an imaging, a sensing, a catalytic, a delivering, a displaying, an optronic, a lighting, or a computing agent or device. In some embodiments, the article of manufacture is included in a photoelectric device, a transistor, a solar cell, a light emitting device, a light-emitting diode (LED), a diode laser, a qubit in quantum computing, a display, e.g., a television or a phone, a head-up display, e.g., a transparent head-up display, or a paint, e.g., a fluorescent paint or a luminescent paint.

Provided in other aspects are light-emitting diodes (LEDs) that contain any of the triangular carbon quantum dots described herein. In some embodiments, the LED contains an active emission layer that contains a triangular carbon quantum dot of any of the embodiments described herein. In some embodiments, the LED contains an anode, a hole injection layer, an active emission layer, an electron transport layer and a cathode. In some embodiments, the hole injection layer, the active emission layer and the electron transport layer are placed between the anode and the cathode.

In some embodiments of any of the LEDs described herein, the LED contains from one side to an opposite side, e.g., from the bottom up, an anode, a hole injection layer, an active emission layer, an electron transport layer and a cathode. In some embodiments, the LED contains a substrate that holds or supports an anode, a hole injection layer, an active emission layer, an electron transport layer and a cathode. In some embodiments, the substrate contains glass or a thermoplastic polymer, e.g., polyester or polyethylene terephthalate (PET). In some embodiments, the anode contains indium tin oxide (ITO) or graphene. In some embodiments, the substrate holds an anode to form a substrate anode. In some embodiments, the hole injection layer contains poly(3,4-ethylenedioxythiophene):poly(styrenesulfonate) (PEDOT:PSS), molybdenum oxide, e.g., $MoO_x$, X being 1-3, nickel oxide, e.g., $NiO_x$, X being 1-3, or vanadium(V) oxide, e.g., $VO_x$, X being 1-3. In some embodiments, the active emission layer contains a triangular carbon quantum dot:Y blended emission layer, Y being poly(N-vinyl carbazole) (PVK), poly-(N,N'-bis(4-butylphenyl)-N,N'-bis(phenyl) benzidine) (poly-TPD), or poly(9,9-dioctylfluorene) (PFO).

In some embodiments, the electron transport layer contains 1,3,5-tris(N-phenylbenzimidazol-2-yl) benzene (TPBI), zinc oxide (ZnO), titanium oxide, e.g., $TiO_x$, X being 1-2, or Tris(8-hydroxyquinolinato)aluminium ($Alq_3$). In some embodiments, the cathode contains Ca/Al, LiF/Al or Ag.

In some embodiments of any of the LEDs described herein, the LED contains from one side to an opposite side, e.g., from the bottom up, a ITO glass substrate anode, a poly(3,4-ethylenedioxythiophene):poly(styrenesulfonate) (PEDOT:PSS) hole injection layer (HIL), an active triangular carbon quantum dot:PVK blended emission layer, a 1,3,5-tris(N-phenylbenzimidazol-2-yl) benzene (TPBI) electron transport layer (ETL), and a Ca/Al double-layered cathode.

In some embodiments, the LED of any of the embodiments described herein has a maximum luminance from about 500 $cd/m^2$ to about 10,000 $cd/m^2$. In some embodiments, the LED of any of the embodiments described herein has a current efficiency from about 1 cd/A to about 10 cd/A. In some embodiments, the LED of any of the embodiments described herein has a turn on voltage from about 2 V to about 5 V. In some embodiments, the LED of any of the embodiments described herein has an emission range from about 460 nm to about 610 nm. In some embodiments, the LED of any of the embodiments described herein has an emission range from about 460 nm to about 480 nm. In some embodiments of any of the LEDs described herein, the LED is a green LED and has an emission range from about 500 nm to about 520 nm. In some embodiments of any of the LEDs described herein, the LED is a yellow LED and has an emission range from about 530 nm to about 550 nm. In some embodiments of any of the LEDs described herein, the LED is a red LED and has an emission range from about 590 nm to about 610 nm. In some embodiments, the LED of any of the embodiments described herein has a lifespan of at least 10,000 hours.

Also provided herein are methods for displaying a color, which includes displaying a color of a triangular carbon quantum dot of any of the embodiments described herein, an article of manufacture of any of the embodiments described herein, or a LED of any of the embodiments described herein.

BRIEF DESCRIPTION OF THE DRAWINGS

FIG. 1a shows the synthesis route of the narrow bandwidth emission triangular carbon quantum dots (NBE-T-CQDs) by solvothermal treatment of PG triangulogen. FIGS. 1b-e show the typical aberration-corrected HAADF-STEM images of blue (B-) (FIG. 1b), green (G-) (FIG. 1c), yellow (Y-) (FIG. 1d), and red (R-) NBE-T-CQDs (FIG. 1e), respectively. Scale bar, 2 nm. FIG. 1f shows photographs of the NBE-T-CQDs ethanol solutions under daylight, and FIG. 1g shows fluorescence images of the NBE-T-CQDs ethanol solutions under UV light (excited at 365 nm). FIG. 1h and FIG. 1i show the normalized UV-vis absorption (FIG. h) and PL (FIG. 1i) spectra of blue, green, yellow, and red NBE-T-CQDs, respectively.

FIG. 2a illustrates the time-resolved PL spectra of the NBE-T-CQDs. FIG. 2b shows the two-dimensional pseudocolor map of TA spectra of B-NBE-T-CQDs expressed in ΔOD (the change of the absorption intensity of the sample after excitation) as a function of both delay time and probe wavelength excited at 400 nm. FIG. 2c shows the TA spectra of B-NBE-T-CQDs at indicated delay times from 0.5 ps to 1 ns. FIG. 2d shows results of the global fitting with four exponent decay functions. FIG. 2e shows the normalized temperature-dependent PL spectra of B-NBE-T-CQDs. FIG. 2f shows the normalized PL spectra of the NBE-T-CQDs acquired at 85 K. FIG. 2g shows the plots of the emission peak energy and FWHM of B-NBE-T-CQDs as a function of temperature (85-295 K). FIG. 2h shows the plots of integrated PL emission intensity of the NBE-T-CQDs as a function of temperature (175-295 K).

FIG. 3a shows the typical aberration-corrected HAADF-STEM image of R-NBE-T-CQDs (The inset is the corresponding high-resolution image). FIG. 3b shows the wide-area TEM image of G-NBE-T-CQDs. Scale bar, 2 nm. (The triangular projections are highlighted by white contour lines). FIGS. 3c and 3f show the XRD patterns (FIG. 3c) and FT-IR spectra (FIG. 3f) of NBE-T-CQDs. FIGS. 3d, 3e, and 3g show the $^1$H-NMR (FIG. 3d), $^{13}$C-NMR (FIG. 3e), and C1s (FIG. 3g) spectra of B-NBE-T-CQDs.

FIGS. 4a-4l show the he triangular structure model CQDs consisting of 4, 10 and 19 fused benzene rings: 1) functionalized with pure electron-donating hydroxyl groups (T-CQDs-OH-1 (FIG. 4a), T-CQDs-OH-2 (FIG. 4e), T-CQDs-OH-3 (FIG. 4i)), 2) without functionalization (T-CQDs-1 (FIG. 4b), T-CQDs-2 (FIG. 4f), T-CQDs-3 (FIG. 4j)), 3) functionalized with pure electron-withdrawing carboxyl groups (T-CQDs-COOH-1 (FIG. 4c), T-CQDs-COOH-2 (FIG. 4g). T-CQDs-COOH-3 (FIG. 4k)). The square-like structure model CQDs without functionalization consisting of 4 (S-CQDs-1 (FIG. 4d)), 10 (S-CQDs-2 (FIG. 4h)) and 20 (S-CQDs-3 (FIG. 4l)) fused benzene rings. FIGS. 4m-4x show the he calculated HOMO (FIG. 4m, FIG. 4p, FIG. 4s. FIG. 4v), LUMO (FIG. 4n, FIG. 4q, FIG. 4t, FIG. 4w) and PL spectra (FIG. 4o, FIG. 4r, FIG. 4u, FIG. 4x) of T-CQDs-OH-3, T-CQDs-3, T-CQDs-COOH-3 and S-CQDs-3, respectively.

FIG. 5a shows the device structure and FIG. 5b shows the energy level diagram of the NBE-T-CQDs-based LEDs. FIGS. 5c-f show the EL spectra of the B- (FIG. 5c), G- (FIG. 5d), Y- (FIG. 5e), and R-LEDs (FIG. 5f) at different bias voltage, respectively. (Insets are the operation photographs of the B-, G-, Y-, and R-LEDs with the logo of BNU). FIGS. 5g-j show the maximum luminance-current-voltage (L-I-V)

characteristic of B- (FIG. 5g), G- (FIG. 5h), Y- (FIG. 5i), and R-LEDs (FIG. 5j), respectively. FIGS. 5k and 5l show the current efficiency versus current density (FIG. 5k) and the stability plots (FIG. 5l) of the B-, G-, Y-, and R-LEDs.

DETAILED DESCRIPTION

A. Definitions

Figure 1:
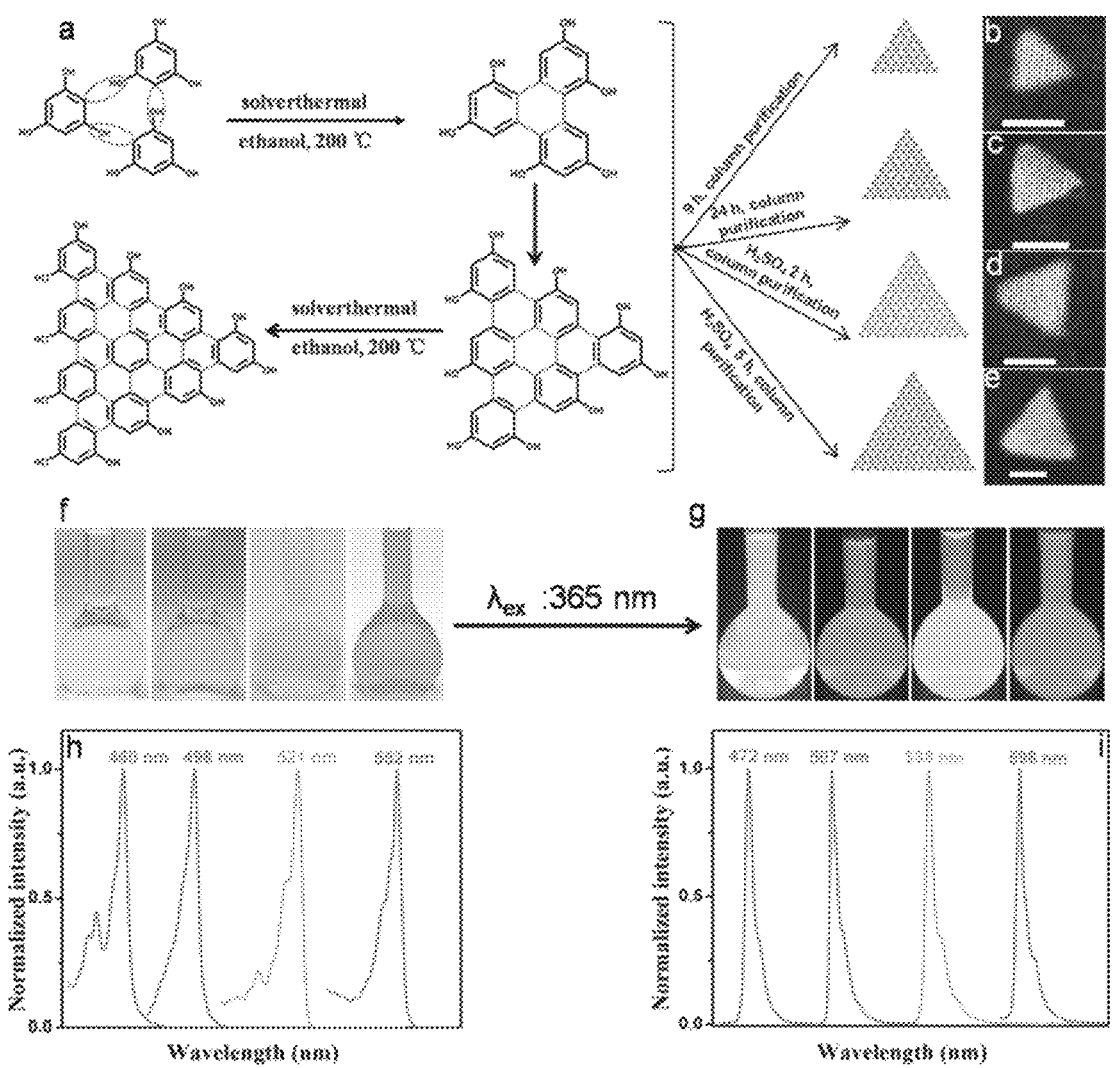
FIG. 1 depicts the design and synthesis of narrow bandwidth emission triangular CQDs.

Unless defined otherwise, all technical and scientific terms used herein have the same meaning as is commonly understood by one of ordinary skill in the art to which this invention belongs. All patents, applications, published applications and other publications referred to herein are incorporated by reference in their entireties. If a definition set forth in this section is contrary to or otherwise inconsistent with a definition set forth in a patent, application, or other publication that is herein incorporated by reference, the definition set forth in this section prevails over the definition incorporated herein by reference.

The use of "including," "comprising," or "having" and variations thereof herein is meant to encompass the items listed thereafter and equivalents thereof as well as additional items. The use of any and all examples, or exemplary language (e.g., "such as") is intended to better illuminate the embodiments and does not pose a limitation on the scope of the claims unless otherwise stated.

As used herein and in the appended claims, the singular forms "a", and "the" include plural references unless indicated otherwise. Similarly, when the plural form is used it is to be construed to cover the singular form as the context permits. For example, "a" or "an" means "at least one" or "one or more." Thus, reference to "a" triangular carbon quantum dot includes one or more triangular carbon quantum dots, and reference to "the method" includes reference to equivalent steps and methods disclosed herein and/or known to those skilled in the art, and so forth.

As used herein, reference to "about" a value or parameter herein includes (and describes) embodiments that are directed to that value or parameter per se. For example, description referring to "about X" includes description of "X".

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

As used herein, the term "functional group" as used herein refers to an atom or a group of atoms, acting as a unit, that has replaced a hydrogen atom in a compound.

As used herein, the term "alkyl" as used herein refers to saturated hydrocarbon groups in a straight, branched, or cyclic configuration or any combination thereof, and particularly contemplated alkyl groups include those having ten or less carbon atoms, especially 1-6 carbon atoms and lower alkyl groups having 1-4 carbon atoms. Exemplary alkyl groups are methyl, ethyl, propyl, isopropyl, butyl, sec-butyl, tertiary butyl, pentyl, isopentyl, hexyl, cyclopropylmethyl, etc.

Alkyl groups can be unsubstituted, or they can be substituted to the extent that such substitution makes sense chemically. Typical substituents include, but are not limited to, halo, $=O$, $=N-CN$, $=N-OR^a$, $=NR$, $-OR^a$, $-NR_2$, —SR, —SO$_2$R$^a$, —SO$_2$NR$^a$$_2$, —NR$^a$SO$_2$R$^a$, —NR$^a$-CONR$^a$$_2$, —NR$^a$COOR$^a$, —NR$^a$COR$^a$, —CN, —COOR$^a$, —CONR$^a$$_2$, —OOCR$^a$, —COR$^a$, and —NO$_2$, wherein each R$^a$ is independently H, C$_1$-C$_8$ alkyl, C$_2$-C$_5$ heteroalkyl, C$_3$-C$_5$ heterocyclyl, C$_4$-C$_{10}$ heterocyclylalkyl, C$_1$-C$_8$ acyl, C$_2$-C$_5$ heteroacyl, C$_2$-C$_5$ alkenyl, C$_2$-C$_5$ heteroalkenyl, C$_2$-C$_8$ alkynyl, C$_2$-C$_5$ heteroalkynyl, C$_6$-C$_{10}$ aryl, or C$_5$-C$_{10}$ heteroaryl, and each R$^a$ is optionally substituted with halo, =O, =N—CN, =N—OR$^b$, =NR$^b$, OR$^b$, NR$^b$$_2$, SR$^b$, SO$_2$R$^b$, SO$_2$NR$^b$$_2$, NR$^b$SO$_2$R$^b$, NR$^b$CONR$^b$$_2$, NR$^b$COOR$^b$, NR$^b$COR$^b$, CN, COOR$^b$, CONR$^b$$_2$, OOCR$^b$, COR$^b$, and NO$_2$, wherein each R$^b$ is independently H, C$_1$-C$_8$ alkyl, C$_2$-C$_8$ heteroalkyl, C$_3$-C$_8$ heterocyclyl, C$_4$-C$_{10}$ heterocyclylalkyl, C$_1$-C$_8$ acyl, C$_2$-C$_8$ heteroacyl, C$_6$-C$_{10}$ aryl or C$_5$-C$_{10}$ heteroaryl. Alkyl, alkenyl and alkynyl groups can also be substituted by C$_1$-C$_8$ acyl, C$_2$-C$_8$heteroacyl, C$_6$-C$_{10}$ aryl or C$_5$-C$_{10}$ heteroaryl, each of which can be substituted by the substituents that are appropriate for the particular group. Where a substituent group contains two R$^a$ or R$^b$ groups on the same or adjacent atoms (e.g., —NR$^b$2, or —NR$^b$—C(O) R$^b$), the two R$^a$ or R$^b$ groups can optionally be taken together with the atoms in the substituent group to which are attached to form a ring having 5-8 ring members, which can be substituted as allowed for the R$^a$ or R$^b$ itself, and can contain an additional heteroatom (N, O or S) as a ring member.

The term "aryl" or "aromatic ring" as used herein refers to a ring containing delocalized pi bonds. These are typically 5-6 membered isolated rings, or 8-10 membered bicyclic groups, and can be substituted. Thus, contemplated aryl groups include (e.g., phenyl, naphthyl, etc.) and pyridyl. Further contemplated aryl groups may be fused (i.e., covalently bound with 2 atoms on the first aromatic ring) with one or two 5- or 6-membered aryl or heterocyclic group, and are thus termed "fused aryl" or "fused aromatic".

Aromatic groups containing one or more heteroatoms (typically N, O or S) as ring members can be referred to as heteroaryl or heteroaromatic groups. Typical heteroaromatic groups include monocyclic C$_5$-C$_6$ aromatic groups such as pyridyl, pyrimidyl, pyrazinyl, thienyl, furanyl, pyrrolyl, pyrazolyl, thiazolyl, oxazolyl, isothiazolyl, isoxazolyl, and imidazolyl and the fused bicyclic moieties formed by fusing one of these monocyclic groups with a phenyl ring or with any of the heteroaromatic monocyclic groups to form a C$_8$-C$_{10}$ bicyclic group such as indolyl, benzimidazolyl, indazolyl, benzotriazolyl, isoquinolyl, quinolyl, benzothiazolyl, benzofuranyl, pyrazolopyridyl, pyrazolopyrimidyl, quinazolinyl, quinoxalinyl, cinnolinyl, and the like. Any monocyclic or fused ring bicyclic system which has the characteristics of aromaticity in terms of electron distribution throughout the ring system is included in this definition. It also includes bicyclic groups where at least the ring which is directly attached to the remainder of the molecule has the characteristics of aromaticity. Typically, the ring systems contain 5-12 ring member atoms.

As also used herein, the terms "heterocycle", "cycloheteroalkyl", and "heterocyclic moieties" are used interchangeably herein and refer to any compound in which a plurality of atoms form a ring via a plurality of covalent bonds, wherein the ring includes at least one atom other than a carbon atom as a ring member. Particularly contemplated heterocyclic rings include 5- and 6-membered rings with nitrogen, sulfur, or oxygen as the non-carbon atom (e.g., imidazole, pyrrole, triazole, dihydropyrimidine, indole, pyridine, thiazole, tetrazole etc.). Typically these rings contain 0-1 oxygen or sulfur atoms, at least one and typically 2-3 carbon atoms, and up to four nitrogen atoms as ring members. Further contemplated heterocycles may be fused (i.e., covalently bound with two atoms on the first heterocyclic ring) to one or two carbocyclic rings or heterocycles, and are thus termed "fused heterocycle" or "fused heterocyclic ring" or "fused heterocyclic moieties" as used herein. Where the ring is aromatic, these can be referred to herein as 'heteroaryl' or heteroaromatic groups.

Heterocyclic groups that are not aromatic can be substituted with groups suitable for alkyl group substituents, as set forth above.

Aryl and heteroaryl groups can be substituted where permitted. Suitable substituents include, but are not limited to, halo, —OR$^a$, —NR$^a$$_2$, —SR$^a$, —SO$_2$R$^a$, —SO$_2$NR$^a$$_2$, —NR$^a$SO$_2$R$^a$, —NR$^a$CONR$^a$$_2$, —NR$^a$COOR$^a$, —NR$^a$-COR$^a$, —CN, —COOR$^a$, —CONR$^a$$_2$, —OOCR$^a$, —COR$^a$, and —NO$_2$, wherein each R$^a$ is independently H, C$_1$-C$_8$ alkyl, C$_2$-C$_5$ heteroalkyl, C$_3$-C$_8$ heterocyclyl, C$_4$-C$_{10}$ heterocyclylalkyl, C$_1$-C$_8$ acyl, C$_2$-C$_5$ heteroacyl, C$_2$-C$_5$ alkenyl, C$_2$-C$_8$ heteroalkenyl, C$_2$-C$_5$ alkynyl, C$_2$-C$_5$ heteroalkynyl, C$_6$-C$_{10}$ aryl, or C$_5$-C$_{10}$ heteroaryl, and each R$^a$ is optionally substituted with halo, =O, =N—CN, =N—OR$^b$, =NR$^b$, OR$^b$, NR$^b$$_2$, SR$^b$, SO$_2$R$^b$, SO$_2$NR$^b$2, NR$^b$SO$_2$R$^b$, NR$^b$-CONR$^b$$_2$, NR$^a$COOR$^b$, NR$^b$COR$^b$, CN, COOR$^b$, CONR$^b$$_2$, OOCR$^b$, COR$^b$, and NO$_2$, wherein each R$^a$ is independently H, C$_1$-C$_8$ alkyl, C$_2$-C$_8$ heteroalkyl, C$_3$-C$_5$ heterocyclyl, C$_4$-C$_{10}$ heterocyclylalkyl, C$_1$-C$_8$ acyl, C$_2$-C$_5$ heteroacyl, C$_6$-C$_{10}$ aryl or C$_5$-C$_{10}$ heteroaryl. Alkyl, alkenyl and alkynyl groups can also be substituted by C$_1$-C$_8$ acyl, C$_2$-C$_8$ heteroacyl, C$_6$-C$_{10}$ aryl or C$_5$-C$_{10}$ heteroaryl, each of which can be substituted by the substituents that are appropriate for the particular group. Where a substituent group contains two R$^a$ or R$^b$ groups on the same or adjacent atoms (e.g., —NR$^b$$_2$, or —NR$^b$—C(O) R$^b$), the two R$^a$ or R$^b$ groups can optionally be taken together with the atoms in the substituent group to which are attached to form a ring having 5-8 ring members, which can be substituted as allowed for the R$^a$ or R$^b$ itself, and can contain an additional heteroatom (N, O or S) as a ring member.

The term 'amino' as used herein refers to the group —NH$_2$. The term "alkylamino" refers to amino groups where one or both hydrogen atoms are replaced by a hydrocarbon group He as described above, wherein the amino nitrogen "N" can be substituted by one or two He groups as set forth for alkoxy groups described above. Exemplary alkylamino groups include methylamino, dimethylamino, ethylamino, diethylamino, etc. Also, the term "substituted amino" refers to amino groups where one or both hydrogen atoms are replaced by a hydrocarbon group He as described above, wherein the amino nitrogen "N" can be substituted by one or two He groups as set forth for alkoxy groups described above.

The term 'acyl' as used herein refers to a group of the formula —C(=O)-D, where D represents an alkyl, alkenyl, alkynyl, cycloalkyl, aryl, heteroaryl, or heterocycle as described above. Typical examples are groups wherein D is a C$_1$-C$_{10}$ alkyl, C$_2$-C$_{10}$ alkenyl or alkynyl, or phenyl, each of which is optionally substituted. In some embodiments, D can be H, Me, Et, isopropyl, propyl, butyl, C$_1$-C$_4$ alkyl substituted with —OH, —OMe, or NH$_2$, phenyl, halophenyl, alkylphenyl, and the like.

The term "halo" or "halogen" as used herein refers to fluorine, chlorine, bromine and iodine. Where present as a substituent group, halogen or halo typically refers to F or Cl or Br, more typically F or Cl.

It should further be recognized that all of the above-defined groups may further be substituted with one or more substituents, which may in turn be substituted with hydroxy, amino, cyano, C$_1$-C$_4$ alkyl, halo, or C$_1$-C$_4$ haloalkyl. For example, a hydrogen atom in an alkyl or aryl can be replaced by an amino, halo or $C_1$-$C_4$ haloalkyl or alkyl group.

The term "substituted" as used herein refers to a replacement of a hydrogen atom of the unsubstituted group with a functional group, and particularly contemplated functional groups include nucleophilic groups (e.g., —$NH_2$, —OH, —SH, —CN, etc.), electrophilic groups (e.g., C(O)OR, C(X)OH, etc.), polar groups (e.g., —OH), non-polar groups (e.g., heterocycle, aryl, alkyl, alkenyl, alkynyl, etc.), ionic groups (e.g., —$NH_3$), and halogens (e.g., —F, —Cl), NHCOR, $NHCONH_2$, $OCH_2COOH$, $OCH_2CONH_2$, $OCH_2CONHR$, $NHCH_2COOH$, $NHCH_2CONH_2$, $NHSO_2R$, $OCH_2$-heterocycles, $PO_3H$, $SO_3H$, amino acids, and all chemically reasonable combinations thereof. Moreover, the term "substituted" also includes multiple degrees of substitution, and where multiple substituents are disclosed or claimed, the substituted compound can be independently substituted by one or more of the disclosed or claimed substituent moieties.

In general, a carbon quantum dot is a quantum dot having carbon as the primary component. For instance, in some embodiments, the content of carbon atoms in the carbon quantum dots is 50 weight % or more, such as 60 weight % or more, such as 70 weight % or more, such as 80 weight % or more, such as 90 weight % or more, such as 95 weight % or more and about 100 weight % or less.

In general, a carbon quantum dot may be characterized as a particle, the shape of which may be spherical, cylindrical, ellipsoidal, or other shape. The size or average size of the carbon quantum dot may refer to a dimension characteristic of its shape or an approximation of its shape. For instance, the size may refer to a diameter, a major axis, a predominant length, etc. In general, a carbon quantum dot is on the order of nanometers. In addition, the carbon quantum dots may be aggregates of carbon. The aggregates may be covalently or ionically bound. In some embodiments, the carbon quantum dots (or aggregates) may have a size of about 1 nm or greater, such as about 2 nm or greater and about 1000 nm or less, such as about 500 nm or less, such as about 250 nm or less, such as about 150 nm or less, such as about 100 nm or less, such as about 50 nm or less, such as about 20 nm or less, such as about 15 nm or less, such as about 10 nm or less.

B. Triangular Carbon Quantum Dots

In some aspects, provided herein are triangular carbon quantum dots with narrow bandwidth emission, methods of making them, and methods of using such triangular carbon quantum dots, such as in multicolored LED displays.

Provided in some aspects, the present disclosure describes a triangular carbon quantum dot containing a conjugated triangular structure that includes at least four aromatic rings. In some embodiments, the conjugated triangular structure includes a side functional group. In some embodiments, the content of carbon atoms in the triangular carbon quantum dot is about 50 weight % or more. For example, the content of carbon atoms in the triangular carbon quantum dot can be about 60 weight % or more, about 70 weight % or more, about 80 weight % or more, about 90 weight % or more, about 95 weight % or more, about 96 weight % or more, about 97 weight % or more, about 98 weight % or more, or about 99 weight % or more.

In some embodiments of the triangular carbon quantum dots described herein, the conjugated triangular structure contains a 6-member aromatic core ring fused to at least three aromatic rings, 6 ring atoms of the core ring being two ring atoms of each of the at least three aromatic rings. In some embodiments of any of the triangular carbon quantum dots described herein, the conjugated triangular structure contains a single 6-member aromatic core ring fused to the at least three aromatic rings. In some embodiments of any of the triangular carbon quantum dots described herein, the conjugated triangular structure comprises a plurality of the 6-member aromatic core rings fused to the at least three aromatic rings. In some embodiments of any of the triangular carbon quantum dots described herein, the conjugated triangular structure comprises at least 4, 10, 19 or 34 or more 6-member aromatic core rings fused to the at least three aromatic rings. In some embodiments of any of the triangular carbon quantum dots described herein, each of the at least three aromatic rings fused to the core ring is a 6-member aromatic ring.

In some embodiments of any of the triangular carbon quantum dots described herein, the core ring is formed by conjugation of at least three aromatic ring precursors. In some embodiments, at least one of the aromatic ring precursors is a substituted benzene. In other embodiments, each of the at least three aromatic ring precursors is a substituted benzene.

In some embodiments of any of the triangular carbon quantum dots described herein, at least one of the three aromatic ring precursors is selected from the group consisting of benzene-1,3,5-triol (phloroglucinol), resorcinol, 5-aminobenzene-1,3-diol, 5-(dimethylamino)benzene-1,3-diol, 5-(diethylamino)benzene-1,3-diol, 5-(dipropylamino)benzene-1,3-diol, 5-(methylthio)benzene-1,3-diol, 5-methoxybenzene-1,3-diol, 3,5-dihydroxyphenylboronic acid, pyridine-3,5-diol, phosphinine-3,5-diol, and borinine-3,5-diol.

In some embodiments of any of the triangular carbon quantum dots described herein, at least one of the aromatic ring precursors comprises a hetero aromatic ring. In some embodiments, the hetero aromatic ring comprises one or more heteroatoms selected from the group consisting of N, P, and B.

In some embodiments of any of the triangular carbon quantum dots described herein, the at least three aromatic rings comprise the same aromatic ring. In other embodiments, the at least three aromatic rings comprises different aromatic rings.

In some embodiments, the triangular carbon quantum dots described herein are prepared by solvothermal synthesis using at least three precursor molecules each comprising an aromatic ring. In some embodiments, each of the precursor molecules comprises a 6-member aromatic ring.

In some embodiments of any of the triangular carbon quantum dots described herein, each of the precursor molecules is a compound having a structure of Formula A:

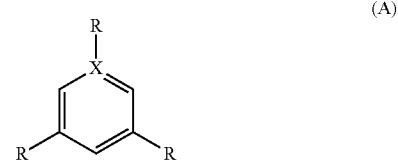

(A)

wherein X is selected from the group consisting of C, N, P, and B; and each R is independently selected from the group consisting of —$OR^a$, —$NR^bR^c$, —$SR^d$, —$COOR^e$, and —$B(OR^f)(OR^g)$, wherein $R^a$, $R^b$, $R^c$, $R^d$, $R^e$, $R^f$ and $R^g$ are each independently H or $C_{1-6}$alkyl, or R may be absent. In some embodiments, each R is independently selected from the group consisting of hydroxy, amino, dimethylamino, diethylamino, dipropylamino, methylthio, methoxy, and —B(OH)$_2$, or R may be absent. In some embodiments, each of the precursor molecules is selected from the group consisting of

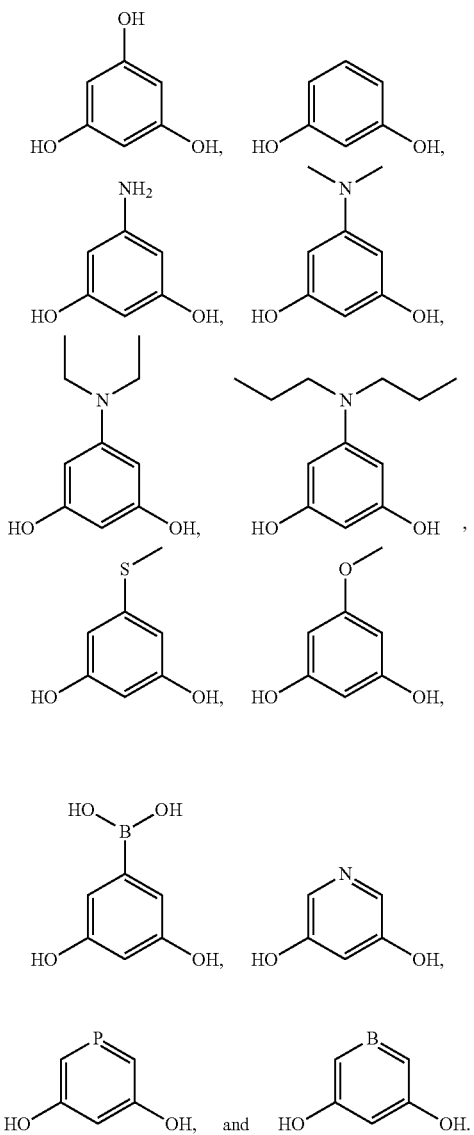

In some embodiments, each of the precursor molecules

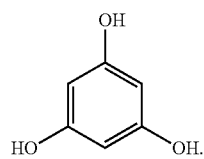

In some embodiments of any of the triangular carbon quantum dots described herein, the precursor molecules are used to form a conjugated triangular structure comprising a structure of Formula I:

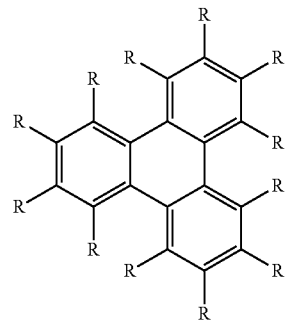

wherein each R is independently selected from the group consisting of —OR$^a$, —NR$^b$R$^c$, —SR$^d$, COOR$^e$, and —B(OR$^f$)(OR$^g$), wherein R$^a$, R$^b$, R$^c$, R$^d$, R$^e$, R$^f$ and R$^g$ are each independently H or C$_{1-6}$alkyl; and/or the structure of Formula I serves as a core structure for further conjugation with the precursor molecules to form a larger conjugated triangular structure.

In some embodiments of any of the triangular carbon quantum dots described herein, the precursor molecules are used to form a conjugated triangular structure comprising a structure of Formula I-A:

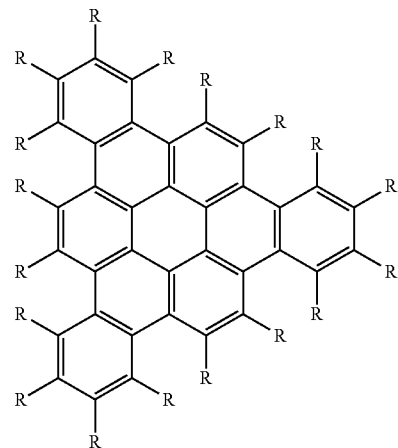

wherein each R is independently selected from the group consisting of —OR$^a$, —NR$^b$R$^c$, —SR$^d$, COOR$^e$, and —B(OR$^f$)(OR$^g$), wherein R$^a$, R$^b$, R$^c$, R$^d$, R$^e$, R$^f$ and R$^g$ are each independently H or C$_{1-6}$alkyl; and/or the structure of Formula I-A serves as a core structure for further conjugation with the precursor molecules to form a larger conjugated triangular structure.

In some embodiments of any of the triangular carbon quantum dots described herein, the precursor molecules are used to form a conjugated triangular structure comprising a structure of Formula I-B:

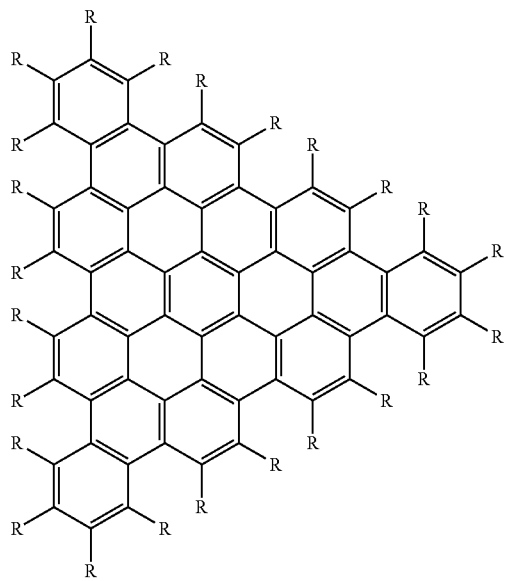

(I-B)

wherein
each R is independently selected from the group consisting of —$OR^a$, —$NR^bR^c$, —$SR^d$, $COOR^e$, and —$B(OR^f)(OR^g)$, wherein $R^a$, $R^b$, $R^c$, $R^d$, $R^e$, $R^f$ and $R^g$ are each independently H or $C_{1-6}$alkyl; and/or the structure of Formula I-B serves as a core structure for further conjugation with the precursor molecules to form a larger conjugated triangular structure.

In some embodiments, the triangular carbon quantum dot of Formula I, I-A, or I-B is doped with N, S, P, B or O, or any combination thereof. In some embodiments, the triangular carbon quantum dot of Formula I, I-A, or I-B is doped with N, S, P, B or O, or any combination thereof to form a triangular carbon quantum dot of Formula II, II-A, or II-B.

In some embodiments of any of the triangular carbon quantum dots described herein, the precursor molecules are used to form a conjugated triangular structure comprising a structure of Formula II:

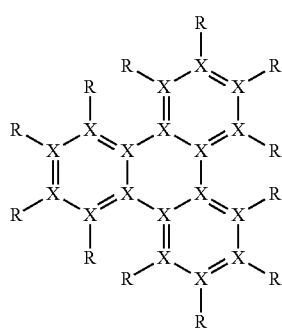

(II)

wherein
each X is independently selected from the group consisting of C, N, P, and B;

each R is independently selected from the group consisting of —$OR^a$, —$NR^bR^c$, —$SR^d$, $COOR^e$, and —$B(OR^f)(OR^g)$, wherein $R^a$, $R^b$, $R^c$, $R^d$, $R^e$, $R^f$ and $R^g$ are each independently H or $C_{1-6}$alkyl, or R is absent; and/or the structure of Formula II serves as a core structure for further conjugation with the precursor molecules to form a larger conjugated triangular structure.

In some embodiments of any of the triangular carbon quantum dots described herein, the precursor molecules are used to form a conjugated triangular structure comprising a structure of Formula II-A:

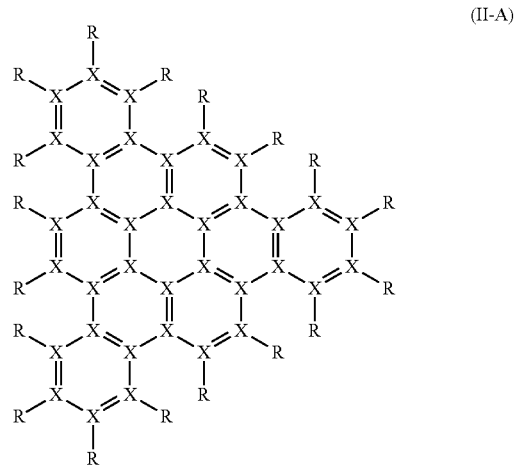

(II-A)

wherein
each X is independently selected from the group consisting of C, N, P, and B;

each R is independently selected from the group consisting of —$OR^a$, —$NR^bR^c$, —$SR^d$, $COOR^e$, and —$B(OR^f)(OR^g)$, wherein $R^a$, $R^b$, $R^c$, $R^d$, $R^e$, $R^f$ and $R^g$ are each independently H or $C_{1-6}$alkyl, or R is absent; and/or the structure of Formula II-A serves as a core structure for further conjugation with the precursor molecules to form a larger conjugated triangular structure.

In some embodiments of any of the triangular carbon quantum dots described herein, the precursor molecules are used to form a conjugated triangular structure comprising a structure of Formula II-B:

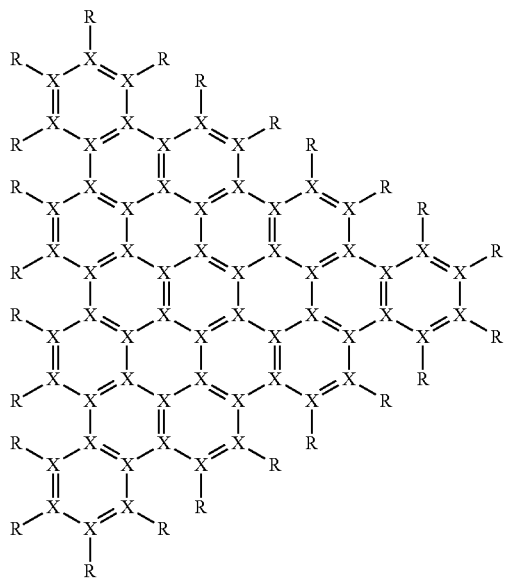

(II-B)

wherein
each X is independently selected from the group consisting of C, N, P, and B;
each R is independently selected from the group consisting of —OR$^a$, —NR$^b$R$^c$, —SR$^d$, COOR$^e$, and —B(OR$^f$)(OR$^g$), wherein R$^a$, R$^b$, R$^c$, R$^d$, R$^e$, R$^f$ and R$^g$ are each independently H or C$_{1-6}$alkyl, or R is absent; and/or
the structure of Formula II-B serves as a core structure for further conjugation with the precursor molecules to form a larger conjugated triangular structure.

In some embodiments of Formula II, Formula II-A or Formula II-B, more than 50% of the X groups are C, such as more than about 60%, more than about 70%, more than about 80%, more than about 90%, more than about 95%, more than about 96%, more than about 97%, more than about 98%, or more than about 99% or more.

In some embodiments of any of the triangular carbon quantum dots described herein, each pair of adjacent R groups in the structure of Formula I, Formula I-A. Formula I-B, Formula II, Formula II-A or Formula II-Bare configured to form additional 6-membered rings, thereby creating a larger conjugated triangular structure. In some embodiments, the triangular carbon quantum dot is doped with N, S, P, B or O, or any combination thereof.

In some embodiments, the triangular carbon quantum dot has an emission peak ranging from about 400 nm to about 700 nm. For example, in some embodiments, the triangular carbon quantum dot has an emission peak ranging from about 400 nm to about 450 nm, from about 400 nm to about 500 nm, from about 450 nm to about 500 nm, from about 450 nm to about 550 nm, from about 500 nm to about 550 nm, from about 500 nm to about 600 nm, from about 550 nm to about 600 nm, from about 550 nm to about 650 nm, from about 600 nm to about 650 nm, or from about 600 nm to about 700 nm.

In some embodiments, the triangular carbon quantum dot has a full width at half maximum (FWHM) ranging from about 20 nm to about 70 nm. For example, in some embodiments, the triangular carbon quantum dot has a FWHM ranging from about 20 nm to about 30 nm, from about 20 nm to about 40 nm, from about 20 nm to about 50 nm, from about 20 nm to about 60 nm, from about 30 nm to about 40 nm, from about 30 nm to about 50 nm, from about 30 nm to about 60 nm, from about 30 nm to about 70 nm, from about 40 nm to about 50 nm, from about 40 nm to about 60 nm, from about 40 nm to about 70 nm, from about 50 nm to about 60 nm, from about 50 nm to about 70 nm, or from about 60 nm to about 70 nm.

In some embodiments of any of the triangular carbon quantum dots described herein, the triangular carbon quantum dot has a size or diameter ranging from about 1 nm to about 6 nm. For example, in some embodiments, the triangular carbon quantum dot has a size or diameter ranging from about 1 nm to about 2 nm, from about 1 nm to about 3 nm, from about 1 nm to about 4 nm, from about 1 nm to about 5 nm, from about 2 nm to about 3 nm, from about 2 nm to about 4 nm, from about 2 nm to about 5 nm, from about 2 nm to about 6 nm, from about 3 nm to about 4 nm, from about 3 nm to about 5 nm, from about 3 nm to about 6 nm, from about 4 nm to about 5 nm, from about 4 nm to about 6 nm, or from about 5 nm to about 6 nm.

In some embodiments, the triangular carbon quantum dot has a quantum yield (QY) ranging from about 50% to about 75%. For example, in some embodiments, the triangular carbon quantum dot has a quantum yield (QY) ranging from about 50% to about 55%, from about 50% to about 60%, from about 50% to about 65%, from about 50% to about 70%, from about 55% to about 60%, from about 55% to about 65%, from about 55% to about 70%, from about 55% to about 75%, from about 60 to about 65%, from about 60% to about 70%, from about 60% to about 75%, from about 65% to about 70%, from about 65% to about 75%, or from about 70% to about 75%.

In some embodiments of any of the triangular carbon quantum dots described herein, the triangular carbon quantum dot has an emission peak ranging from about 460 nm to about 480 nm and a size or diameter ranging from about 1.8 nm to about 2.0 nm. In some embodiments, the triangular carbon quantum dot has an emission peak ranging from about 500 nm to about 520 nm and a size or diameter ranging from about 2.2 nm to about 2.5 nm. In some embodiments, the triangular carbon quantum dot has an emission peak ranging from about 530 nm to about 550 nm and a size or diameter ranging from about 2.9 nm to about 3.1 nm. In some embodiments, the triangular carbon quantum dot has an emission peak ranging from about 590 nm to about 610 nm and a size or diameter ranging from about 3.8 nm to about 4.1 nm.

C. Methods of Making Triangular Carbon Quantum Dots

Also provided herein are methods for preparing a triangular carbon quantum dot of any of the embodiments described herein. In some embodiments, the method of preparing a triangular carbon quantum dot described herein includes solvothermal synthesis using at least three precursor molecules each comprising an aromatic ring, e.g., a 6-member aromatic ring, to form a triangular carbon quantum dot.

In some embodiments, the method comprises forming a conjugated triangular structure of Formula I

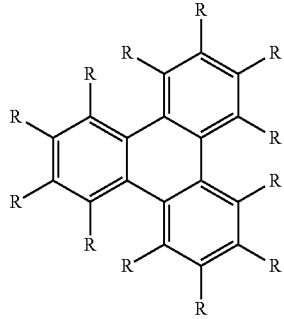
(I)

by solvothermal synthesis using precursor molecules of Formula A-1:

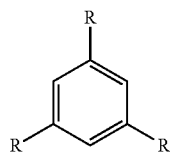
(A-1)

wherein each R is independently selected from the group consisting of —OR$^a$, —NR$^b$R$^c$, —SR$^d$, COOR$^e$, and —B(OR$^f$)(OR$^g$), wherein R$^a$, R$^b$, R$^c$, R$^d$, R$^e$, R$^f$ and R$^g$ are each independently H or C$_{1-6}$alkyl.

In some embodiments, the method comprises forming a conjugated triangular structure of Formula I-A

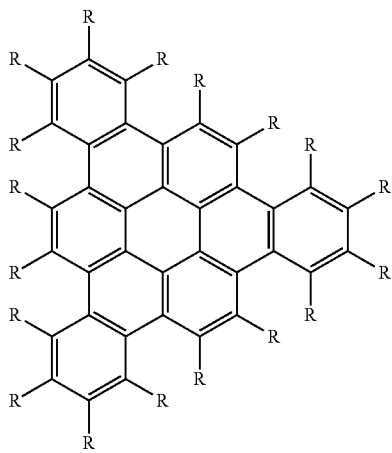
(I-A)

by solvothermal synthesis using precursor molecules of Formula A-1:

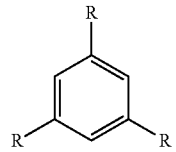
(A-1)

wherein each R is independently selected from the group consisting of —OR$^a$, —NR$^b$R$^c$, —SR$^d$, COOR$^e$, and —B(OR$^f$)(OR$^g$), wherein R$^a$, R$^b$, R$^c$, R$^d$, R$^e$, R$^f$ and R$^g$ are each independently H or C$_{1-6}$alkyl.

In some embodiments, the method comprises forming a conjugated triangular structure of Formula I-B

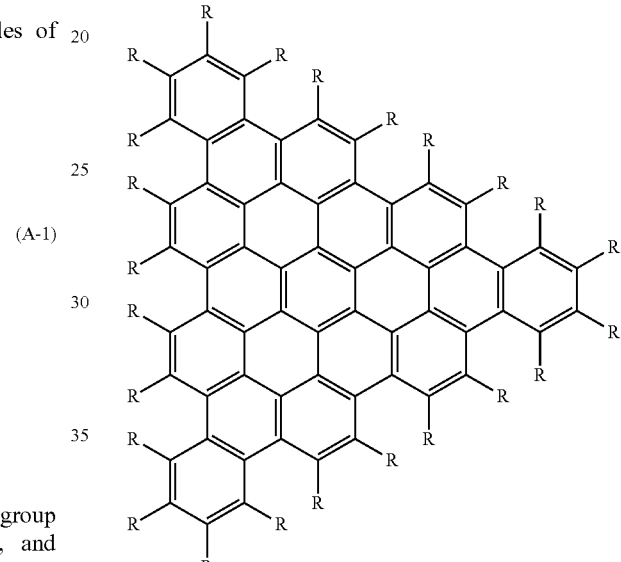
(I-B)

by solvothermal synthesis using precursor molecules of Formula A-1:

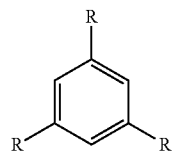
(A-1)

wherein each R is independently selected from the group consisting of —OR$^a$, —NR$^b$R$^c$, —SR$^d$, COOR$^e$, and —B(OR$^f$)(OR$^g$), wherein R$^a$, R$^b$, R$^c$, R$^d$, R$^e$, R$^f$ and R$^g$ are each independently H or C$_{1-6}$alkyl.

In some embodiments, the method further comprises conjugating the structure of Formula I, Formula I-A or Formula I-B as a core structure with the precursor molecules of Formula A to form a larger conjugated triangular structure. In some embodiments, each pair of adjacent R groups in the structure of Formula I, Formula I-A or Formula I-B are conjugated with the precursor molecules of Formula A to form additional 6-membered rings, thereby creating a larger conjugated triangular structure.

In some embodiments, the method comprises forming a conjugated triangular structure of Formula II

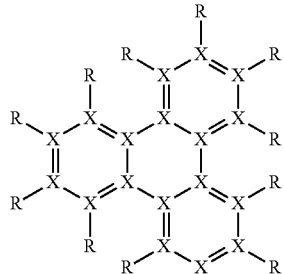 (II)

by solvothermal synthesis using precursor molecules of Formula A:

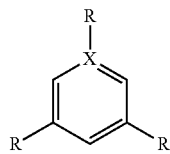 (A)

wherein
each X is independently selected from the group consisting of C, N, P, and B; and
each R is independently selected from the group consisting of —OR$^a$, —NR$^b$R$^c$, —SR$^d$, COOR$^e$, and —B(OR$^f$)(OR$^g$), wherein R$^a$, R$^b$, R$^c$, R$^d$, R$^e$, R$^f$ and R$^g$ are each independently H or C$_{1-6}$alkyl, or R is absent.

In some embodiments, the method comprises forming a conjugated triangular structure of Formula II-A

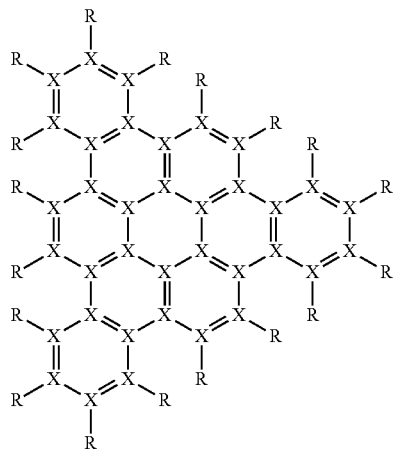 (II-A)

by solvothermal synthesis using precursor molecules of Formula A:

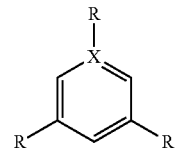 (A)

wherein
each X is independently selected from the group consisting of C, N, P, and B; and
each R is independently selected from the group consisting of —OR$^a$, —NR$^b$R$^c$, —SR$^d$, COOR$^e$, and —B(OR$^f$)(OR$^g$), wherein R$^a$, R$^b$, R$^c$, R$^d$, R$^e$, R$^f$ and R$^g$ are each independently H or C$_{1-6}$alkyl, or R is absent.

In some embodiments, the method comprises forming a conjugated triangular structure of Formula II-B (II-B)

by solvothermal synthesis using precursor molecules of Formula A:

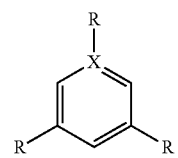 (A)

wherein
each X is independently selected from the group consisting of C, N, P, and B; and
each R is independently selected from the group consisting of —OR$^a$, —NR$^b$R$^c$, —SR$^d$, COOR$^e$, and —B(OR$^f$)(OR$^g$), wherein R$^a$, R$^b$, R$^c$, R$^d$, R$^e$, R$^f$ and R$^g$ are each independently H or C$_{1-6}$alkyl, or R is absent.

In some embodiments, the method further comprises conjugating the structure of Formula II, Formula II-A, or Formula II-B as a core structure with the precursor molecules of Formula A or Formula A-1 to form a larger conjugated triangular structure. In some embodiments, each pair of adjacent R groups in the structure of Formula II, Formula II-A or Formula II-B are conjugated with the precursor molecule s of Formula A or Formula A-1 to form additional 6-membered rings, thereby creating a larger conjugated triangular structure.

In some embodiments, each of the precursor molecules of Formula A is selected from the group consisting of

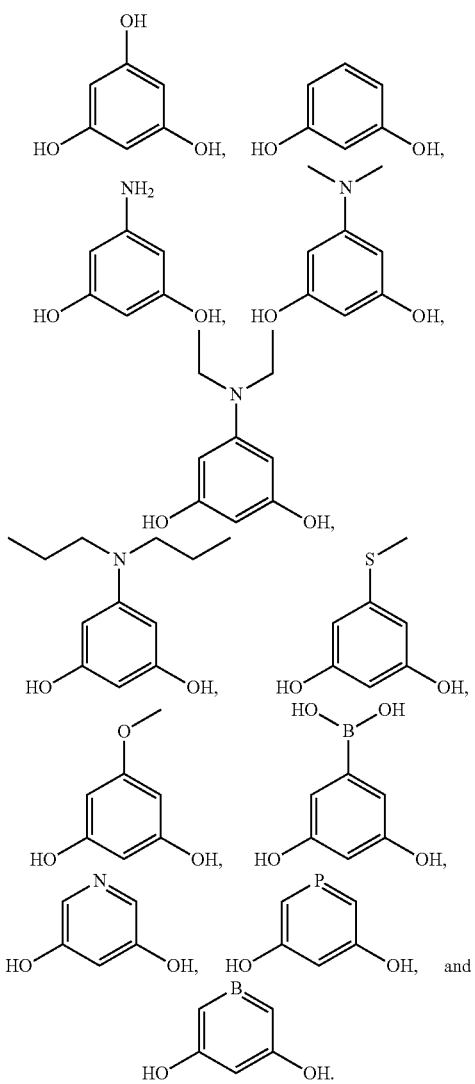

In some embodiments, the precursor molecule of Formula A is

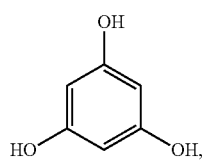

In some embodiments, the method comprises dissolving or dispersing the precursor molecules of Formula A in a solvent to form a solution or a mixture and heating the solution or mixture at a temperature from about 100° C. to about 300° C. for a time from about 10 minutes to about 72 hours. For example, in some embodiments, the method comprises heating the solution comprising the precursor molecules of Formula A at a temperature of from about 100° C. to about 150° C., from about 100° C. to about 200° C., from about 150° C. to about 200° C., from about 150° C. to about 250° C., from about 200° C. to about 250° C., from about 200° C. to about 300° C., or from about 250° C. to about 300° C. In any such embodiments, the solution can be heated from about 10 minutes to about 30 minutes, from about 10 minutes to about 60 minutes, from about 10 minutes to about 2 hours, from about 10 minutes to about 3 hours, from about 1 hour to about 2 hours, from about 1 hour to about 6 hours, from about 1 hour to about 12 hours, from about 1 hour to about 24 hours, from about 6 hours to about 12 hours, from about 6 hours to about 24 hours, from about 6 hours to about 48 hours, from about 12 hours to about 24 hours, from about 12 hours to about 48 hours, from about 12 hours to about 72 hours, from about 24 hours to about 48 hours, from about 24 hours to about 72 hours, or from about 48 hours to about 72 hours.

In some embodiments, the solvent is or comprises water. In some embodiments, the solvent is or comprises a $C_{1-10}$ alcohol. Illustrative examples include, but are not limited to, methanol, ethanol, n-propanol, isopropanol, n-butanol, 2-butanol, isobutanol, tert-butanol, pentanol, hexanol, heptanol, octanol, tert-amyl alcohol, benzyl alcohol, 1,4-butanediol, 1,2,4-butanetriol, ethylene glycol, 2-ethylhexanol, glycerol, 2-methyl-1-butanol, 2-methyl-1-pentanol, 2-methyl-2-butanol, neopentyl alcohol, 2-pentanol, 1,3-propanediol, propylene glycol, and any combination thereof. In some embodiments, the solvent comprises ethanol. In other embodiments, the solvent is or comprises an amide. Illustrative examples include, but are not limited to, dimethylacetamide, dimethylformamide, formamide, N-methyl-2-pyrrolidone, N-methylformamide, 2-pyrrolidone, tetramethylurea, N-vinylacetamide, N-vinylpyrrolidone, or any combination thereof. In some embodiments, the solvent is or comprises formamide or N,N-dimethyl formamide. In other embodiments, the solvent is or comprises a ketone. Illustrative examples include, but are not limited to, acetone, acetophenone, butanone, cyclopentanone, ethyl isopropyl ketone, 2-hexanone, isophorone, mesityl oxide, methyl isobutyl ketone, methyl isopropyl ketone, 3-methyl-2-pentanone, 2-pentanone, 3-pentanone, or any combination thereof. In some embodiments, the solvent is or comprisesacetone. In other embodiments, the solvent is or comprises a sulfoxide. In some embodiments, the solvent is or comprises dimethylsulfoxide.

In some embodiments, the precursor molecules are conjugated to form conjugated triangular structure in the presence of a conjugation catalyst. In some embodiments, the conjugation catalyst is an acid. In some embodiments, the conjugation catalyst is or comprises an inorganic acid. In some embodiments, the conjugation catalyst is selected from the group consisting of sulfuric acid, phosphoric acid, hydrochloric acid, nitric acid, boric acid, hydrofluoric acid, hydrobromic acid, perchloric acid, hydroiodic acid, or any combination thereof. In some embodiments, the conjugation catalyst comprises sulfuric acid. In some embodiments, the conjugation catalyst comprises phosphoric acid. In some embodiments, the conjugation catalyst comprises hydrochloric acid. In some embodiments, the method further comprises using a neutralizing agent to neutralize the conjugation catalyst. In some embodiments, the neutralizing agent is or comprises a base. In certain embodiments, the neutralizing agent is or comprises sodium hydroxide, potassium hydroxide, sodium carbonate, or potassium carbonate, or a combination thereof.

In some embodiments, the method further comprises isolating or purifying a triangular carbon quantum dot. In some embodiments, the triangular carbon quantum dot is isolated or purified via filtration, centrifugation, chromatography, e.g., column chromatography, gel-electrophoresis, or dialysis.

In some embodiments, the method of making triangular carbon quantum dots comprise: 1) dissolving phloroglucinol in ethanol to form a solution; 2) heating the solution at about 140° C. for about 9 hours; 3) cooling the solution to a lower temperature, e.g., room temperature; and 4) isolating or purifying a triangular carbon quantum dot from the solution, e.g., via chromatography or column chromatography.

In some embodiments, the method of making triangular carbon quantum dots comprise: 1) dissolving phloroglucinol in ethanol to form a solution; 2) heating the solution at about 200° C. for about 24 hours: 3) cooling the solution to a lower temperature, e.g., room temperature; and 4) isolating or purifying a triangular carbon quantum dot from the solution, e.g., via chromatography or column chromatography.

In some embodiments, the method of making triangular carbon quantum dots comprise: 1) dissolving phloroglucinol in ethanol to form a solution; 2) adding a conjugation catalyst, e.g., sulfuric acid, to the solution; 3) heating the solution at about 200° C. for about 2 hours; 4) cooling the solution to a lower temperature, e.g., room temperature and neutralizing the conjugation catalyst with a neutralizing agent, e.g., a base; and 5) isolating or purifying a triangular carbon quantum dot from the solution, e.g., via chromatography or column chromatography.

In other embodiments, the method of making triangular carbon quantum dots comprise: 1) dissolving phloroglucinol in ethanol to form a solution; 2) adding a conjugation catalyst, e.g., sulfuric acid, to the solution; 3) heating the solution at about 200° C. for about 5 hours; 4) cooling the solution to a lower temperature, e.g., room temperature and neutralizing the conjugation catalyst with a neutralizing agent, e.g., a base; and 5) isolating or purifying a triangular carbon quantum dot from the solution, e.g., via chromatography or column chromatography.

D. Articles of Manufacture

In some aspects, provided herein are articles of manufacture comprising the triangular carbon quantum dot described above.

The present article of manufacture can be configured for any suitable use. For example, the article of manufacture can be configured for imaging, sensing, catalytic, delivering, displaying, optronic, lighting, or computing applications. In some embodiments, the imaging application is a biological or chemical imaging application. In some embodiments, the sensing application is a biological or chemical sensing application. In some embodiments, the catalytic application is a biological, chemical, photo, or electro catalytic application. In some embodiments, the delivering application is a biological or chemical delivering application. In some embodiments, the delivering application is a drug delivering application.

In some embodiments, the article of manufacture is a polymer. In some embodiments, the article of manufacture is included in an imaging, a sensing, a catalytic, a delivering, a displaying, an optronic, a lighting, or a computing agent or device. In some embodiments, the article of manufacture is included in a photoelectric device, a transistor, a solar cell, a light emitting device, a light-emitting diode (LED), a diode laser, a qubit in quantum computing, a display, e.g., a television or a phone, a head-up display, e.g., a transparent head-up display, or a paint, e.g., a fluorescent paint or a luminescent paint.

E. Light-Emitting Diodes (LEDs)

Provided in other aspects are light-emitting diodes (LEDs) comprising the triangular carbon quantum dot described above. In some embodiments, the LED contains an active emission layer that contains a triangular carbon quantum dot of any of the embodiments described herein. In some embodiments, the LED contains an anode, a hole injection layer, an active emission layer, an electron transport layer and a cathode. In some embodiments, the hole injection layer, the active emission layer and the electron transport layer are placed between the anode and the cathode.

In some embodiments, the LED contains from one side to an opposite side, e.g., from the bottom up, an anode, a hole injection layer, an active emission layer, an electron transport layer and a cathode. In some embodiments, the LED contains a substrate that holds or supports an anode, a hole injection layer, an active emission layer, an electron transport layer and a cathode. In some embodiments, the substrate contains glass or a thermoplastic polymer, e.g., polyester or polyethylene terephthalate (PET). In some embodiments, the anode contains indium tin oxide (ITO) or graphene. In some embodiments, the substrate holds an anode to form a substrate anode. In some embodiments, the hole injection layer contains poly(3,4-ethylenedioxythiophene):poly(styrenesulfonate) (PEDOT:PSS), molybdenum oxide, e.g., $MoO_x$, X being 1-3, nickel oxide, e.g., $NiO_x$, X being 1-3, or vanadium(V) oxide, e.g., $VO_x$, X being 1-3. In some embodiments, the active emission layer contains a triangular carbon quantum dot:Y blended emission layer, Y being poly(N-vinyl carbazole) (PVK), poly-(N,N'-bis(4-butylphenyl)-N,N'-bis(phenyl) benzidine) (poly-TPD), or poly(9,9-dioctylfluorene) (PFO).

In some embodiments, the electron transport layer contains 1,3,5-tris(N-phenylbenzimidazol-2-yl) benzene (TPBI), zinc oxide (ZnO), titanium oxide, e.g., $TiO_x$, X being 1-2, or Tris(8-hydroxyquinolinato)aluminium ($Alq_3$). In some embodiments, the cathode contains Ca/Al, LiF/Al or Ag.

In some embodiments, the LED contains from one side to an opposite side, e.g., from the bottom up, a ITO glass substrate anode, a poly(3,4-ethylenedioxythiophene):poly(styrenesulfonate) (PEDOT:PSS) hole injection layer (HIL), an active triangular carbon quantum dot:PVK blended emission layer, a 1,3,5-tris(N-phenylbenzimidazol-2-yl) benzene (TPBI) electron transport layer (ETL), and a Ca/Al double-layered cathode.

In some embodiments, the LED has a maximum luminance from about 500 $cd/m^2$ to about 10,000 $cd/m^2$. For instance, in some embodiments, the LED has a maximum luminance from about 500 $cd/m^2$ to about 1000 $cd/m^2$, from about 500 $cd/m^2$ to about 2000 $cd/m^2$, from about 500 $cd/m^2$ to about 3000 $cd/m^2$, from about 500 $cd/m^2$ to about 4000 $cd/m^2$, from about 500 $cd/m^2$ to about 6000 $cd/m^2$, from about 500 $cd/m^2$ to about 8000 $cd/m^2$, from about 1000 $cd/m^2$ to about 2000 $cd/m^2$, from about 1000 $cd/m^2$ to about 3000 $cd/m^2$, from about 1000 $cd/m^2$ to about 4000 $cd/m^2$, from about 1000 $cd/m^2$ to about 6000 $cd/m^2$, from about 1000 $cd/m^2$ to about 8000 $cd/m^2$, from about 2000 $cd/m^2$ to about 3000 cd/m², from about 2000 cd/m² to about 4000 cd/m², from about 2000 cd/m² to about 6000 cd/m², from about 2000 cd/m² to about 8000 cd/m², from about 3000 cd/m² to about 4000 cd/m², from about 3000 cd/m² to about 6000 cd/m², from about 3000 cd/m² to about 8000 cd/m², from about 4000 cd/m² to about 6000 cd/m², from about 4000 cd/m² to about 8000 cd/m², from about 4000 cd/m² to about 10,000 cd/m², from about 6000 cd/m² to about 8000 cd/m², from about 6000 cd/m² to about 10,000 cd/m², or from about 8000 cd/m² to about 10,000 cd/m².

In some embodiments, the LED has a current efficiency from about 1 cd/A to about 10 cd/A. For instance, in some embodiments, the LED has a current efficiency from about 1 cd/A to about 2 cd/A, from about 1 cd/A to about 4 cd/A, from about 1 cd/A to about 6 cd/A, from about 1 cd/A to about 8 cd/A, from about 2 cd/A to about 4 cd/A, from about 2 cd/A to about 6 cd/A, from about 2 cd/A to about 8 cd/A, from about 2 cd/A to about 10 cd/A, from about 3 cd/A to about 4 cd/A, from about 3 cd/A to about 6 cd/A, from about 3 cd/A to about 8 cd/A, from about 3 cd/A to about 10 cd/A, from about 4 cd/A to about 6 cd/A, from about 4 cd/A to about 8 cd/A, from about 4 cd/A to about 10 cd/A, from about 5 cd/A to about 6 cd/A, from about 5 cd/A to about 8 cd/A, from about 5 cd/A to about 10 cd/A, from about 6 cd/A to about 8 cd/A, from about 6 cd/A to about 10 cd/A, from about 7 cd/A to about 8 cd/A, from about 7 cd/A to about 10 cd/A, from about 8 cd/A to about 10 cd/A, or from about 9 cd/A to about 10 cd/A.

In some embodiments, the LED of any of the embodiments described herein has a turn on voltage from about 2 V to about 5 V. For instance, in some embodiments, the LED has a turn on voltage from about 2 V to about 3 V, from about 2 V to about 4 V, from about 3 V to about 4 V, from about 3 V to about 5 V, or from about 4 V to about 5 V.

In some embodiments, the LED of any of the embodiments described herein has an emission range from about 460 nm to about 610 nm. For instance, in some embodiments, the LED has an emission range from about 460 nm to about 480 nm, from about 460 nm to about 500 nm, from about 460 nm to about 520 nm, from about 460 nm to about 540 nm, from about 460 nm to about 560 nm, from about 460 nm to about 580 nm, from about 460 nm to about 600 nm, from about 480 nm to about 500 nm, from about 480 nm to about 520 nm, from about 480 nm to about 540 nm, from about 480 nm to about 560 nm, from about 480 nm to about 580 nm, from about 480 nm to about 600 nm, from about 500 nm to about 520 nm, from about 500 nm to about 540 nm, from about 500 nm to about 560 nm, from about 500 nm to about 580 nm, from about 500 nm to about 600 nm, from about 520 nm to about 540 nm, from about 520 nm to about 560 nm, from about 520 nm to about 580 nm, from about 520 nm to about 600 nm, from about 540 nm to about 560 nm, from about 540 nm to about 580 nm, from about 540 nm to about 600 nm, from about 560 nm to about 580 nm, from about 560 nm to about 600 nm, or from about 580 nm to about 610 nm.

In some embodiments, the LED of any of the embodiments described herein has an emission range from about 460 nm to about 480 nm. In some embodiments of any of the LEDs described herein, the LED is a green LED and has an emission range from about 500 nm to about 520 nm. In some embodiments of any of the LEDs described herein, the LED is a yellow LED and has an emission range from about 530 nm to about 550 nm. In some embodiments of any of the LEDs described herein, the LED is a red LED and has an emission range from about 590 nm to about 610 nm. In some embodiments, the LED has a lifespan of at least about 10,000 hours. For instance, some embodiments, the LED has a lifespan of at least about 20,000 hours, at least about 30,000 hours, at least about 40,000 hours, at least about 50,000 hours, at least about 60,000 hours, at least about 70,000 hours, at least about 80,000 hours, at least about 90,000 hours, or at least about 100,000 hours.

F. Examples i. Overview

Carbon quantum dots (CQDs) have emerged as a promising material for optoelectronic applications on account of carbon's intrinsic merits of high stability, low cost, high abundance and environment-friendliness. However, it has been widely accepted that CQDs give broad emission and inferior color-purity with full width at half maximum (FWHM) commonly exceeding 80 nm, which fundamentally limits its application in display technology wherein high color-purity is a prerequisite. Here we first demonstrate high color-purity, narrow bandwidth (FWHM of 29 nm) and multicolored (from blue to red) emission from specially designed triangular CQDs (T-CQDs), with a quantum yield up to 72%. Detailed structural and optical characterizations together with elaborate theoretical calculations revealed that the unique triangular structure, molecular purity and the crystalline perfection of the T-CQDs surrounded by hydroxy groups are key to the high color-purity. Moreover, multicolored electroluminescent light-emitting diodes (LEDs) based on the narrow bandwidth emission T-CQDs (NBE-T-CQDs) displayed high color-purity (FWHM of 30 nm) as well as high-performance with a maximum luminance of 4762 cd/m² and current efficiency of 5.11 cd/A. Furthermore, such LEDs demonstrate outstanding stability. The triangular carbon quantum dots described herein can be used for developing high color-purity and high-performance NBE-T-CQDs-based LEDs ideal for the next-generation display technology. The following examples are offered to illustrate but not to limit the compositions, uses, and methods provided herein.

Herein, we report the first synthesis of novel triangular CQDs (T-CQDs), which demonstrate high color-purity, narrow bandwidth (FWHM of 29 nm) and multicolored (from blue to red) emission with a quantum yield up to 72%. The synthesis was conducted by judiciously choosing a three-fold symmetric phloroglucinol (PG) as the reagent (a triangulogen) together with a tri-molecular reaction route designed into the neighboring active —OH and —H groups for 6-membered ring cyclization, propagating to the target high color-purity narrow bandwidth emission T-CQDs (NBE-T-CQDs) (FIGS. 1a-e). The triangular structure and the narrow bandwidth emission of NBE-T-CQDs have been rigorously established, and their correlation manifest that the triangular structural rigidity dramatically reduces electron-phonon coupling, giving rise to the free-excitonic emission with negligible trap states. This has been borne out by elaborate theoretical calculations, which show highly delocalized charges and high structural stability of the T-CQDs. The multicolored LEDs based on the NBE-T-CQDs display high color-purity (FWHM of 30 nm) and high-performance with a maximum luminance ($L_{max}$) of 4762 cd/m² and current efficiency (TI) of 5.11 cd/A. Moreover, the LEDs demonstrate outstanding stability both on shelf and in operation.

Example 1: Synthesis and Optical Properties

Synthesis of High Color-Purity NBE-T-CQDs:

The highly tunable and high color-purity NBE-T-CQDs from blue to red were synthesized by solvothermal treatment of phloroglucinol (PG) dissolved in ethanol solution. In a typical preparation procedure for the synthesis of blue and green NBE-T-CQDs: PG (500 mg) was dissolved in ethanol (10 mL). The clear precursor solution after 10 minutes ultrasonic dissolving was then transferred to a poly(tetrafluoroethylene) (Teflon)-lined autoclave (25 mL) and heated at 200° C. for 9 and 24 h. After the reaction, the reactors were cooled to room temperature by water or naturally. The blue and green NBE-T-CQDs can be obtained through purification via silica column chromatography using a mixture of dichloromethane and methanol as the eluent. For yellow and red NBE-T-CQDs:PG (500 mg) was dissolved in ethanol (10 mL), followed by adding concentrated sulfuric acid (2 mL) as catalyst. The clear precursor solution was then transferred to a poly(tetrafluoroethylene) (Teflon)-lined autoclave (25 mL) and heated at 200° C. for 2 and 5 h. After the reaction, the reactors were cooled to room temperature by water or naturally, then the solution was diluted with ethanol, neutralized by sodium hydroxide and the supernatant was collected by centrifugation. Finally, the yellow and red NBE-T-CQDs can be obtained through purification via silica column chromatography using a mixture of dichloromethane and methanol as the eluent. The solvent ethanol for the synthesis of NBE-T-CQDs can also be changed to various other common solvents such as form amide, N,N-dimethyl formamide, water, and so on. In addition, refluxing of PG in high boiling point solvents such as formamide, N,N-dimethyl formamide at high temperature (150-220° C.) can also produce tunable fluorescent NBE-T-CQDs through optimization of reaction conditions.

Synthesis of the NBE-T-CQDs, as shown in FIG. 1a, involves the solvothermal treatment of three-fold symmetric PG triangulogen at 200° C. with different reaction time, followed by purifying via silica column chromatography using a mixture of dichloromethane and methanol as the eluent. The starting material PG triangulogen possesses a unique structure with three highly reactive hydrogen atoms at the three meta-positions activated by three electron-donating hydroxyl groups in a single molecule, which is a key point for the synthesis of the NBE-T-CQDs. For tuning their emission color, an appropriate amount of concentrated sulfuric acid was added as catalyst in the ethanol solution to control the size of NBE-T-CQDs (see Methods for more details). The typical aberration-corrected high-angle annular dark-field scanning transmission electron microscopy (HAADF-STEM) images of the NBE-T-CQDs (FIGS. 1b-e) clearly demonstrate the almost defect-free graphene crystalline structure with an obvious triangular shape. To the best of our knowledge, this is the first time that the exquisite aberration-corrected HAADF-STEM images of carbon materials were obtained. The bright multicolored emissions of blue (B), green (G), yellow (Y), and red (R) were observed from the NBE-T-CQDs solutions with gradually increasing sizes from 1.9 nm, to 2.4, 3.0, and 3.9 nm respectively (FIG. if), as expected by the quantum confinement effect[7,16-18]. Significantly, the tunable emission colors from blue to red could be observed even under daylight excitation (FIG. f), which is a clear signature of its strong emission properties. And the emission colors are brighter under UV light irradiation (excited at 365 nm, FIG. 1g).

Quantum Yield (QY) Measurements:

An absolute method, using Varian FLR025 spectrometer equipped with a 120 mm integrating sphere, was employed to determine the QY of NBE-T-CQDs. We conducted the test light from FLR025 spectrometer to the sphere. The QY was determined by the ratio between photons emitted and absorbed by NBE-T-CQDs. The ethanol solution was placed in a UV quarts cuvette with a light path of 10 mm to measure its QY, while the solvent ethanol filled in the quarts cuvette was used as a blank sample for the reference measurement. The spectral correction curve which relates to the sensitivity of the monochromator, detector, sphere coating and optics to wavelength was provided by Edinburgh Instruments.

Femtosecond Transient Absorption Setup:

A regeneratively amplified Ti:sapphire laser system (Coherent Libra, 50 fs, 1 kHz) provides the fundamental light source. The pump pulse (400 nm) is generated by focusing a portion of fundamental light into BBO crystal. In order to avoid the influence of rotational relaxation effects on dynamics, the polarization of pump pulse is randomized by depolarizing plate. The other fundamental pulse provides broadband probe pulse (white light continuum) that is produced by focusing 800 nm fundamental light into sapphire plate (3 mm). The pump and probe beams are overlapped in the sample with crossing areas of 600 μm and 150 μm. After passing through the sample, the probe pulse is focused into optical fiber that is coupled to spectrometer (AvaSpec-1650F). The energy of 400 nm excitation pulse is adjusted to about 1 μJ/pulse by a neutral density optical filter. The pump pulse is chopped at 500 Hz to acquire pumped (signal) and un-pumped (reference) probe spectra, and the ΔOD spectrum can be obtained by processing them. The solutions are placed in 2 mm optical path length quartz cuvette. Both the instrument response function (100 fs) and temporal chirp in the probe light are determined by measuring the cross modulation of solvent. The group velocity dispersion effect is corrected by home-made chirp program. For each measurement, the pump-probe delay scan is repeated three times to give the averaged experiment data.

Ultraviolet Photoelectron Spectroscopy Measurement:

UPS measurement was performed with an hv=21.22 eV, He I source (AXIS ULTRA DLD, Kratos). The analysis room vacuum was $3.0 \times 10^{-8}$ Torr, and the bias voltage for measurement was −9 V. The NBE-T-CQDs thin films were prepared from spin-coating on ITO substrates for UPS measurement.

Figure 6:
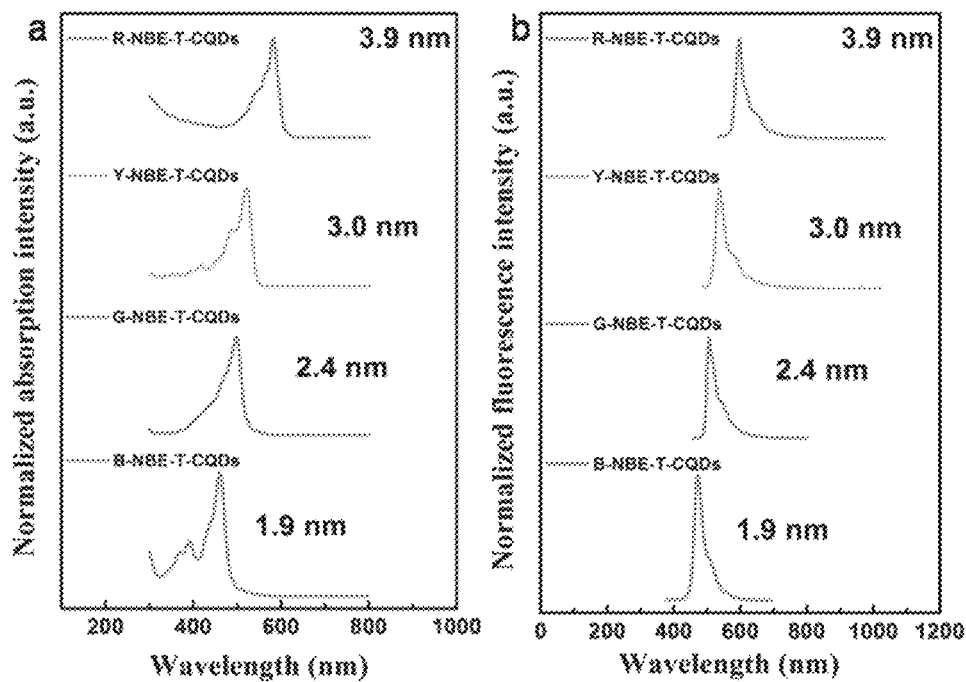
FIG. 6 shows the normalized UV-vis absorption (FIG. 6a) and PL (FIG. 6b) spectra of B-, G-, Y-, and R-NBE-T-CQDs.
Figure 7:
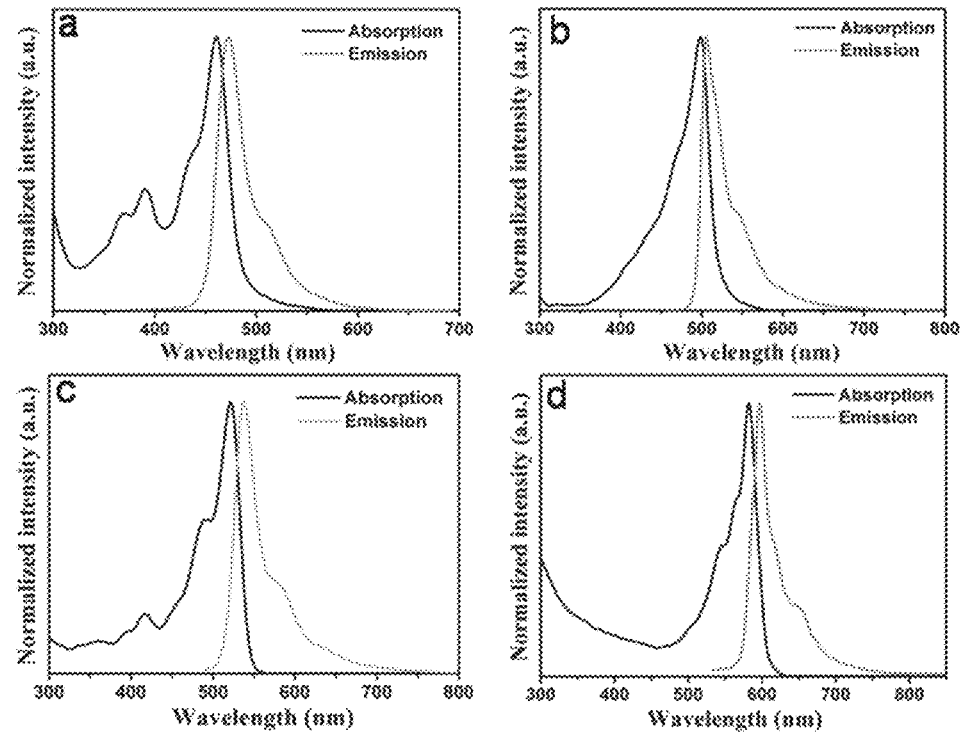
FIG. 7 shows the normalized UV-vis absorption and PL spectra of B- (a), G- (b), Y- (c), and R-NBE-T-CQDs (d).
Figure 8:
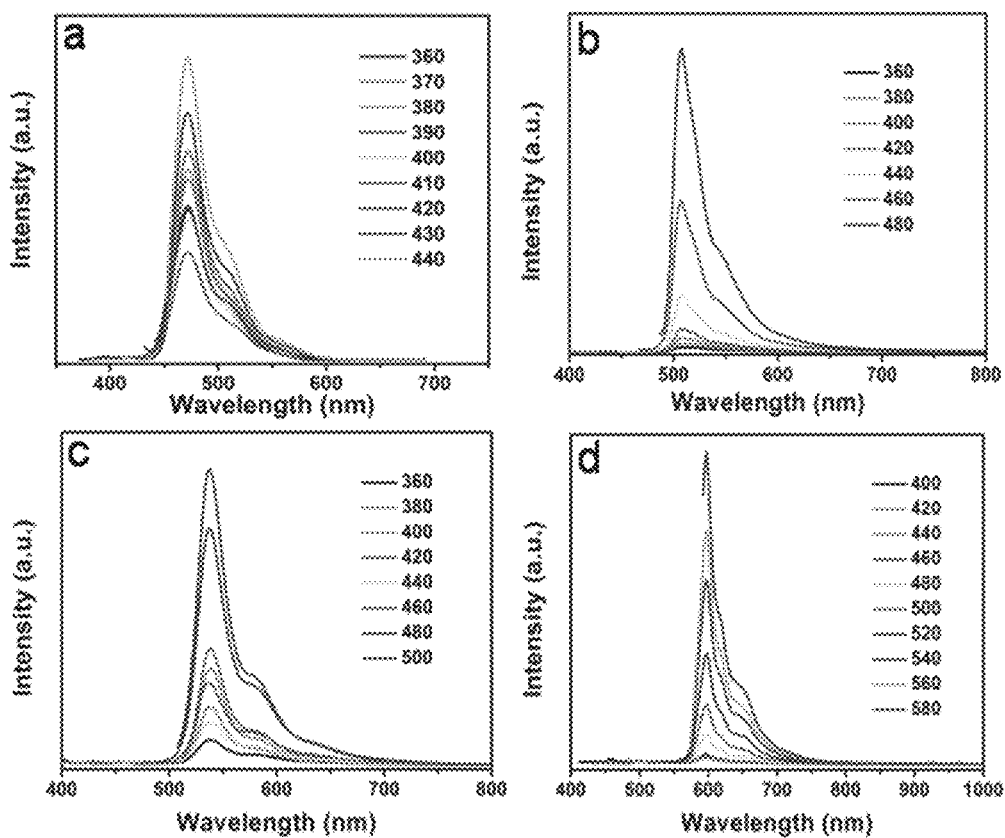
FIG. 8 shows the PL spectra of B- (a), G- (b), Y- (c), and R-NBE-T-CQDs (d) excited at different wavelengths.
Figure 9:
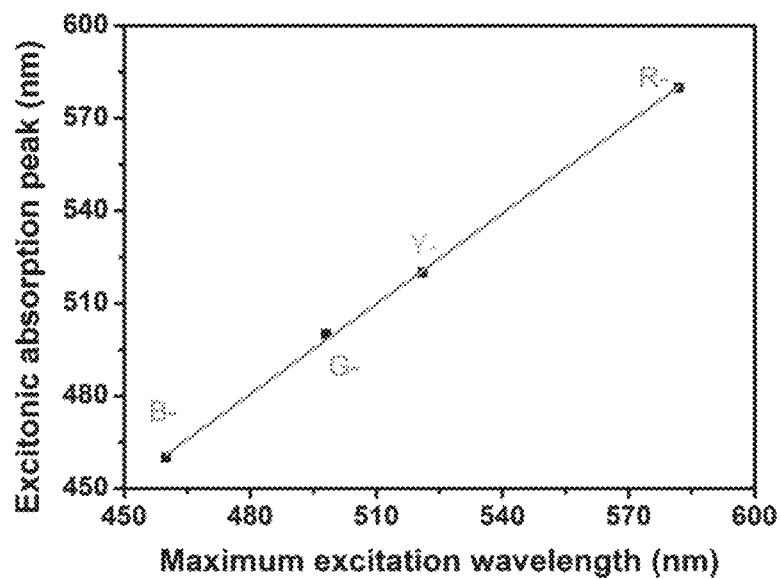
FIG. 9 shows the relationship between the maximum excitation wavelength of the PL emission and the corresponding excitonic absorption peak.
Figure 10:
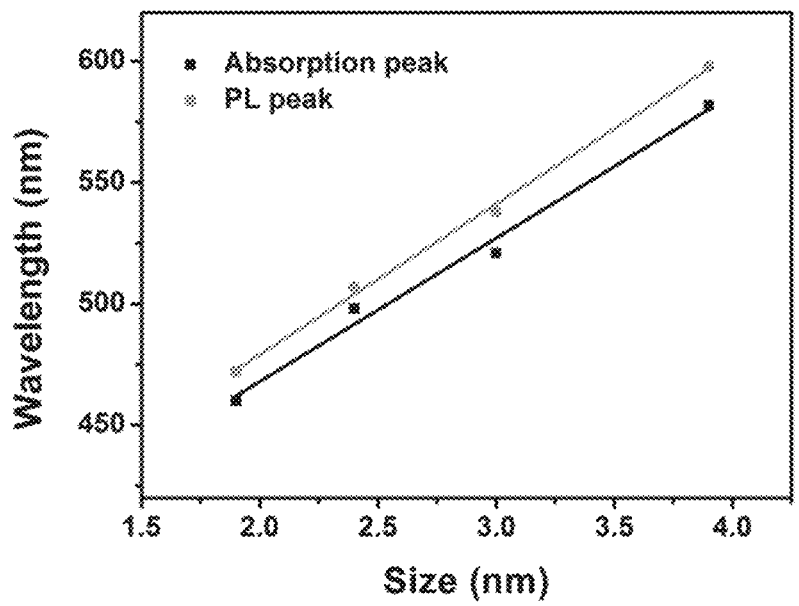
FIG. 10 shows the dependence of the PL and the first excitonic absorption peak wavelength on the size of NBE-T-CQDs.

The most important and distinctive features of the NBE-T-CQDs which set them apart from all other previous reported CQDs are the extremely narrow excitonic absorption and emission peaks. FIG. 1h shows the absorption spectra of the NBE-T-CQDs with strong and narrow excitonic absorption peaks centered at 460 (B-), 498 (G-), 521 (Y-) and 582 nm (R-NBE-T-CQDs), which is quite different from that of the previous reported CQDs with ultrabroad absorption bands[7-18,23,26]. The fluorescence spectra of NBE-T-CQDs (FIG. 1i) also show sharp excitonic emission peaks centered at 472 (B-), 507 (G-), 538 (Y-), and 598 nm (R-NBE-T-CQDs) with extremely narrow FWHM values of only 30, 29, 30, and 30 nm, respectively, which is far superior to previous reported CQDs with broadband fluorescence spectra (FWHM>80 nm) and even superior to the best $Cd^{2+}/Pb^{2+}$-based QDs (FWHM<40 nm)[7-18,23,26]. The weak shoulder emission peaks at longer wavelengths in the photoluminescence (PL) spectra may be ascribed to the excimer emission of the NBE-T-CQDs, which is often observed in highly delocalized polyaromatic systems.[34,35] Moreover, the NBE-T-CQDs also exhibit ultrasmall Stokes shifts of 12, 9, 17, and 16 nm for the B-, G-, Y-, and R-NBE-T-CQDs, respectively, (FIGS. 6-7), much smaller than those of the common CQDs (Stokes shifts>80 nm)[15-18], implying the band edge direct exciton recombination of the optical transitions as well as the weak electron-phonon coupling of the NBE-T-CQDs. The unusually narrow emission peaks of the NBE-T-CQDs are irrespective of the wide excitation wavelength range (FIG. 8) and the maximum excitation wavelength closely matches with the corresponding absorption peak wavelength (FIG. 9). These results further confirm that the PL emissions of the NBE-T-CQDs originate from direct exciton recombination. This is very different from the traditional CQDs whose excitation-dependent fluorescence is dominated by surface defects[15-18]. The gradually red-shifted excitonic emission peaks as well as the first excitonic absorption peaks are well consistent with the increased size of the NBE-T-CQDs (FIG. 10), a very clear characteristic of the bandgap transitions of the NBE-T-CQDs.

Figure 2:
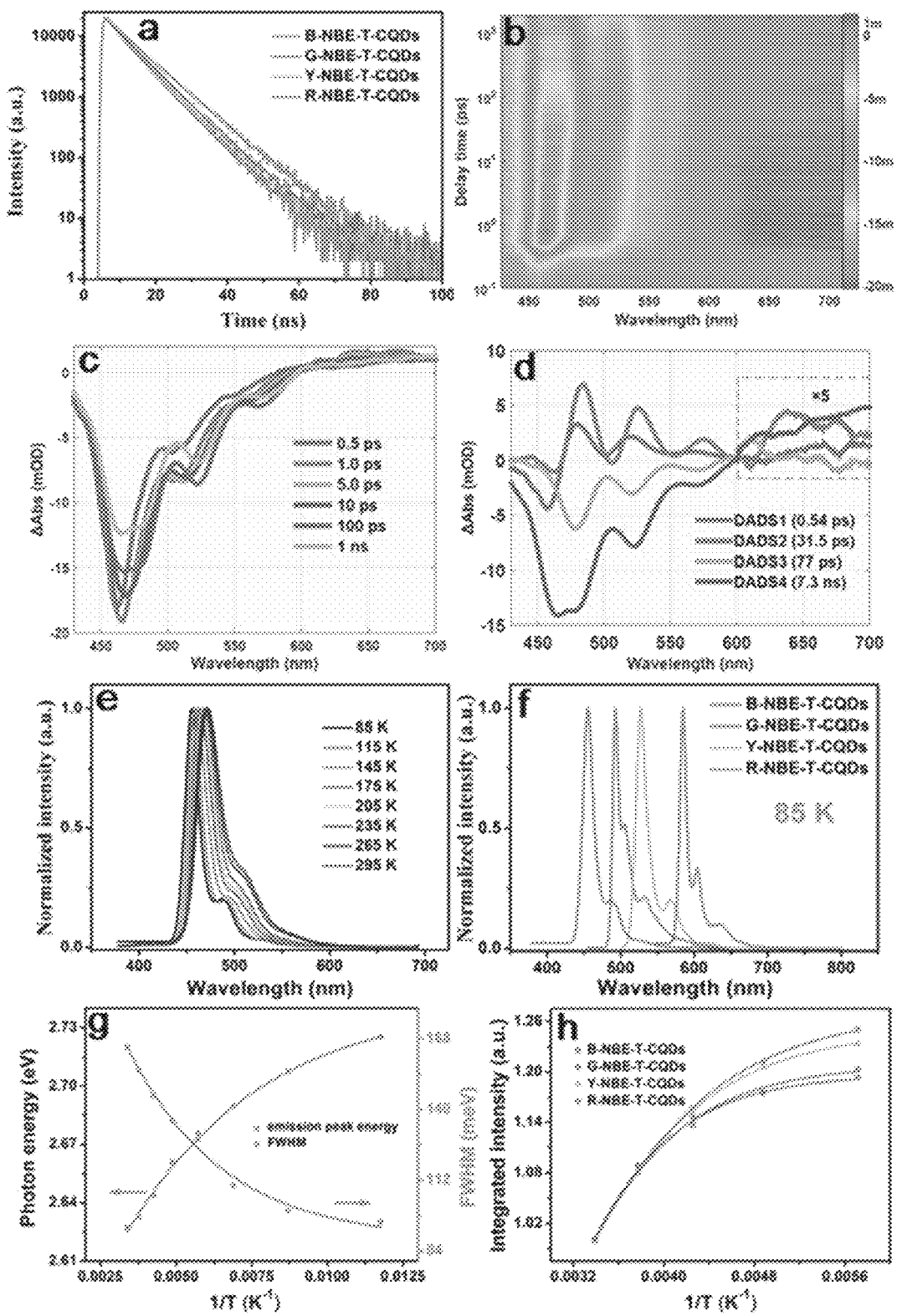
FIG. 2 shows the ultrafast dynamics of the photoexcited states and temperature-dependent PL spectra of the narrow bandwidth emission triangular carbon quantum dots(NBE-T-CQDs).
Figure 11:
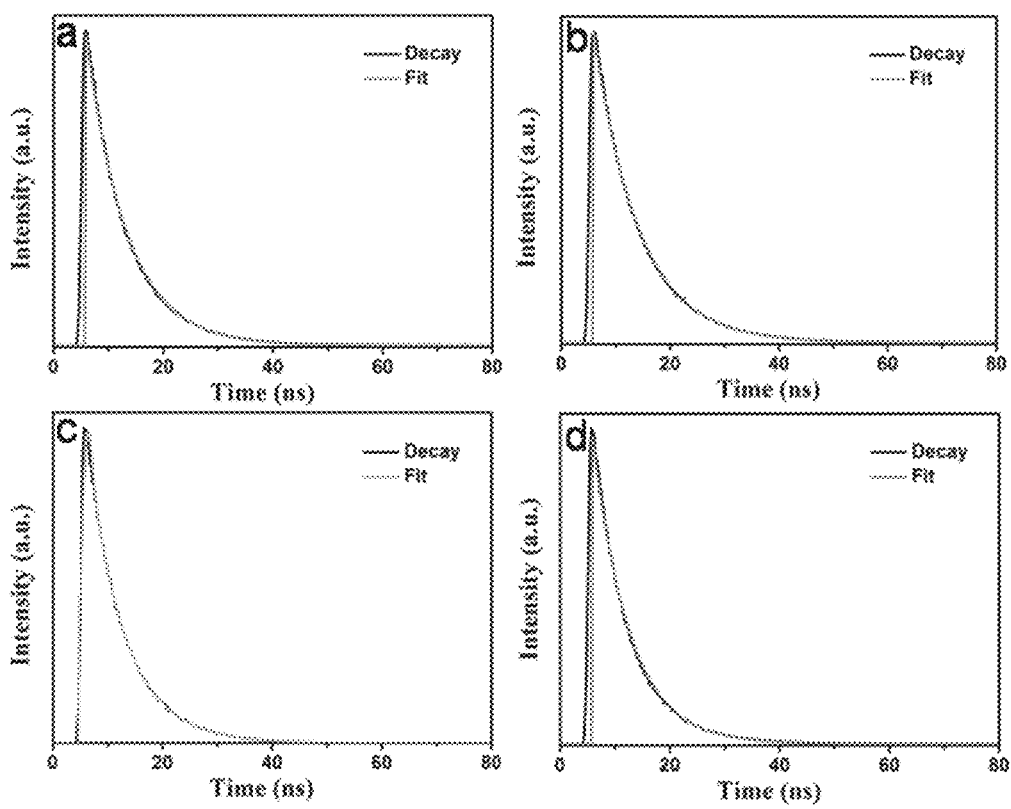
FIG. 11 shows the PL decay traces of B- (a), G- (b), Y- (c), and R-NBE-T-CQDs (d) excited at 460, 490, 520 and 580 nm with corresponding PL peaks at 472, 507, 538 and 598 nm respectively.
Figure 12:
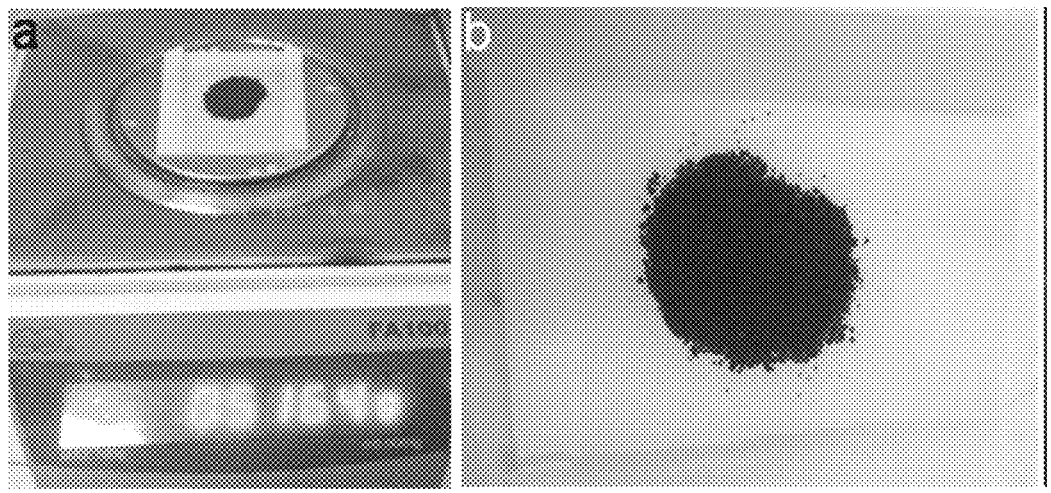
FIG. 12 shows the optical photographs of the G-NBE-T-CQDs powder (about 516 mg) under daylight obtained from large-scale solvothermal synthesis followed by purification via silica column chromatography.
Figure 13:
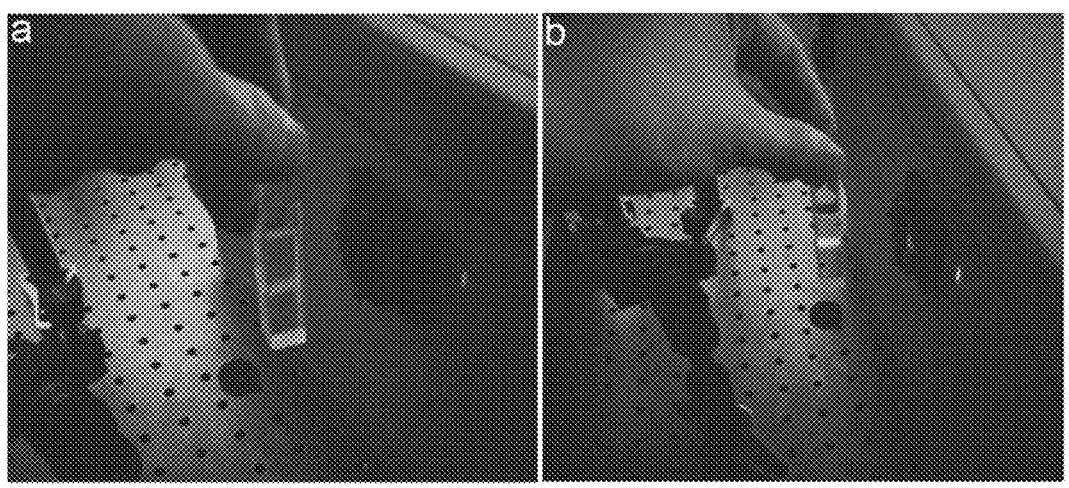
FIG. 13 shows the two-photon fluorescence images of diluted (a) and concentrated (b) G-NBE-T-CQDs ethanol solutions under 800 nm femtosecond laser excitation.
Figure 14:
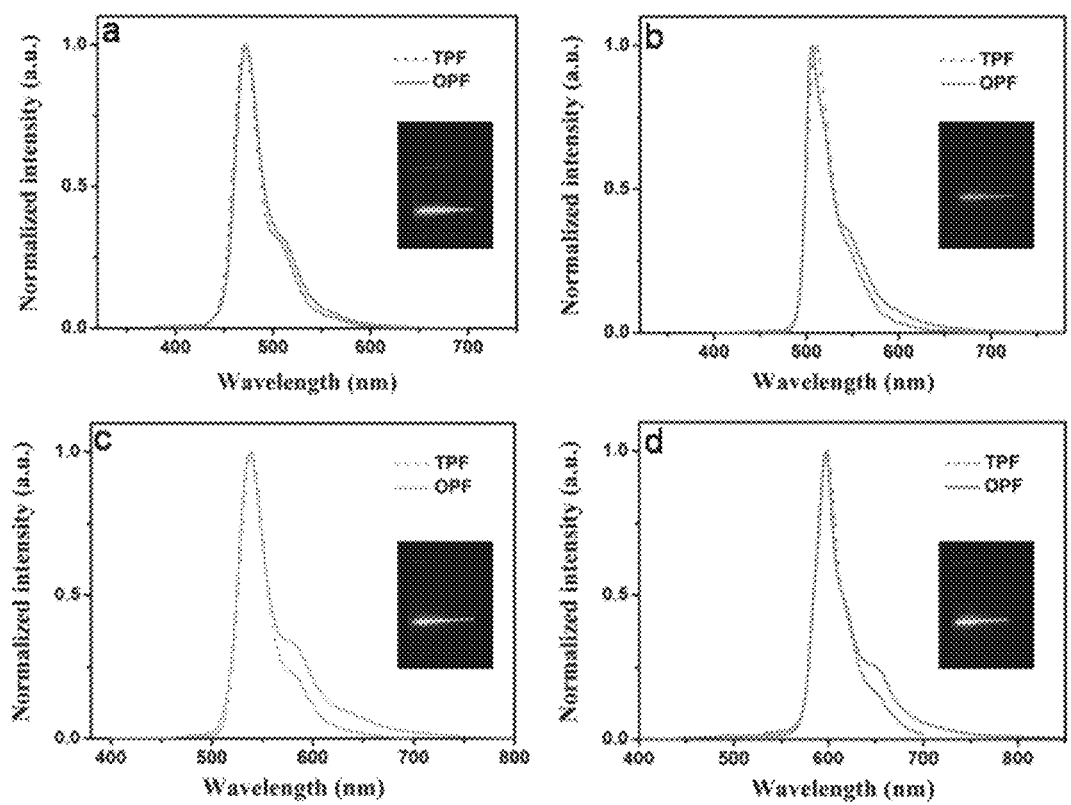
FIG. 14 shows the normalized one-photon fluorescence (OPF, solid line) and two-photon fluorescence (TPF, short dash line) spectra of B- (a), G- (b), Y- (c), and R-NBE-T-CQDs (d) under 880 nm femtosecond laser excitation. The insets are the TPF images from blue to red of NBE-T-CQDs under 880 nm femtosecond laser excitation.
Figure 15:
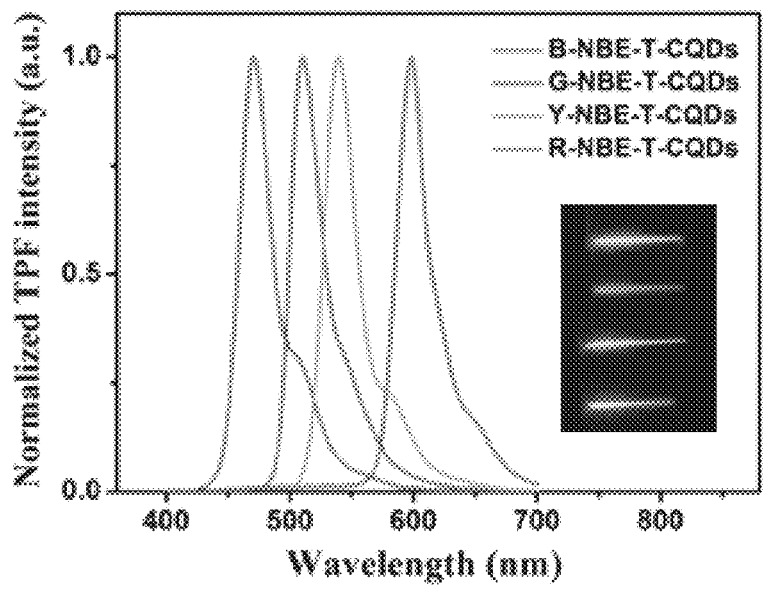
FIG. 15 shows the normalized TPF spectra of NBE-T-CQDs under 880 nm femtosecond laser excitation (Insets are the TPF images from blue to red).
Figure 16:
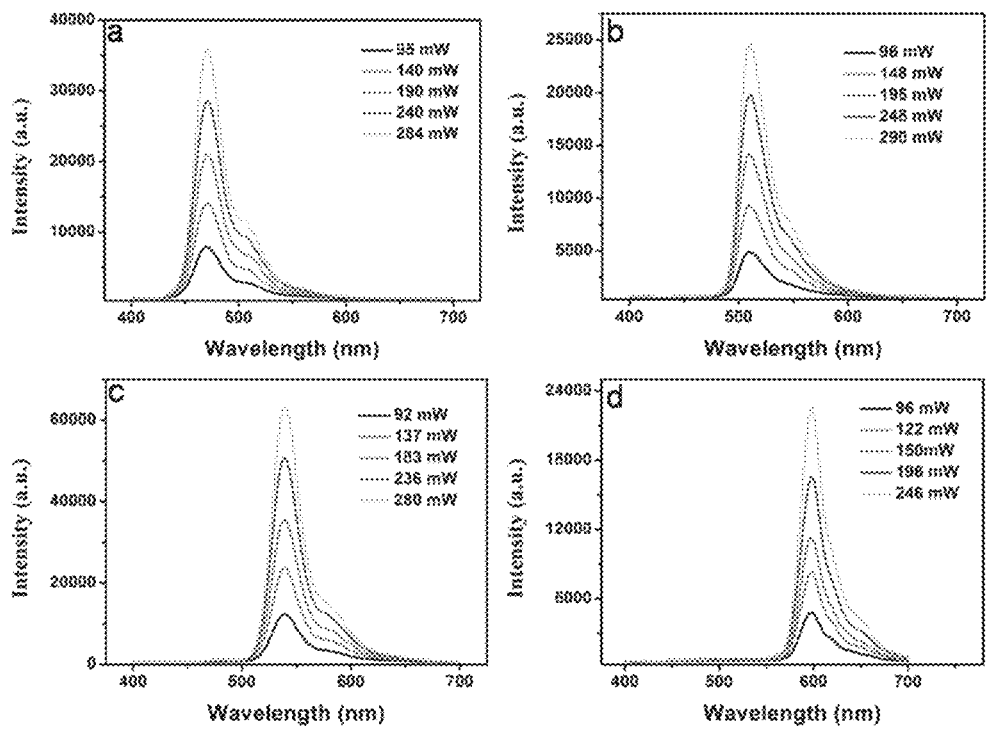
FIG. 16 shows the TPF spectra of B- (a), G- (b), Y- (c), and R-NBE-T-CQDs (d) under 880 nm femtosecond laser excitation with different laser powers.
Figure 17:
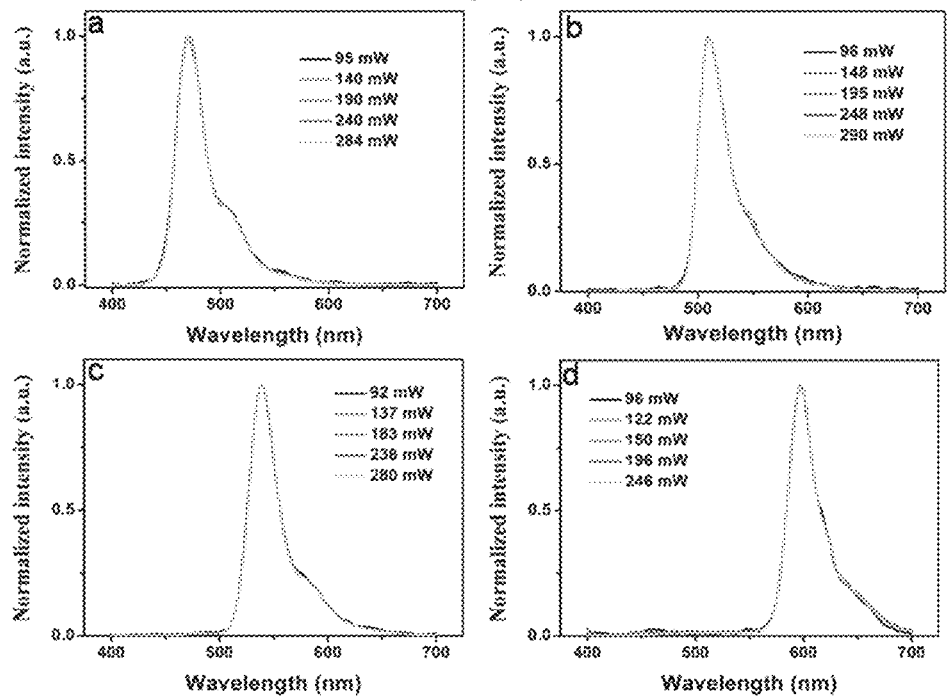
FIG. 17 shows the normalized TPF spectra of B- (a), G- (b), Y- (c), and R-NBE-T-CQDs (d) under 880 nm femtosecond laser excitation with different laser powers.
Figure 18:
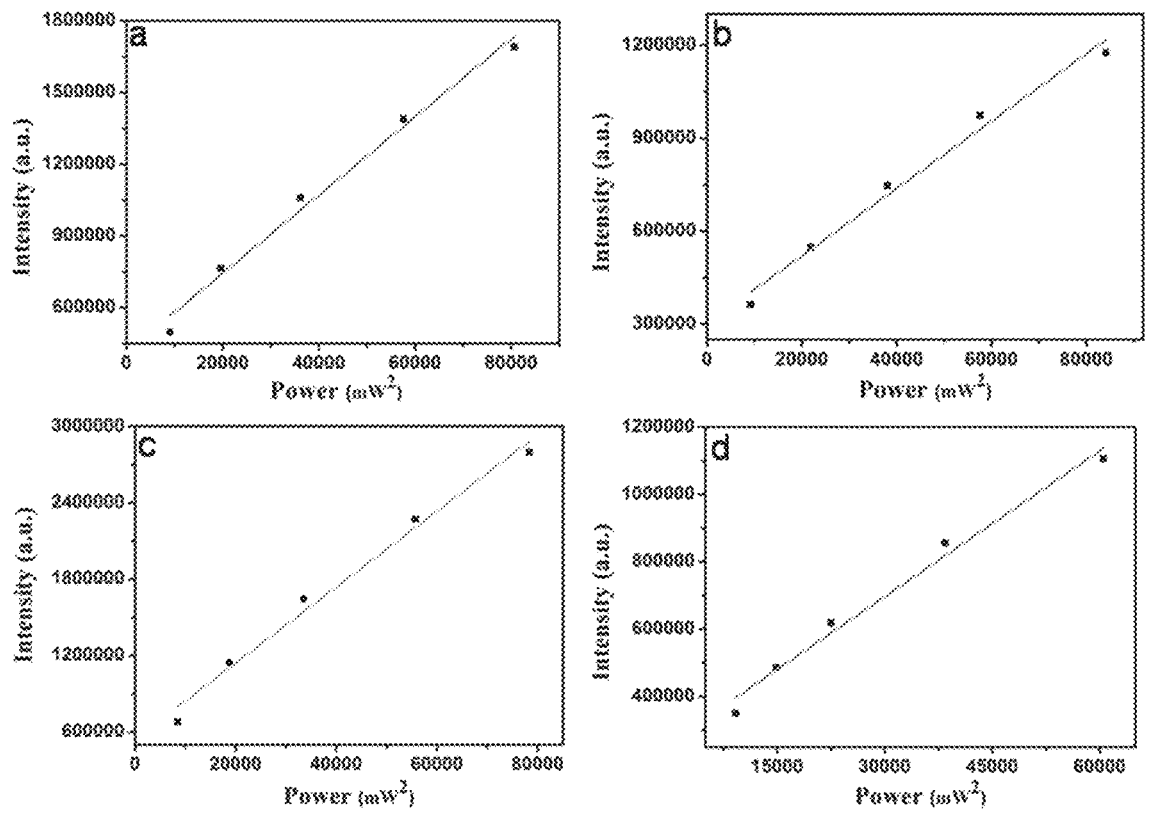
FIG. 18 shows the quadratic dependence of the integrated fluorescence intensity of B- (a), G- (b), Y- (c), and R-NBE-T-CQDs (d) under 880 nm femtosecond laser excitation on the laser power.

To gain more insight into the exciton recombination dynamics, time-resolved PL spectra were measured and the results are shown in FIG. 2a, which evidence monoexponential decay with fluorescence lifetimes of about 7.3, 8.3.7.0 and 6.6 ns for the B-, G-, Y-, and R-NBE-T-CQDs, respectively (FIG. 11). The monoexponential decay characteristics indicate that the excitons are highly stable and the radiative decay is extremely pure with a minimal nonradiative contribution[17,18], which is conducive to efficient fluorescence emission and again strikingly different from those reported CQDs with multi-exponential decay[10,30-33]. The absolute QY of the high color-purity NBE-T-CQDs was determined to be 66%, 72%, 62%, 54% for the B-, G-, Y-, and R-NBE-T-CQDs, respectively, which are among the highest values for CQDs reported to date. What is more, the NBE-T-CQDs also show the rarely seen strong high color-purity two-photon fluorescence (TPF) from blue to red (FWHM of 29 nm) (FIGS. 12-18), which may enable them to be used as excellent optical-gain media for high-performance frequency-up-conversion tunable lasers[36].

Figure 19:
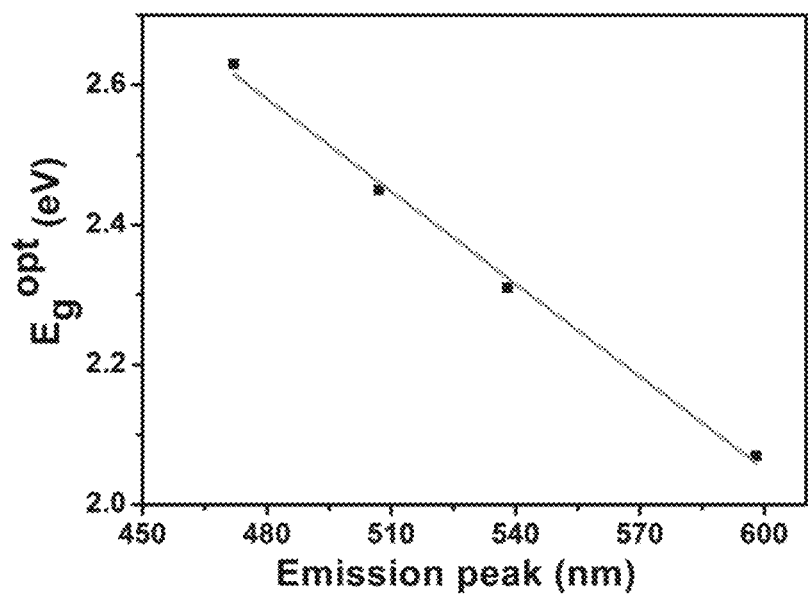
FIG. 19 shows the relationship between the bandgap energies and the corresponding excitonic emission peak wavelengths of NBE-T-CQDs.
Figure 20:
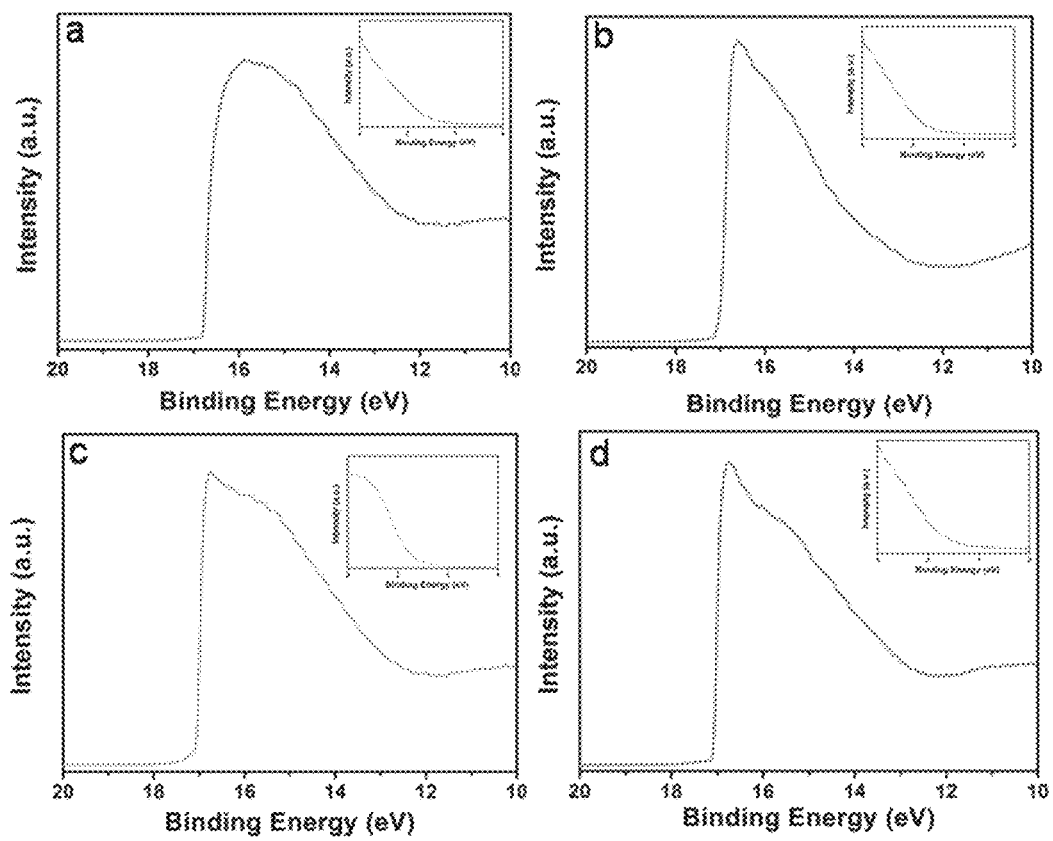
FIG. 20 shows the ultraviolet photoelectron spectroscopy (UPS) data of B- (a), G-(b), Y- (c), and R-NBE-T-CQDs (d).
Figure 21:
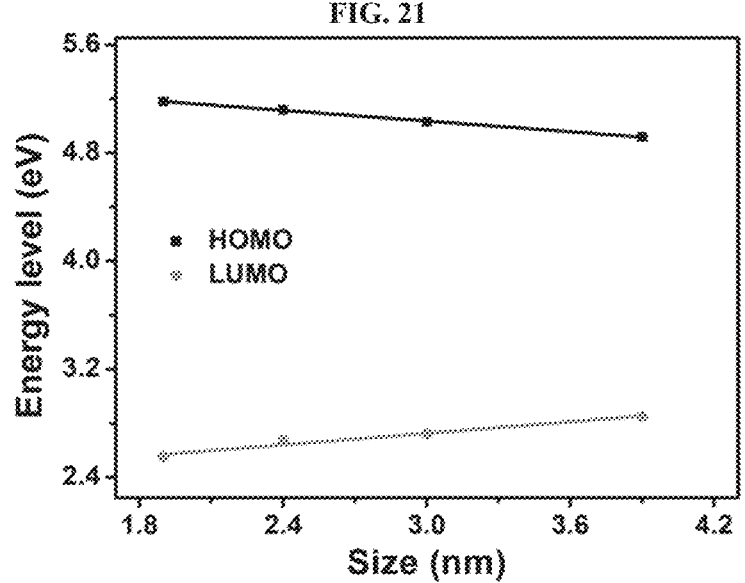
FIG. 21 shows the HOMO and LUMO energy levels as a function of the size of NBE-T-CQDs.
Figure 22:
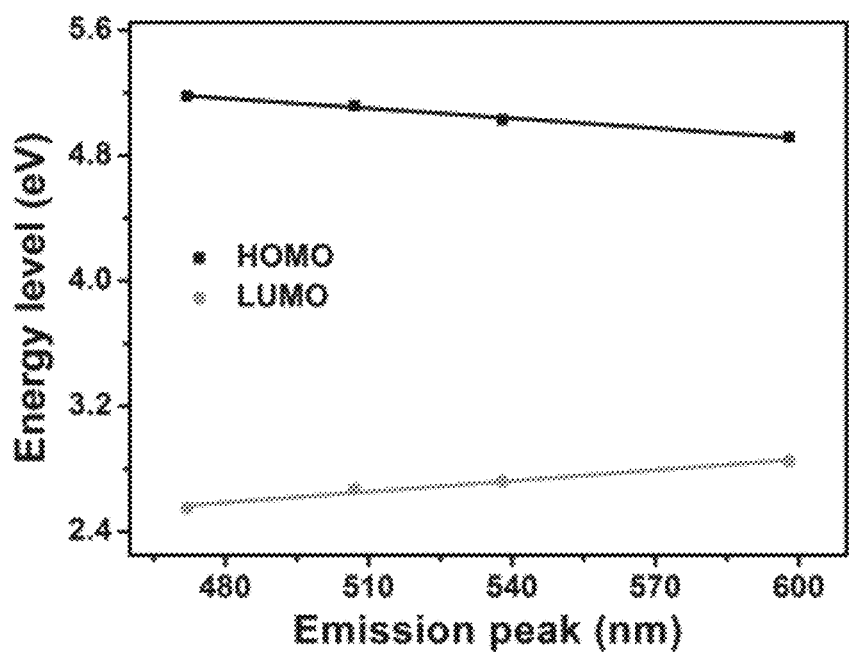
FIG. 22 shows the HOMO and LUMO energy levels as a function of the emission peaks of NBE-T-CQDs.

Bandgap energies of the NBE-T-CQDs were further calculated using the equation $E_g^{opt}=1240/\lambda_{edge}$, where $\lambda_{edge}$ is the onset value of the first excitonic absorption peaks in the direction of longer wavelengths. The calculated bandgap energies gradually decreased from 2.63 to 2.07 eV with the excitonic emission peak red-shifting from 472 to 598 nm and the size increasing from 1.9 to 3.9 nm (FIG. 19), further demonstrating the obvious size-dependent property of bandgap energies[18]. Meanwhile, the up-shifted highest occupied molecular orbital (HOMO) levels from −5.18 to −4.92 eV determined by means of ultraviolet photoelectron spectroscopy (UPS) and the down-shifted lowest unoccupied molecular orbital (LUMO) levels from −2.55 to −2.85 eV (FIGS. 20-22, Table 1) of the NBE-T-CQDs from blue to red directly reveal that the quantum confinement effect dominates the electronic and optical properties of the NBE-T-CQDs. Table 1 shows the estimation of the electron orbital energy levels of NBE-T-CQDs. Table 2 shows the calculated emission wavelength (nm), FWHM (nm), HOMO (eV), LUMO (eV) and band gap energies (eV) of the different kinds of model CQDs.

TABLE 1

| NBE-T-CQDs | HOMO (eV) | LUMO (eV) | $E_g^{opt}$ (eV) |
|---|---|---|---|
| B- | 5.18 | 2.55 | 2.63 |
| G- | 5.12 | 2.67 | 2.45 |
| Y- | 5.03 | 2.72 | 2.31 |
| R- | 4.92 | 2.85 | 2.07 |

TABLE 2

| | S—CQDs | | | T—CQDs | | | T—CQDs—OH | | | T—CQDs—COOH | | |
|---|---|---|---|---|---|---|---|---|---|---|---|---|
| | 1 | 2 | 3 | 1 | 2 | 3 | 1 | 2 | 3 | 1 | 2 | 3 |
| Em | 398 | 496 | 524 | 312 | 411 | 481 | 323 | 430 | 491 | 354 | 434 | 500 |
| FWHM | 85 | 132 | 149 | 52 | 74 | 77 | 48 | 62 | 64 | 68 | 103 | 135 |
| HOMO | 5.39 | 5.16 | 5.06 | 5.96 | 5.49 | 5.27 | 5.34 | 5.25 | 5.07 | 6.85 | 6.30 | 5.65 |
| LUMO | 1.95 | 2.25 | 2.40 | 1.38 | 1.75 | 2.19 | 1.26 | 1.72 | 2.11 | 2.98 | 2.88 | 2.78 |
| GAP | 3.44 | 2.91 | 2.66 | 4.58 | 3.74 | 3.08 | 4.08 | 3.53 | 2.96 | 3.87 | 3.42 | 2.87 |

Figure 23:
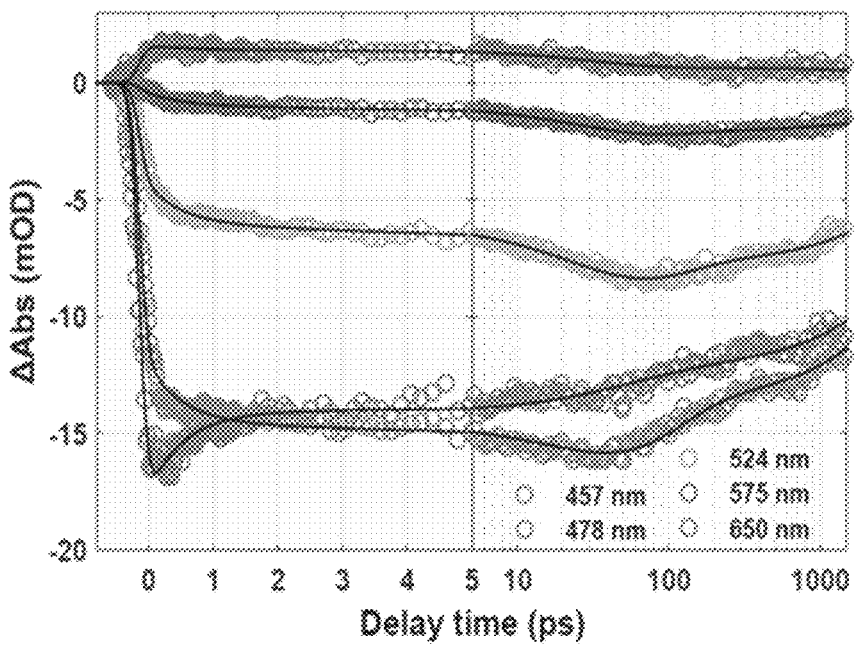
FIG. 23 shows the kinetic traces at different probe wavelengths.
Figure 24:
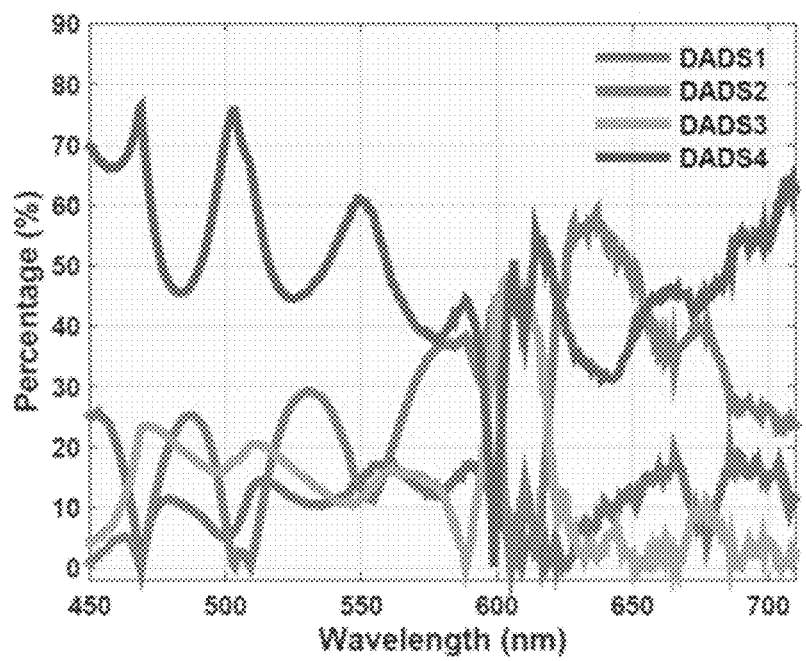
FIG. 24 shows the percentages of the four decay channels in the overall dynamics within the wavelength range constructed according to DADS in FIG. 2d.

To further scrutinize the bright and high color-purity excitonic emission of the NBE-T-CQDs from the perspective of transfer and recombination dynamics of the photogenerated charges, femtosecond transient absorption (fs-TA) spectroscopy measurement was carried out at 400 nm excitation. The TA spectra of B-NBE-T-CQDs are depicted in FIG. 2b in pseudo-3D with probe in the 430-710 nm range and scan delay time from 0.1 ps to 2 ns. The negative (blue) features from 430 to 550 nm correspond to the ground state bleaching (GSB) and stimulated emission (SE) according to the steady state absorption and PL spectra, and the relatively weaker positive (red) features from 600 to 710 nm correspond to the excited state absorption (ESA). The TA spectra at different time delays are shown in FIG. 2c. The negative peaks of SE centered at 466 and 524 nm gradually increase in the first picosecond. The kinetic traces at different wavelengths as a function of delay time are also presented in FIG. 23. To unravel the detailed relaxation channels of the excited carriers of B-NBE-T-CQDs, global analyses were performed on the TA data, and four distinctive decay components were derived. The four fitted lifetimes of carriers are 0.54±0.01 ps, 31.5±0.8 ps, 77±2 ps and 7.3±0.08 ns, respectively. The fitted decay associated difference spectra (DADS) are shown in FIG. 2d. It can be observed that during the first lifetime, the GSB decays accompanied by the rise of SE, then the signal of SE continues to increase within the second lifetime, but in the third and fourth lifetime, the SE signal decays. The weaker DADS at around ESA were enlarged to reveal more clearly the changes of different components. In order to analyze the four different carrier relaxation channels, the DADS at different wavelengths are normalized to evaluate the proportion of the decay dynamics (FIG. 24). Different regions with distinct relaxation dynamics can be clearly observed as follows: (1) the percentage of both the first and second component is zero at ~468 nm; (2) the percentage of the second component at ~506 and ~605 nm is zero; (3) the percentage of the fourth component at ~598 nm is zero; (4) the percentage of the third component at ~590 nm and from 632 to 700 nm are zero. On the basis of the different regions and DADS, we can ascribe the four components to the corresponding relaxation channels. Since the pump (400 nm) is higher in energy than the bandgap of B-NBE-T-CQDs, the excited carriers in the sp² cluster have excess energy after excitation, and will experience Coulomb-induced thermalization within the first few tens of femtoseconds, which is shorter than our instrumental response time (~100 fs)[37]. The hot carriers will release the excess energy into the surrounding environment via optical phonon scattering (0.54 ps)[38] and acoustic phonon scattering (31.5 ps)[39]. Part of the cooled carriers, whose dynamics is distributed at ~598 nm, will experience nonradiative transition into the ground state within 77 ps. The remaining part will emit fluorescence (7.3 ns) via recombination of electrons and holes, and the ESA of this part is mainly distributed at 590 nm and 632-700 nm. Intriguingly, the strong emission of the NBE-T-CQDs is directly demonstrated here by the much higher amplitude of emissive component than that of nonradiative decay component, with the latter accounting for only a small percentage of about 15-20% (FIG. 2d, FIG. 24). Furthermore, contrary to the complex nonradiative excited-state relaxation processes commonly responsible for the broadening of PL peaks, the quite simple excited state relaxation channels we obtained from the TA spectra naturally explain the high color-purity excitonic emission of NBE-T-CQDs[40,41].

Figure 25:
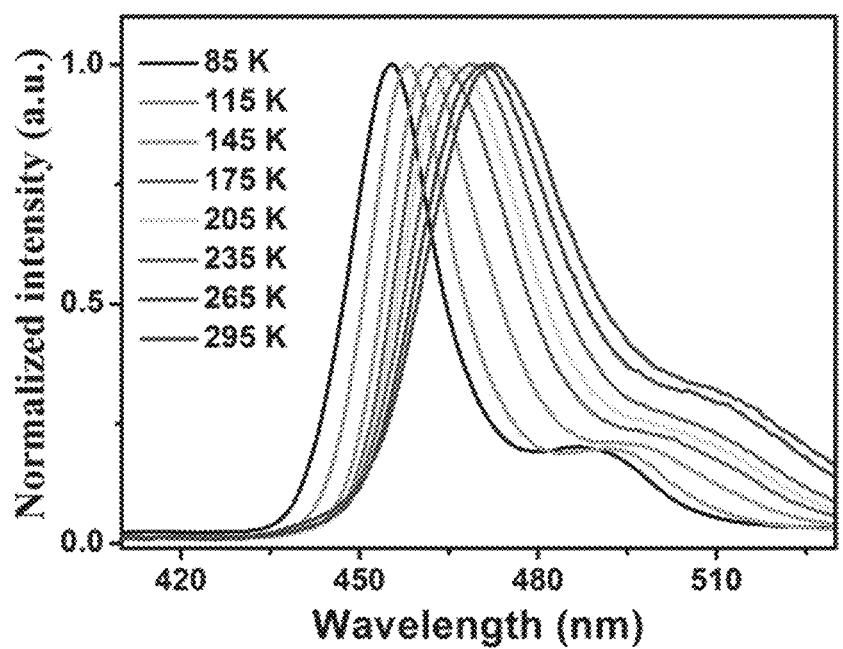
FIG. 25 shows the temperature-dependent PL spectra of B-NBE-T-CQDs (85-295 K) excited at 400 nm.
Figure 26:
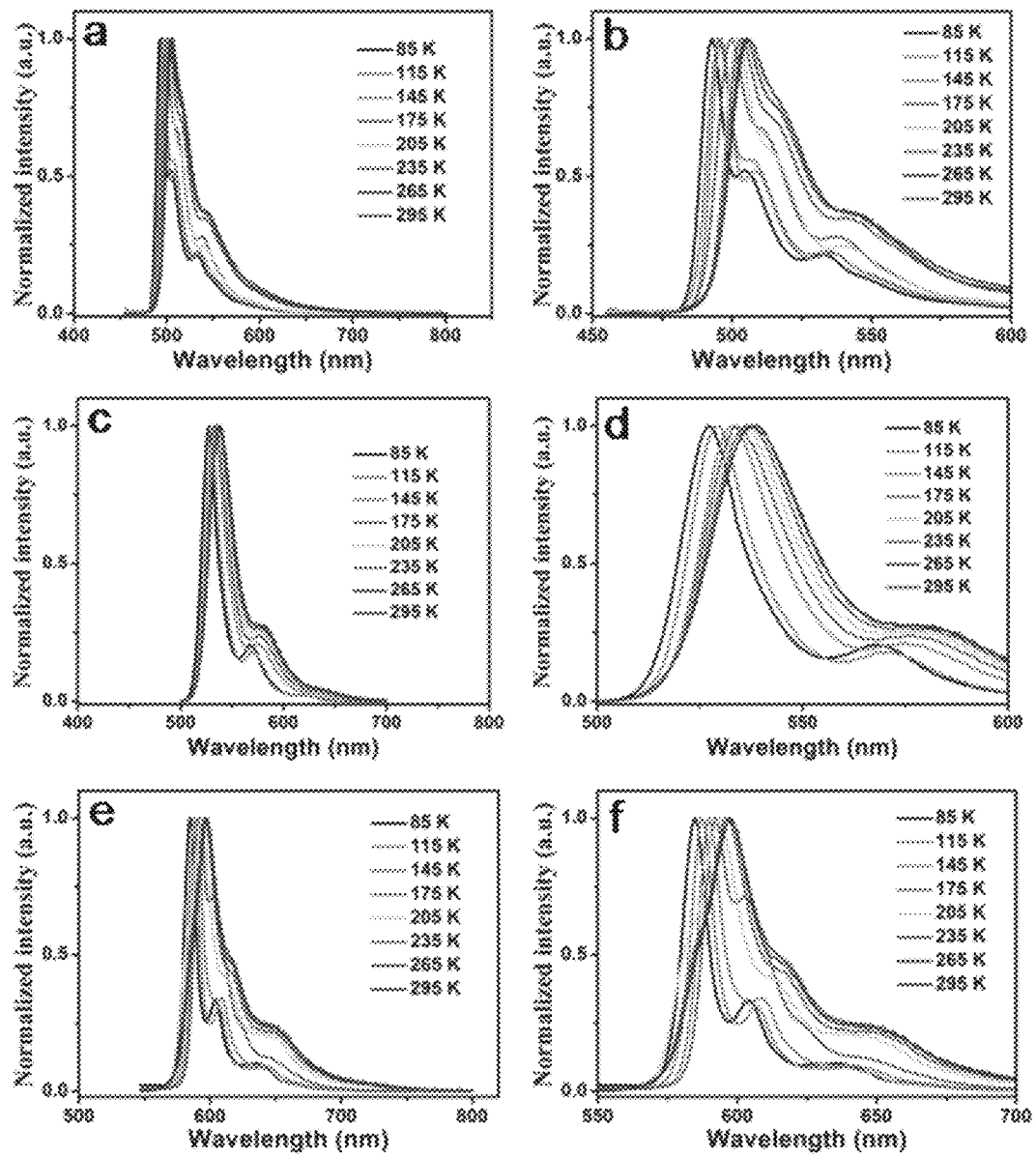
FIG. 26 shows the temperature-dependent PL spectra of G- (a, b), Y- (c, d), and R-NBE-T-CQDs (e, f) (85-295 K).
Figure 27:
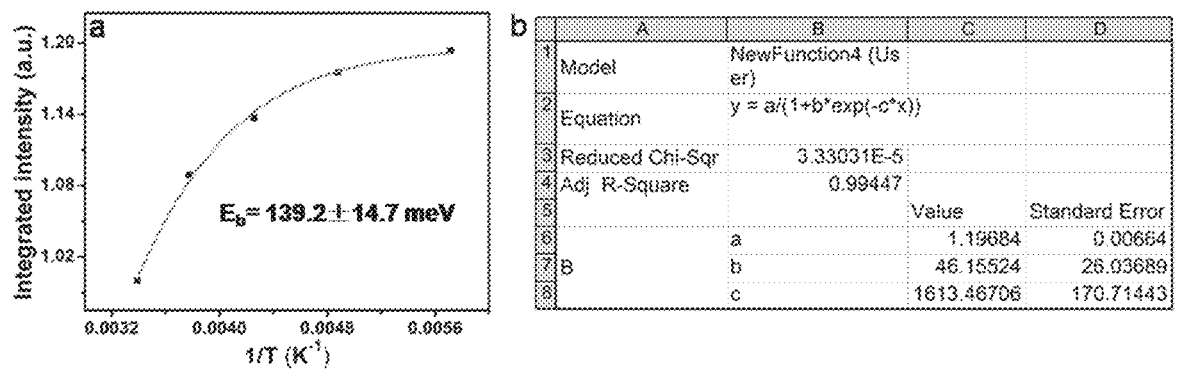
FIG. 27 shows the plots of integrated PL emission intensity of B-NBE-T-CQDs as a function of temperature (175-295 K) (a) and the corresponding fitting parameters (b).
Figure 28:
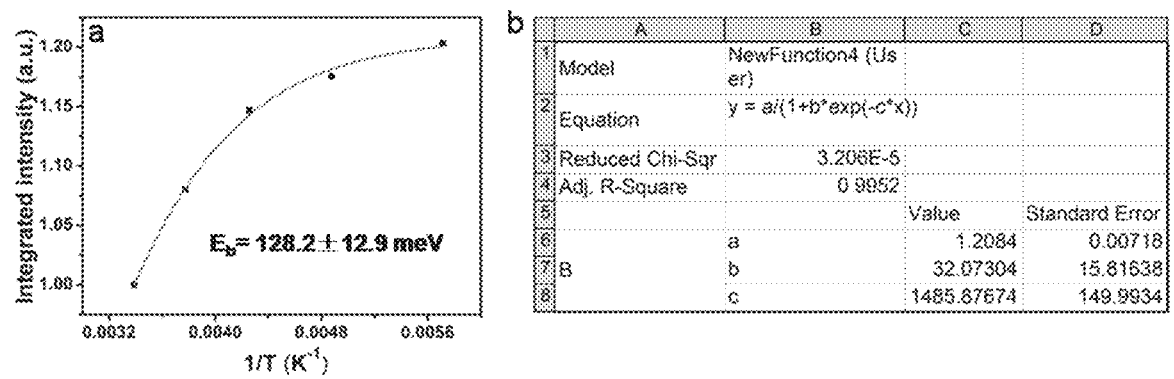
FIG. 28 shows the plots of integrated PL emission intensity of G-NBE-T-CQDs as a function of temperature (175-295 K) (a) and the corresponding fitting parameters (b).
Figure 29:
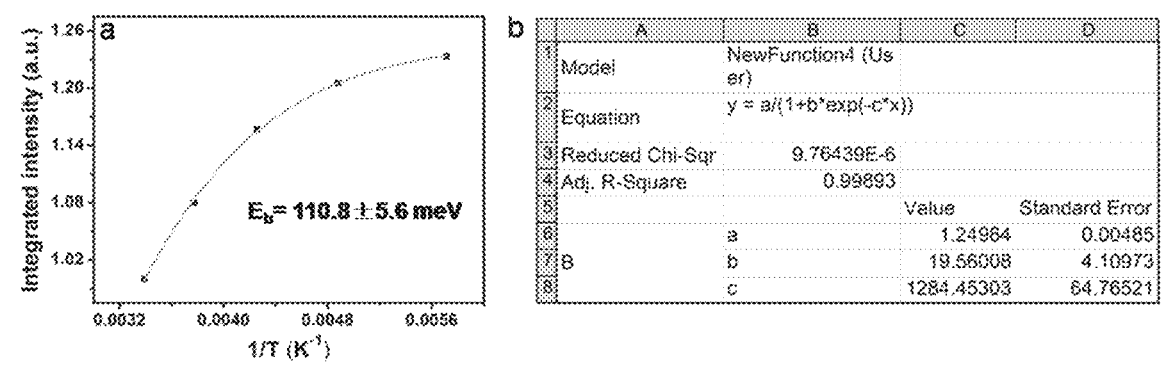
FIG. 29 shows the plots of integrated PL emission intensity of Y-NBE-T-CQDs as a function of temperature (175-295 K) (a) and the corresponding fitting parameters (b).
Figure 30:
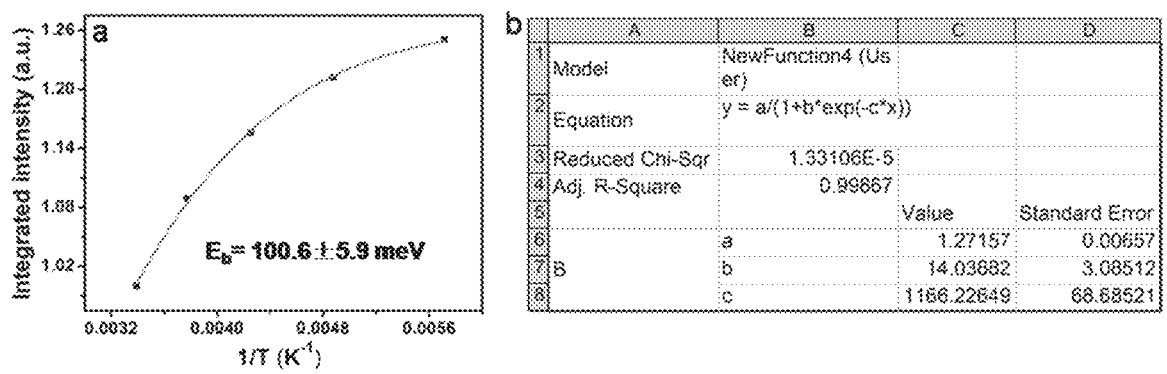
FIG. 30 shows the plots of integrated PL emission intensity of R-NBE-T-CQDs as a function of temperature (175-295 K) (a) and the corresponding fitting parameters (b).

To acquire more intrinsic characteristics of the photogenerated excitons in the high color-purity NBE-T-CQDs, temperature-dependent PL spectra were also recorded, and the resulting emission narrowing was analysed, as has long been used to assess mechanisms of electron-phonon coupling in a wide range of bandgap emitting inorganic QDs[42,43]. As temperature was decreased from 295 to 85 K, all the PL peaks of the NBE-T-CQDs show continuous narrowing and blue-shift (FIG. 2e, FIGS. 25-26). Remarkably, the PL spectra acquired at 85 K exhibit extremely narrow FWHM of 16, 11, 16 and 9 nm for the B-, G-, Y-, and R-NBE-T-CQDs, respectively (FIG. 2f), indicating that the narrow emission is attributable to the lowest state free-excitonic emission with negligible trap states. As shown in FIG. 2g, the FWHM reduces from 164.7 (30 nm) to 95.4 meV (16 nm) and the emission peak energy of the B-NBE-T-CQDs shifts towards higher energy from 2.627 to 2.725 eV with decreasing temperature from 295 to 85 K. The narrowed FWHM and blue-shifted emission peaks of the NBE-T-CQDs with decreasing temperature are well described by traditional empirical Varshni models, which can be explained by the reduced electron-phonon coupling due to the restricted structural vibrations and distortions at the lower temperatures[42-44]. It has been demonstrated that the electron-phonon coupling resulting from structural vibrations and distortions plays a dominating role in determining the FWHM of the PL spectra of inorganic QDs[42,43]. Therefore, it is reasonable to conclude that the dramatically reduced electron-phonon coupling demonstrated by the temperature-dependent PL spectra leads to the high color-purity, free-excitonic emission of the NBE-T-CQDs.

Figure 31:
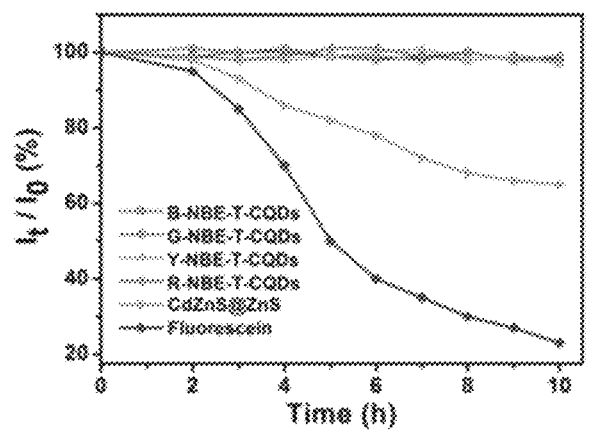
FIG. 31 shows the photostability comparison between NBE-T-CQDs and conventional core-shell semiconductor QDs such as CdZnS@ZnS and organic dyes such as fluorescein under continuous radiation with a UV lamp for 10 h.

Apart from the temperature-dependent PL peak wavelengths and FWHM, the integrated PL intensity of NBE-T-CQDs shows a slight decrease with increasing temperature (FIG. 2h), which can be ascribed to thermally activated exciton dissociation and nonradiative trapping[45]. Importantly, the thermal quenching of the integrated PL intensity of the NBE-T-CQDs with increasing temperature from 175 to 295 K is less than 20%, indicating the high thermostability and the minimal nonradiative recombination centers or defects. To extract the important physical parameter of exciton binding energy, we plot in FIG. 2h the integrated PL emission intensity as a function of temperature (175-295 K). The curves can be fitted using the following equation:

$$I(T) = \frac{I_0}{1 + Ae^{-E_b/k_B T}}$$

where $I_0$ is the intensity at 0 K, $E_b$ is the exciton binding energy, and $k_B$ is the Boltzmann constant. From the fitting analysis, the NBE-T-CQDs have a relatively large exciton binding energy of 139.2, 128.2, 110.8, 100.6 meV for the B-, G-, Y-, and R-NBE-T-CQDs, respectively (FIGS. 27-30), which is even larger than those of many inorganic QDs and thus contributes to the high color-purity of the NBE-T-CQDs[46]. To the best of our knowledge, this is the first time that the important physical parameters of exciton binding energy are obtained for the CQDs. Moreover, besides the high thermostability concluded from the temperature-dependent PL spectra, the NBE-T-CQDs also showed more robust photostability than the best protected core-shell inorganic QDs such as CdZnS@ZnS and organic dyes such as fluorescein under continuous radiation of a UV lamp for 10 h (FIG. 31), giving them more competitive edges for LED applications.

Example 2: Structural Characterizations

Characterization Method:
A JEOL JEM 2100 transmission electron microscope (TEM) was used to investigate the morphologies of the NBE-T-CQDs. X-ray diffraction (XRD) patterns were carried out by an X-ray diffraction using Cu-Ka radiation (XRD, PANalytical X'Pert Pro MPD). Absorption spectra were recorded on UV-2450 spectrophotometry. The fluorescence spectra of NBE-T-CQDs were measured on a PerkinElmer-LS55 luminescence spectrometer with slit width at 2.5-2.5 nm. The photographs were taken with camera (Nikon, D7200) under UV light excited at 365 nm (UV light: SPECTROLINE, ENF-280C/FBE, 8W). The FT-IR spectra were measured using a Nicolet 380 spectrograph. X-ray photoelectron spectroscopy (XPS) was performed with an ESCALab220i-XL electron spectrometer from VG Scientific using 300 W Al Ka radiation. The Raman spectrum was measured using Laser Confocal Micro-Raman Spectroscopy (LabRAM Aramis). Low-temperature-dependent PL spectra measurements were performed in the temperature range of 85-295 K using a liquid nitrogen cooler. The TPF spectra of NBE-T-CQDs ethanol solution placed in the 1 cm fluorescence cuvette were recorded on the fiber spectrometer (Ocean Optics USB2000 CCD) with a Ti:sapphire femtosecond laser (Spitfire. Spectra-Physics, 100 fs. 80 MHz, 880 nm) for excitation.

STEM-HAADF Images Characterization:
A JEM-ARM200F transmission electron microscope (TEM) was used to investigate the STEM-HAADF images of the NBE-T-CQDs. Ultrathin carbon film supported by a lacey on a 400 mesh copper grid (product No. 01824, bought from Beijing Xinxing Braim Technology Co., Ltd) was used to disperse the NBE-T-CQDs. The purified diluted NBE-T-CQDs ethanol solution with 5 microlitre was dropped on the surface of ultrathin carbon film, and then dried at room temperature. Finally, the STEM-HAADF images of NBE-T-CQDs samples were measured at 200 KV.

Figure 3:
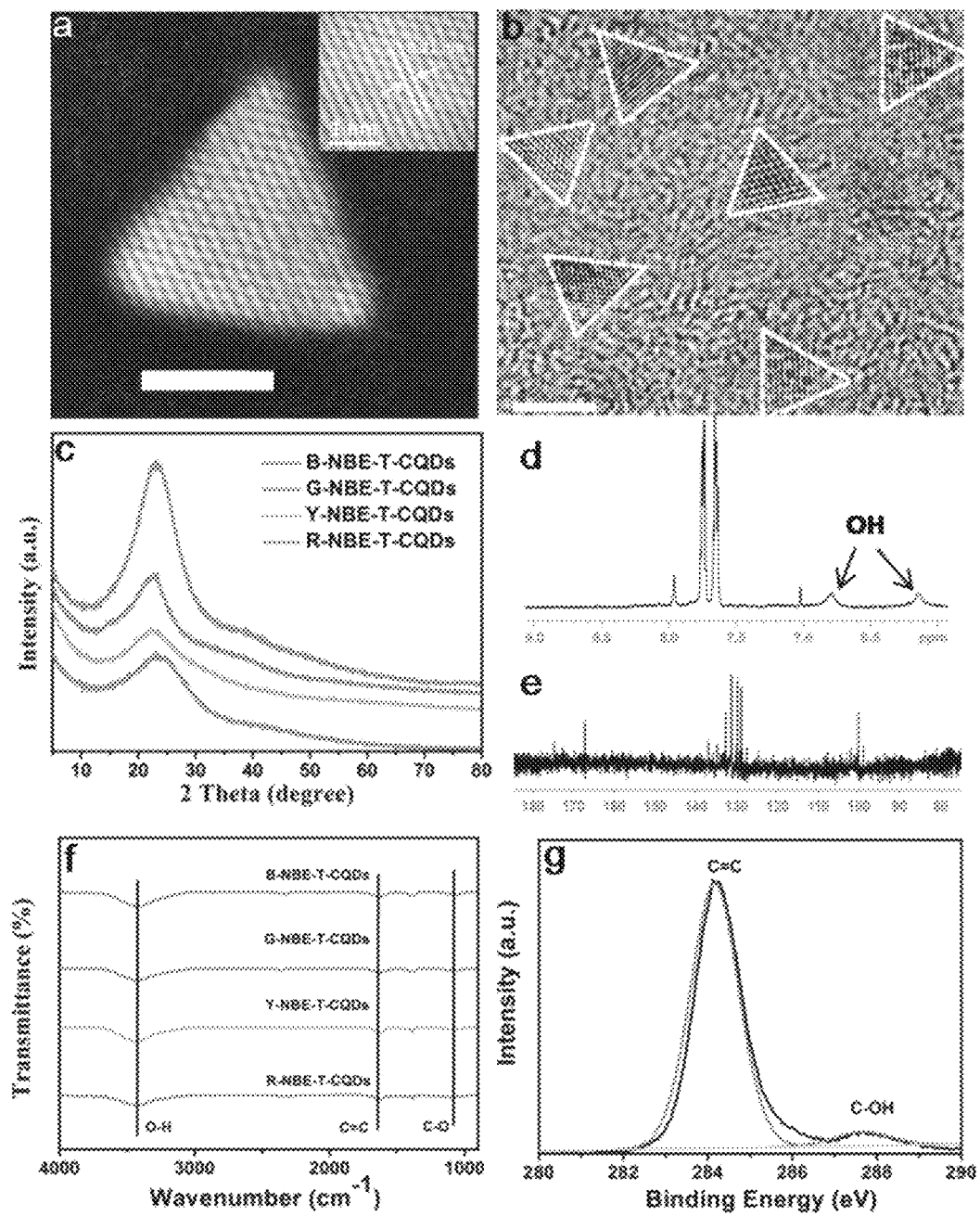
FIG. 3 shows the structural characterizations of the NBE-T-CQDs.
Figure 32:
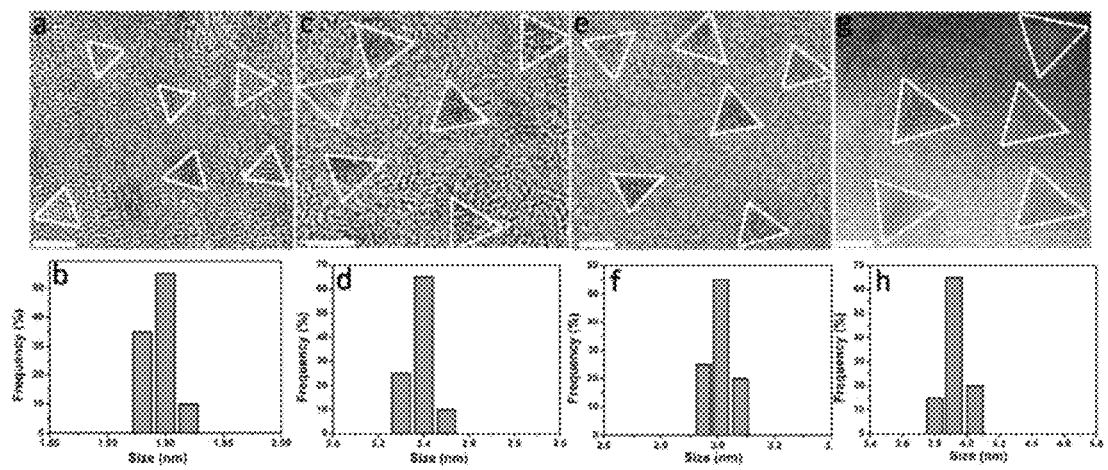
FIG. 32 shows TEM images illustrating the corresponding size distribution of B-(a,b), G- (c,d), Y- (e,f), and R-NBE-T-CQDs (g,h). Scale bar, 2 nm. (The triangular projections are highlighted by white contour lines).
Figure 33:
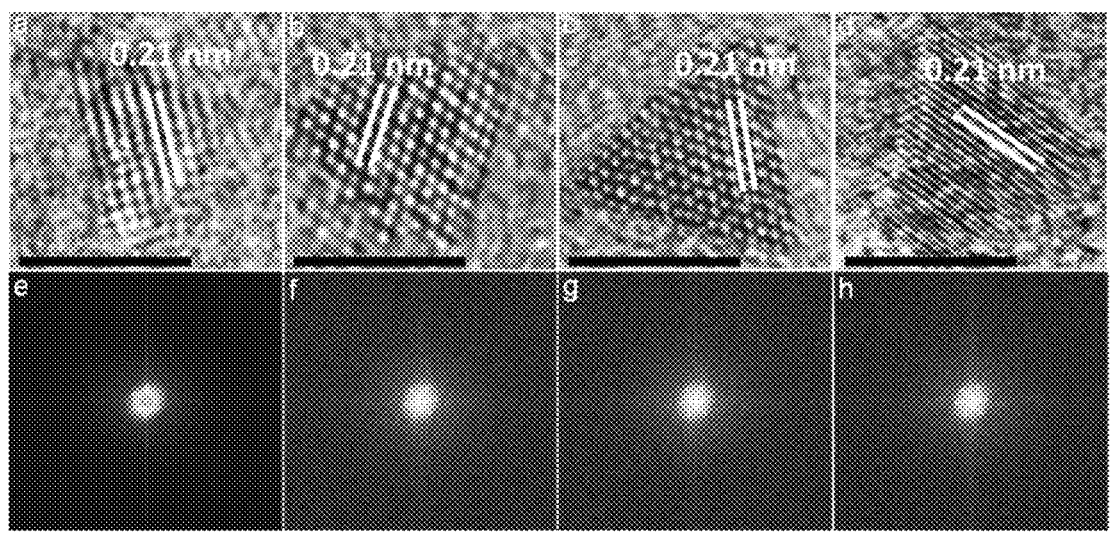
FIG. 33 shows the HRTEM images and corresponding fast Fourier transform (FFT) patterns of B- (a, e), G- (b, f), Y- (c, g), and R-NBE-T-CQDs (d, h). Scale bar, 2 nm.
Figure 34:
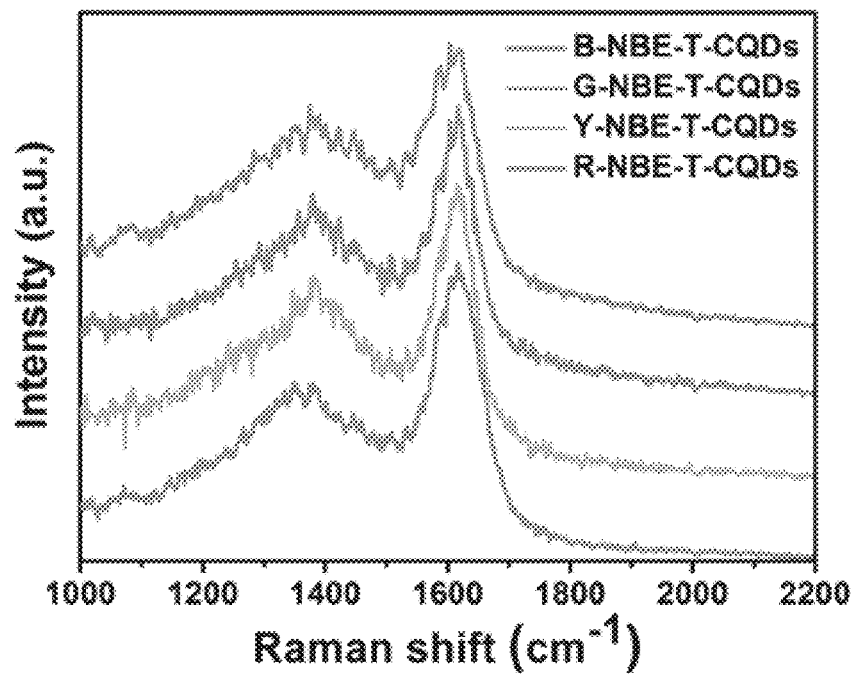
FIG. 34 shows the Raman spectra of B-, G-, Y-, and R-NBE-T-CQDs excited at 633 nm.
Figure 35:
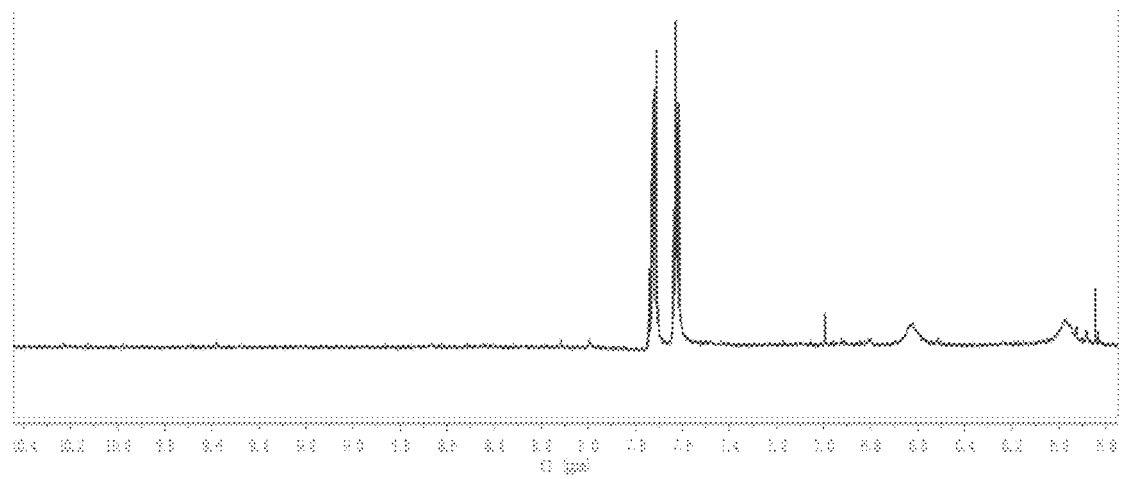
FIG. 35 shows the $^1$H-NMR spectra of G-NBE-T-CQDs in acetone-d6.
Figure 36:
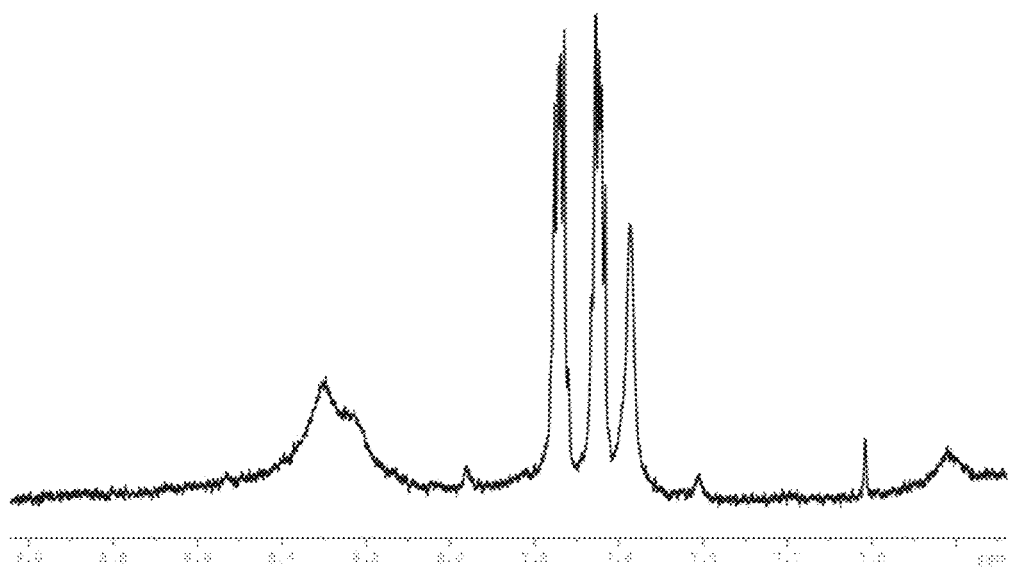
FIG. 36 shows the $^1$H-NMR spectra of Y-NBE-T-CQDs in acetone-d6.
Figure 37:
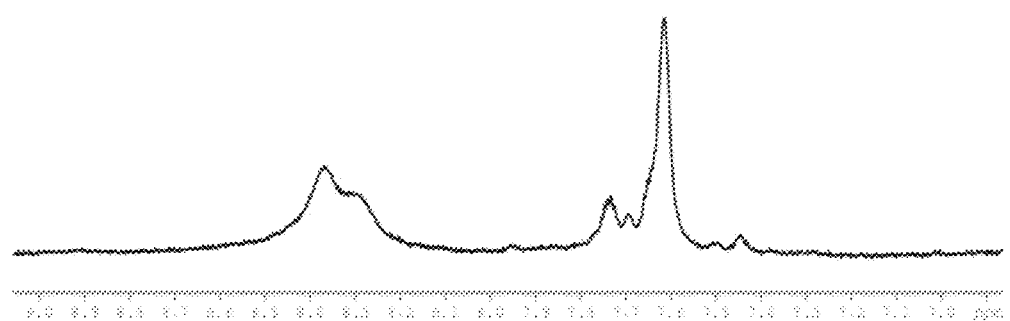
FIG. 37 shows the $^1$H-NMR spectra of R-NBE-T-CQDs in acetone-d6.
Figure 38:
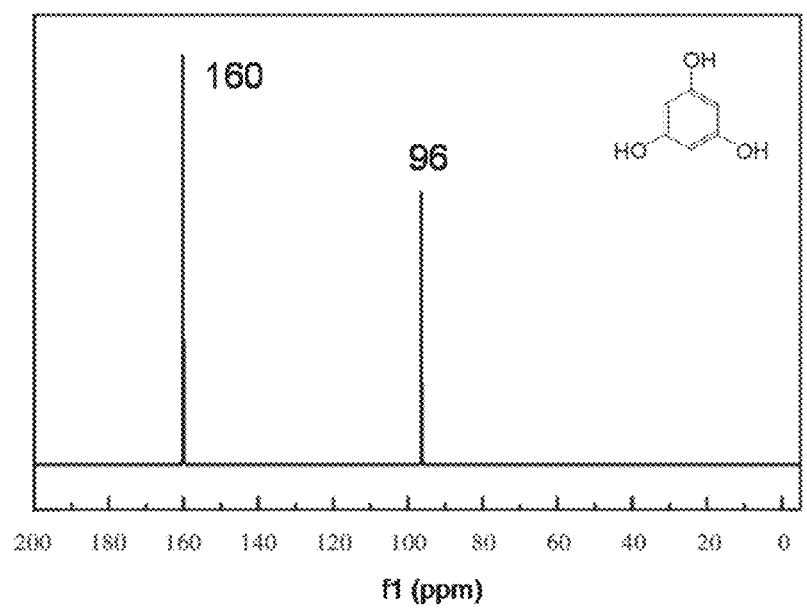
FIG. 38 shows the $^{13}$C-NMR spectra of phloroglucinol in acetone-d6.
Figure 39:
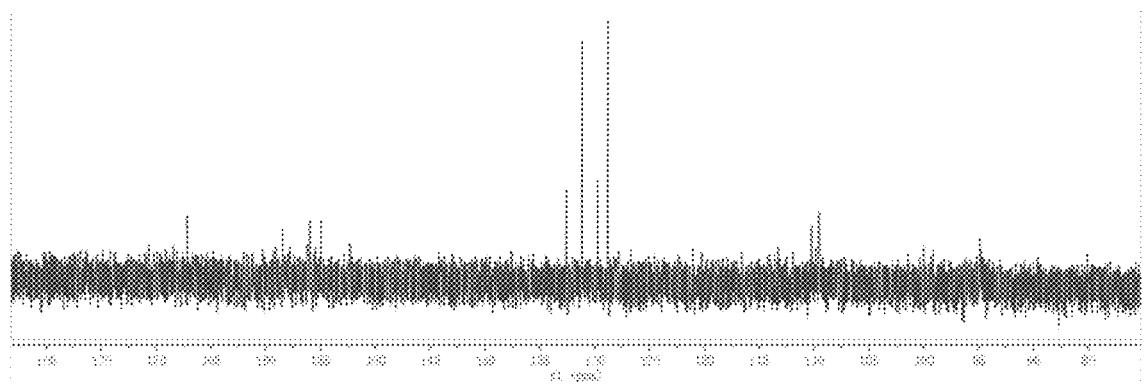
FIG. 39 shows the $^{13}$C-NMR spectra of G-NBE-T-CQDs in methanol-d4.
Figure 40:
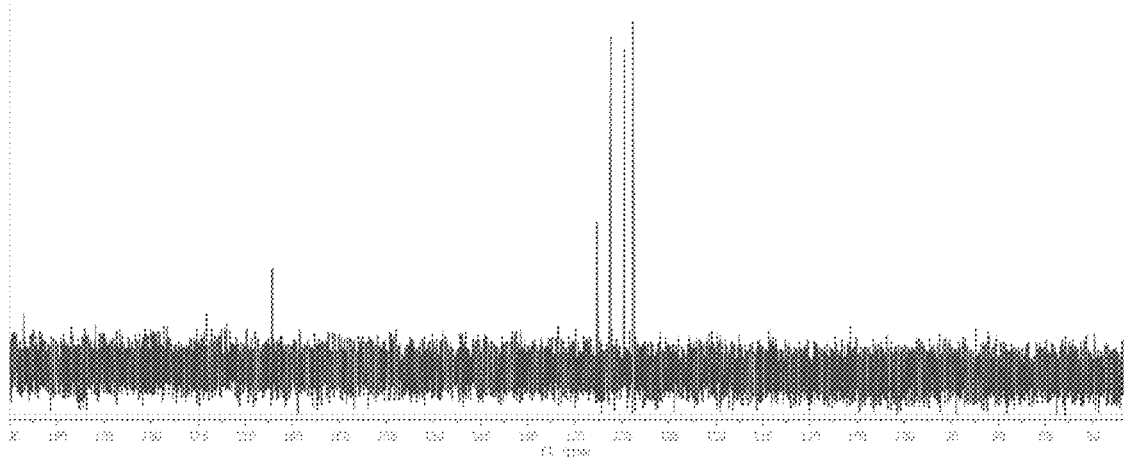
FIG. 40 shows the $^{13}$C-NMR spectra of Y-NBE-T-CQDs in methanol-d4.
Figure 41:
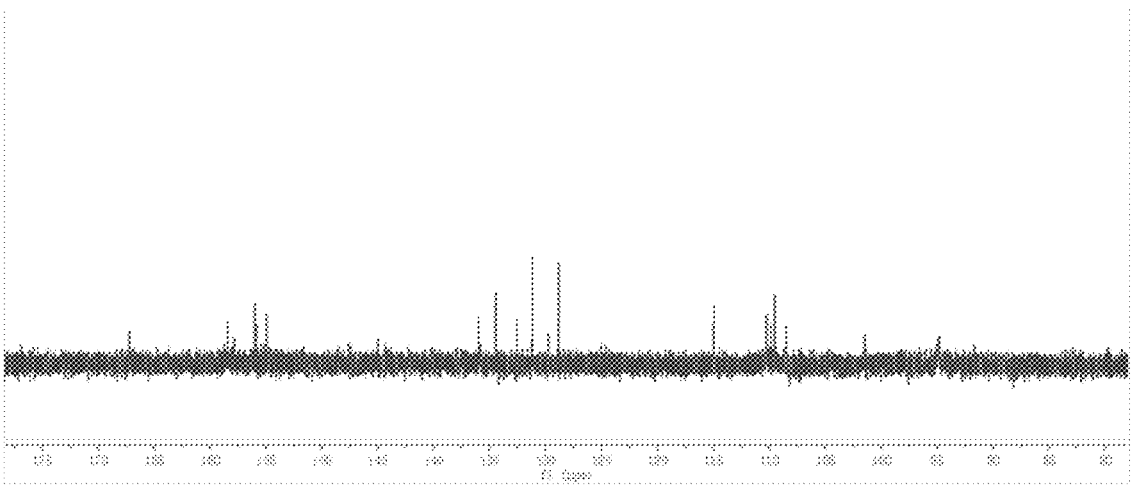
FIG. 41 shows the $^{13}$C-NMR spectra of R-NBE-T-CQDs in methanol-d4.
Figure 42:
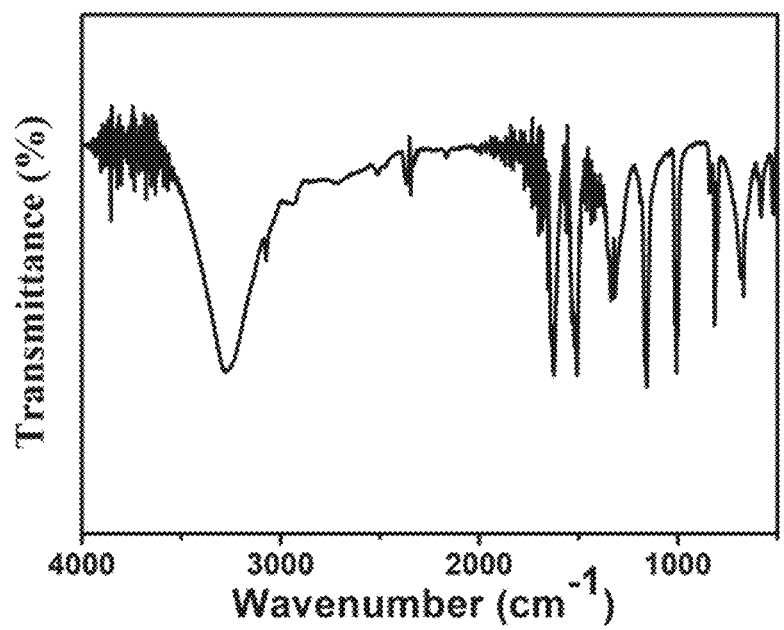
FIG. 42 shows the FT-IR spectra of phloroglucinol.
Figure 43:
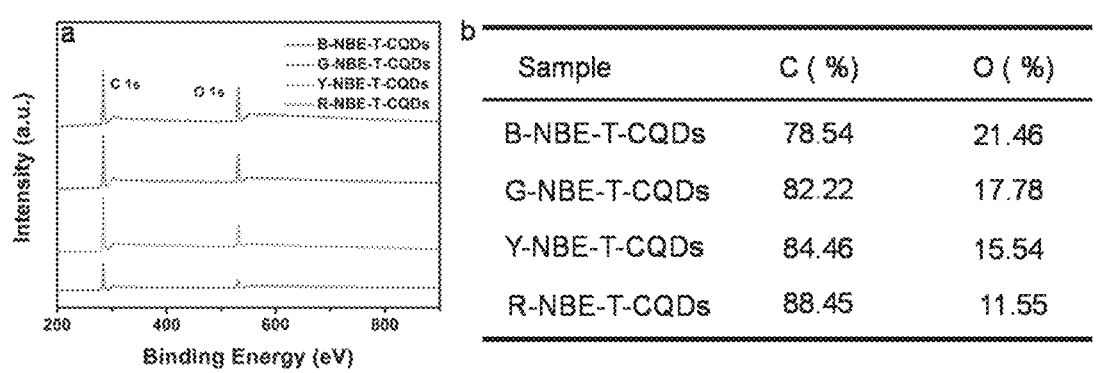
FIG. 43 shows the XPS spectra(a) and the resulting analysis result on the relative contents of C and O atoms (b) of B-, G-, Y-, and R-NBE-T-CQDs.
Figure 44:
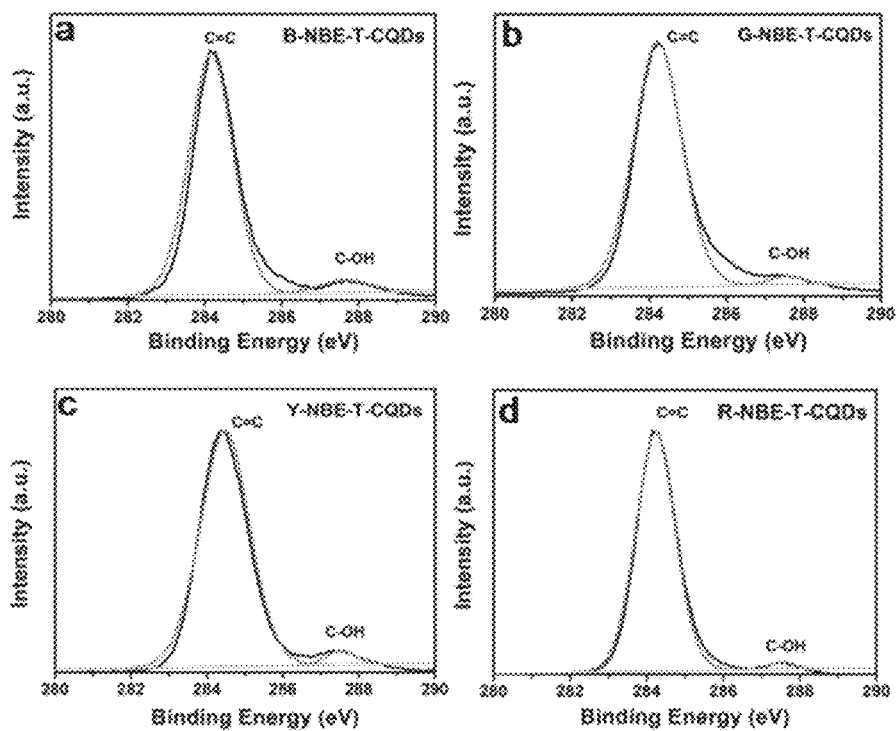
FIG. 44 shows the high-resolution C1s XPS spectra of B- (a), G- (b), Y- (c), and R-NBE-T-CQDs (d).
Figure 45:
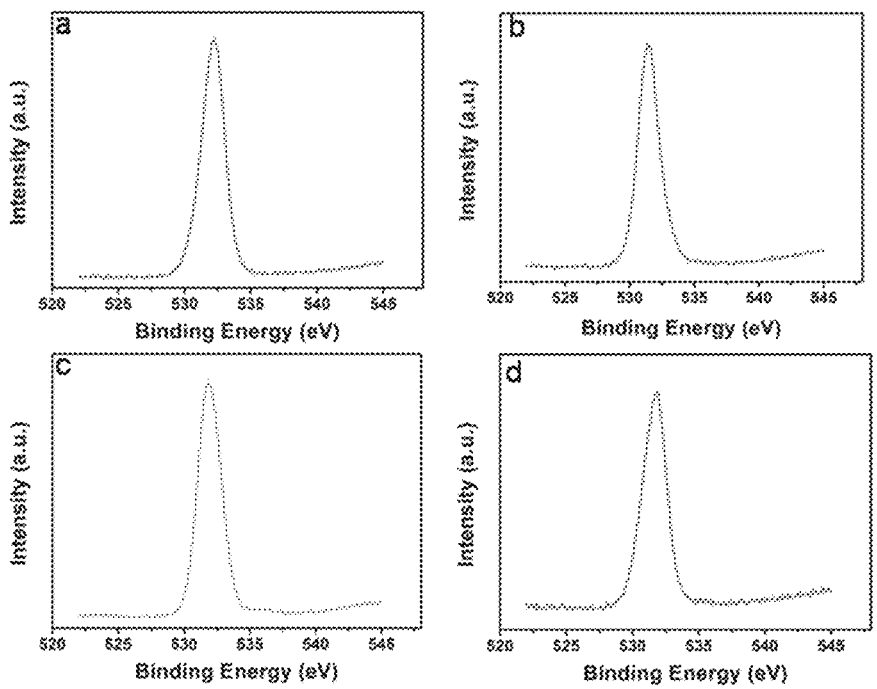
FIG. 45 shows the high-resolution O1s XPS spectra of B- (a), G- (b), Y- (c), and R-NBE-T-CQDs (d).
Figure 46:
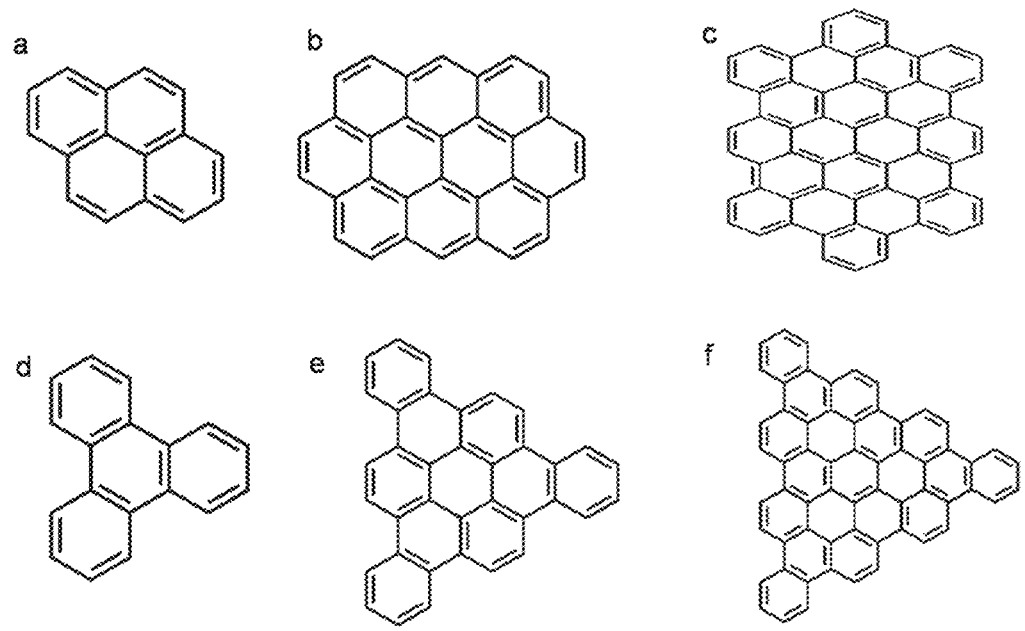
FIG. 46 shows the model CQDs with square-like structure (named S-CQDs-1 (a), S-CQDs-2 (b), and S-CQDs-3 (c)) and triangular structure (named T-CQDs-1 (d), T-CQDs-2 (e), and T-CQDs-3 (f)).
Figure 47:
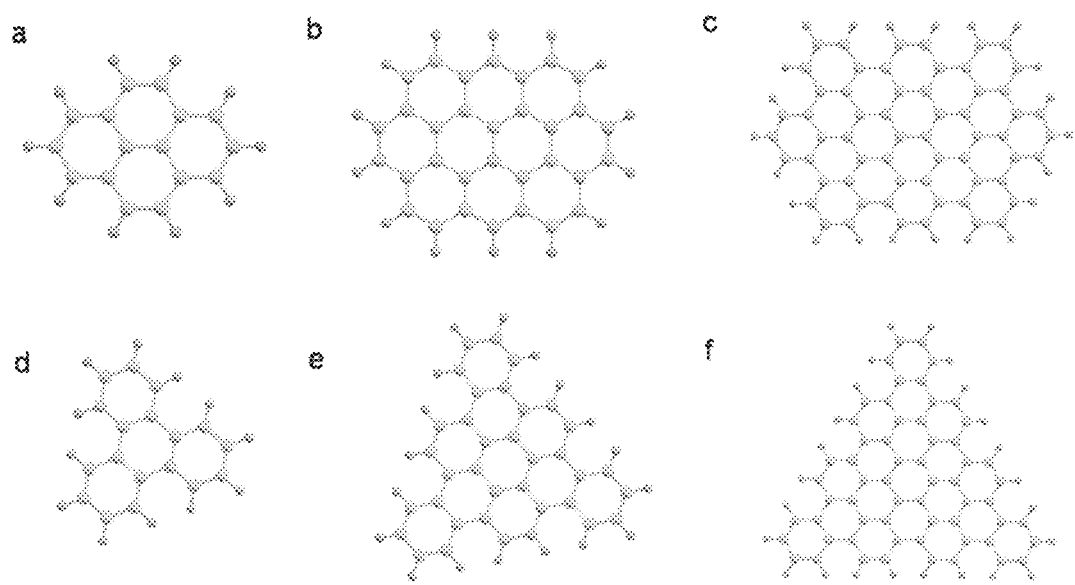
FIG. 47 shows the ball-and-stick model of CQDs with square-like structure (named S-CQDs-1 (a), S-CQDs-2 (b), and S-CQDs-3 (c)) and triangular structure (named T-CQDs-1 (d), T-CQDs-2 (e), and T-CQDs-3 (f)).
Figure 48:
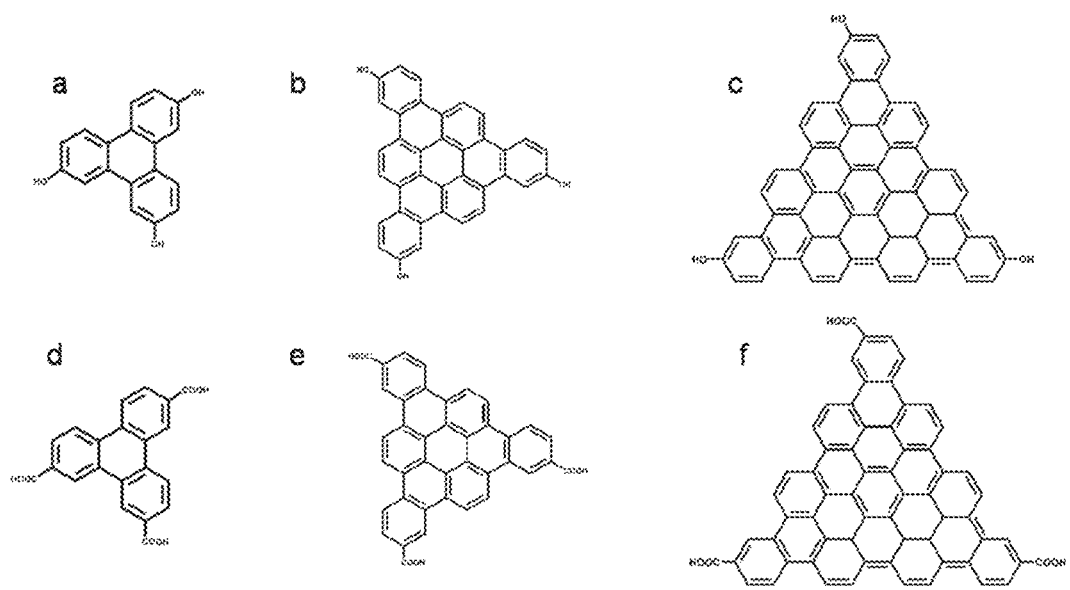
FIG. 48 shows the model CQDs with triangular structure functionalized with —OH (named T-CQDs-OH-1 (a). T-CQDs-OH-2 (b), and T-CQDs-OH-3 (c)) and —COOH groups (named T-CQDs-COOH-1 (d), T-CQDs-COOH-2 (e), and T-CQDs-COOH-3 (f)) at edge sites.
Figure 49:
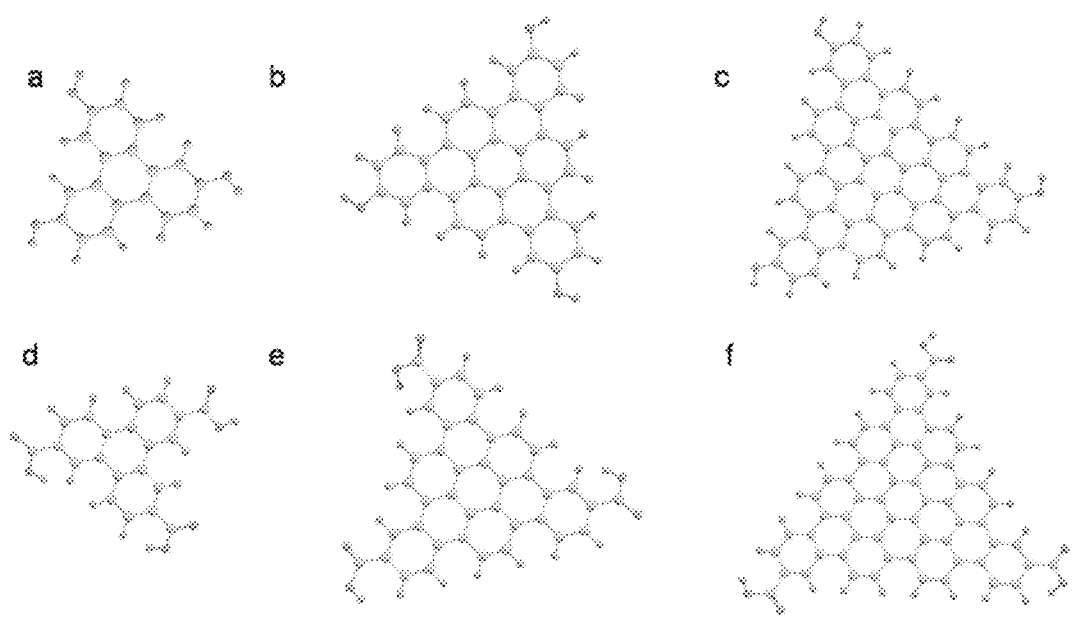
FIG. 49 shows the ball-and-stick model of CQDs with triangular structure functionalized with —OH (named T-CQDs-OH-1 (a), T-CQDs-OH-2 (b), and T-CQDs-OH-3 (c)) and —COOH groups (named T-CQDs-COOH-1 (d), T-CQDs-COOH-2 (e), and T-CQDs-COOH-3 (f)) at edge sites.
Figure 50:
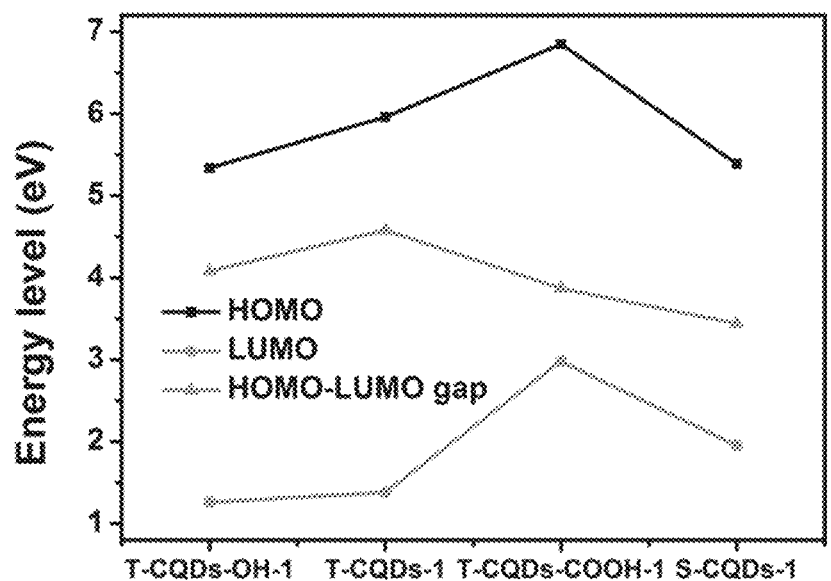
FIG. 50 shows the energy levels of T-CQDs-OH-1, T-CQDs-1, T-CQDs-COOH-1 and S-CQDs-1.
Figure 51:
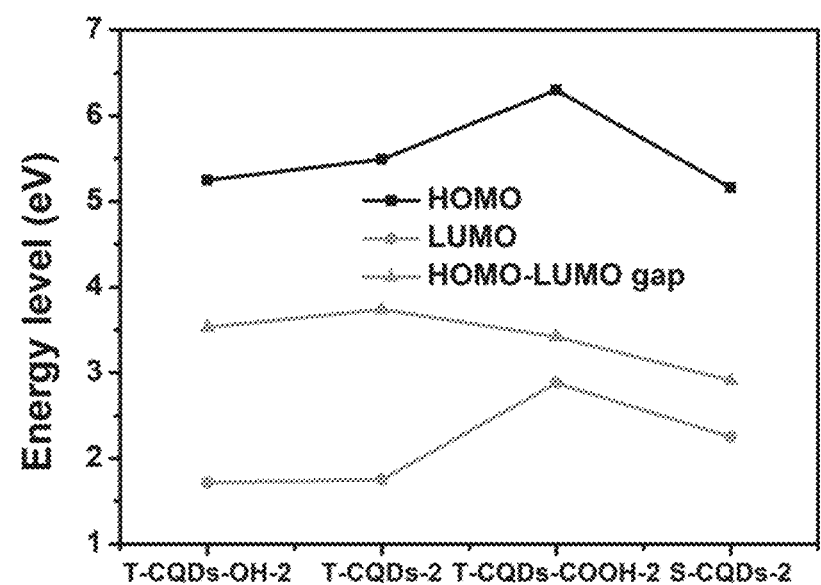
FIG. 51 shows the electron orbital energy levels of T-CQDs-OH-2, T-CQDs-2, T-CQDs-COOH-2 and S-CQDs-2.
Figure 52:
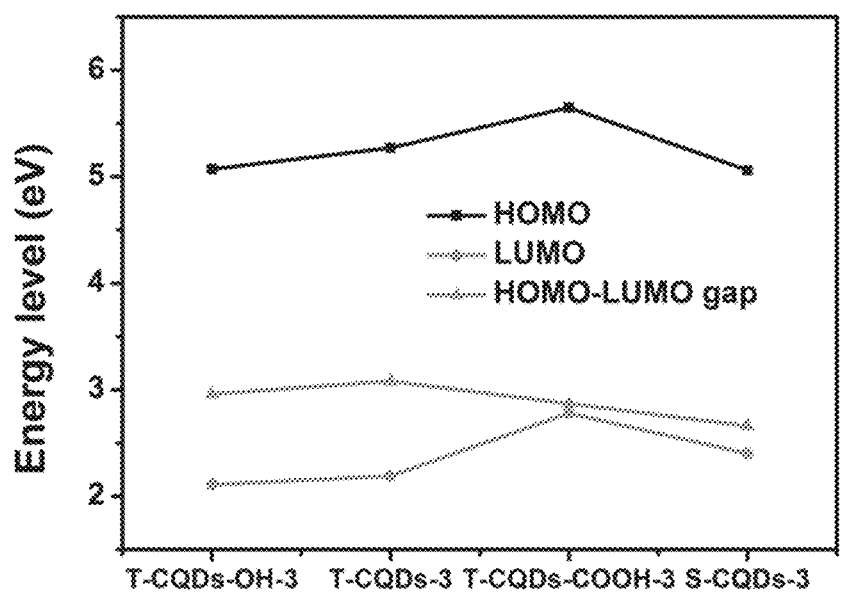
FIG. 52 shows the electron orbital energy levels of T-CQDs-OH-3, T-CQDs-3, T-CQDs-COOH-3 and S-CQDs-3.
Figure 53:
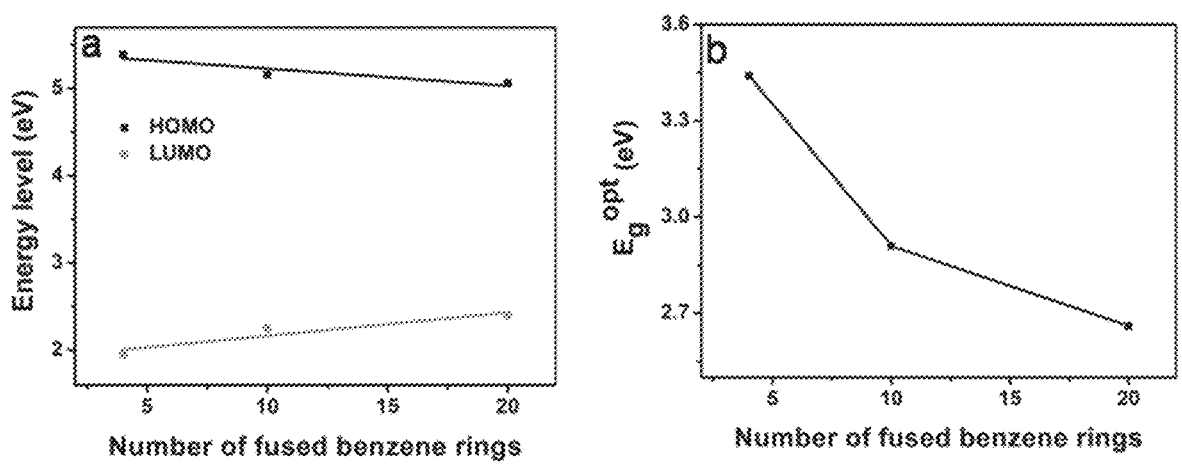
FIG. 53 shows the calculated HOMO and LUMO energy levels (a) and bandgap energies (b) of S-CQDs as a function of the number of fused benzene rings.
Figure 54:
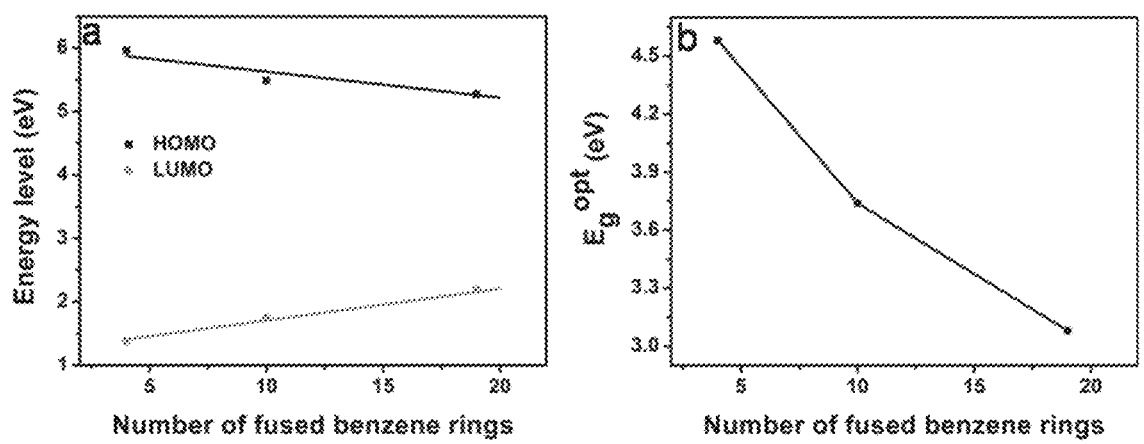
FIG. 54 shows the calculated HOMO and LUMO energy levels (a) and bandgap energies (b) of T-CQDs as a function of the number of fused benzene rings.
Figure 55:
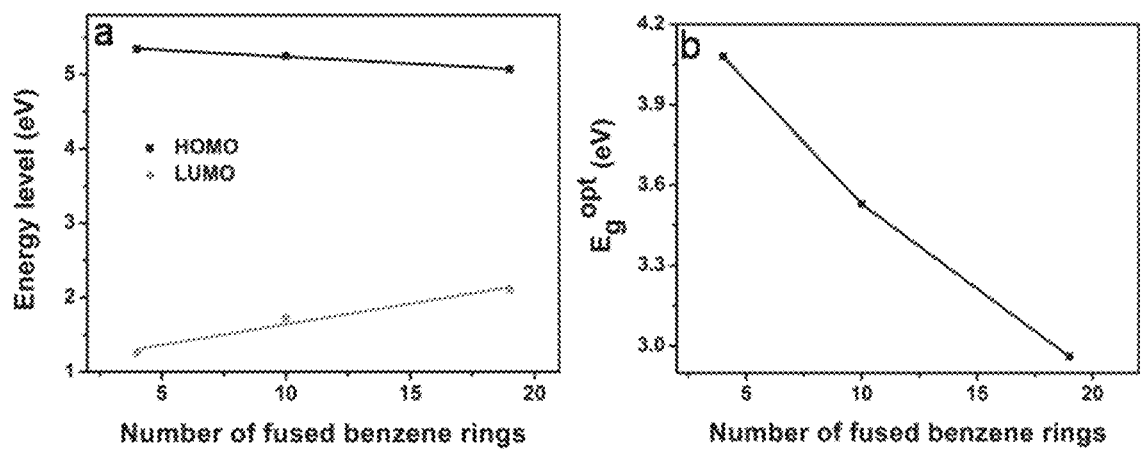
FIG. 55 shows the calculated HOMO and LUMO energy levels (a) and bandgap energies (b) of T-CQDs-OH as a function of the number of fused benzene rings.
Figure 56:
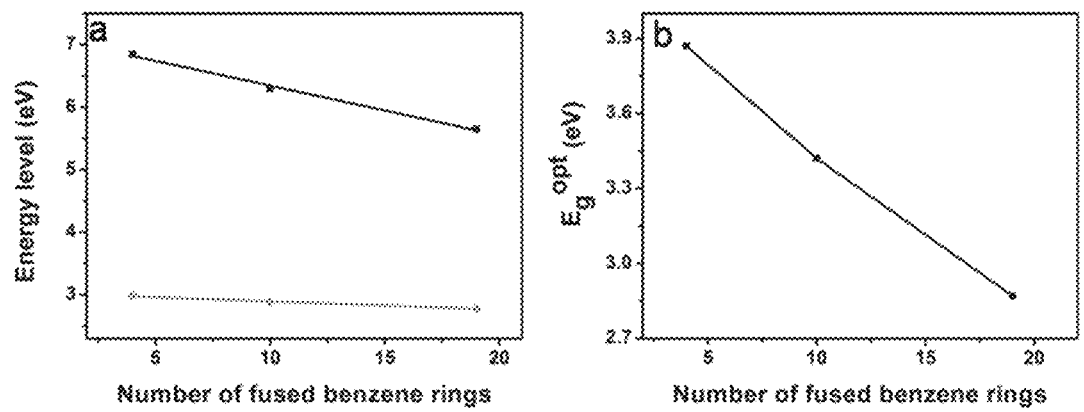
FIG. 56 shows the calculated HOMO and LUMO energy levels (a) and bandgap energies (b) of T-CQDs-COOH as a function of the number of fused benzene rings.
Figure 57:
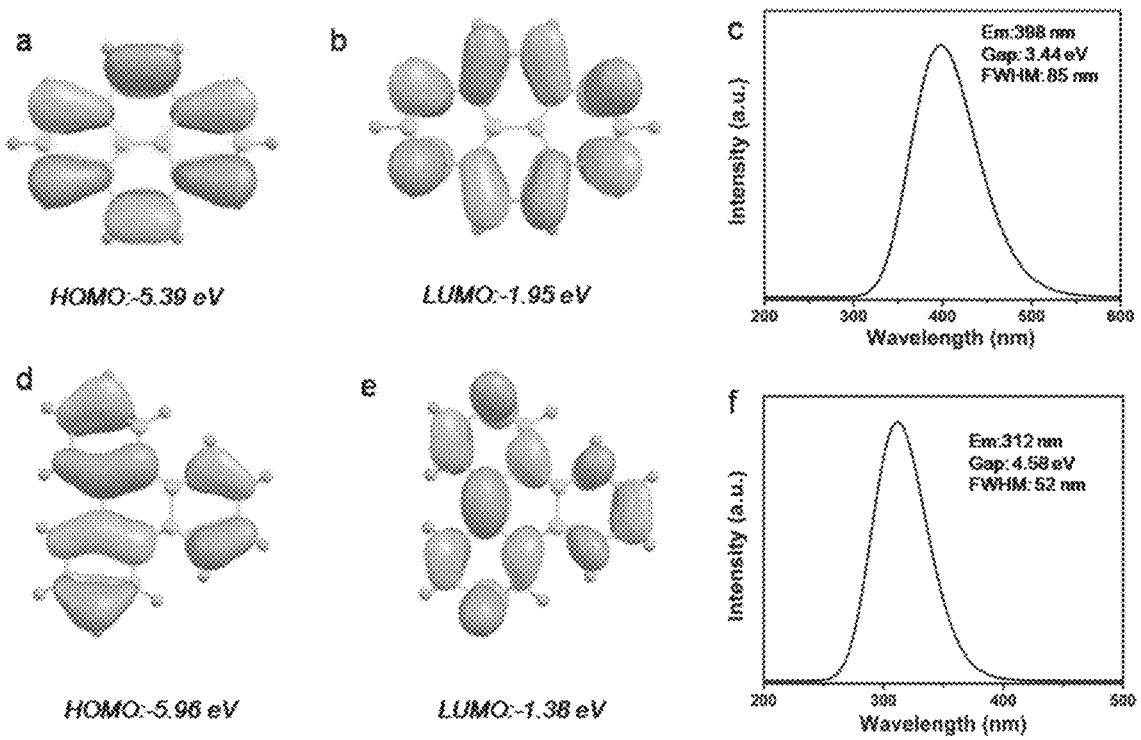
FIG. 57 shows the calculated molecular orbitals for HOMO (a) and LUMO (b) and PL spectra (c) of S-CQDs-1. The calculated molecular orbitals for HOMO (d) and LUMO (e) and PL spectra (f) of T-CQDs-1.
Figure 58:
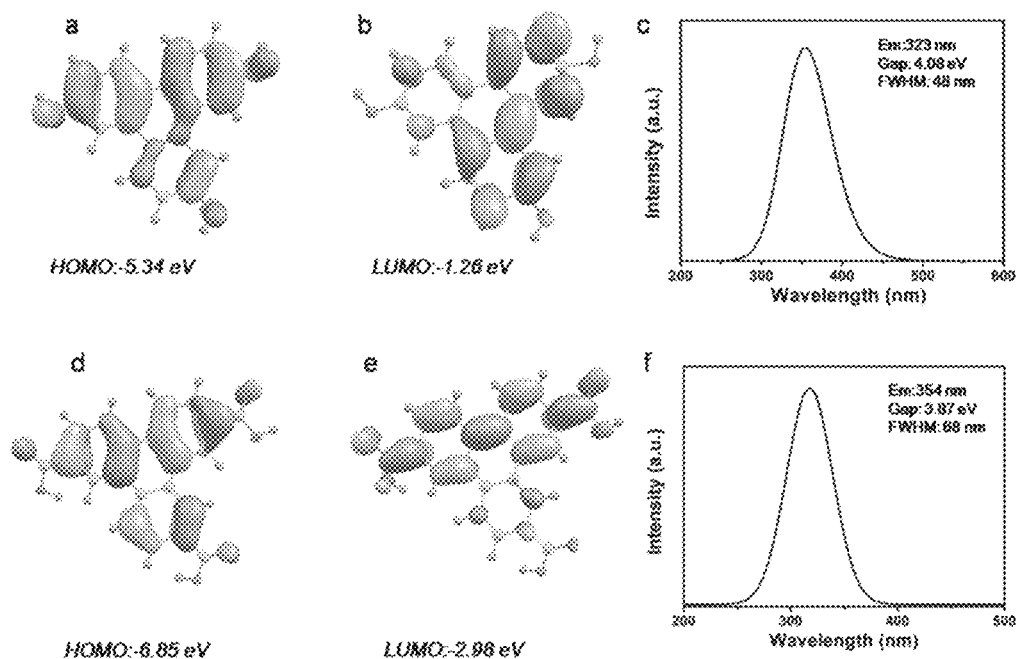
FIG. 58 shows the calculated molecular orbitals for HOMO (a) and LUMO (b) and PL spectra (c) of T-CQDs-OH-1. The calculated molecular orbitals for HOMO (d) and LUMO (e) and PL spectra (f) of T-CQDs-COOH-1.
Figure 59:
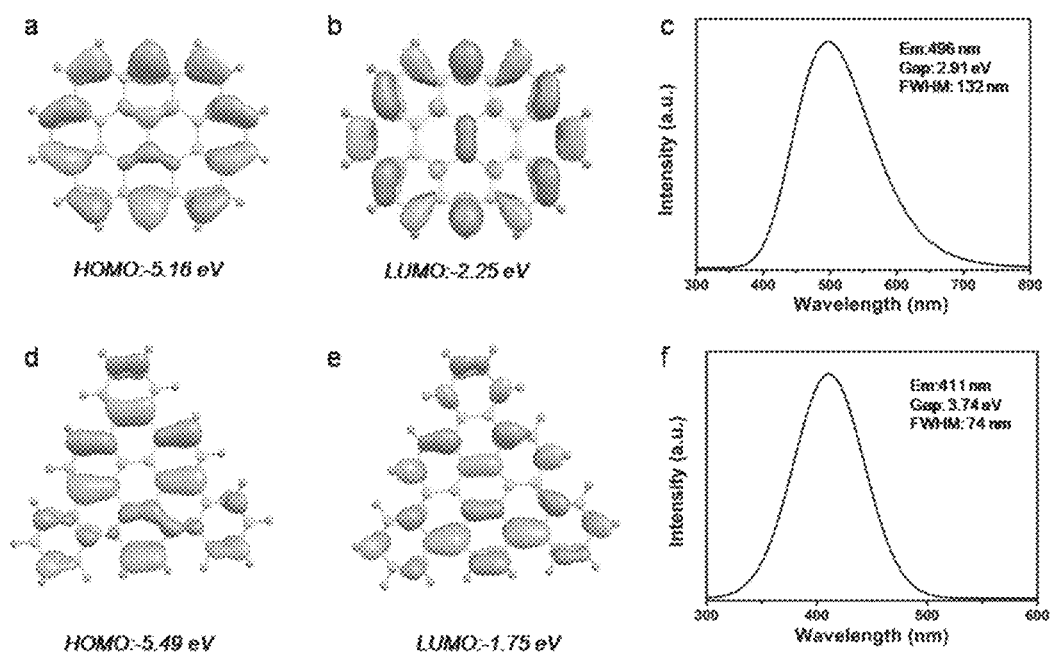
FIG. 59 shows the calculated molecular orbitals for HOMO (a) and LUMO (b) and PL spectra (c) of S-CQDs-2. The calculated molecular orbitals for HOMO (d) and LUMO (e) and PL spectra (f) of T-CQDs-2.
Figure 60:
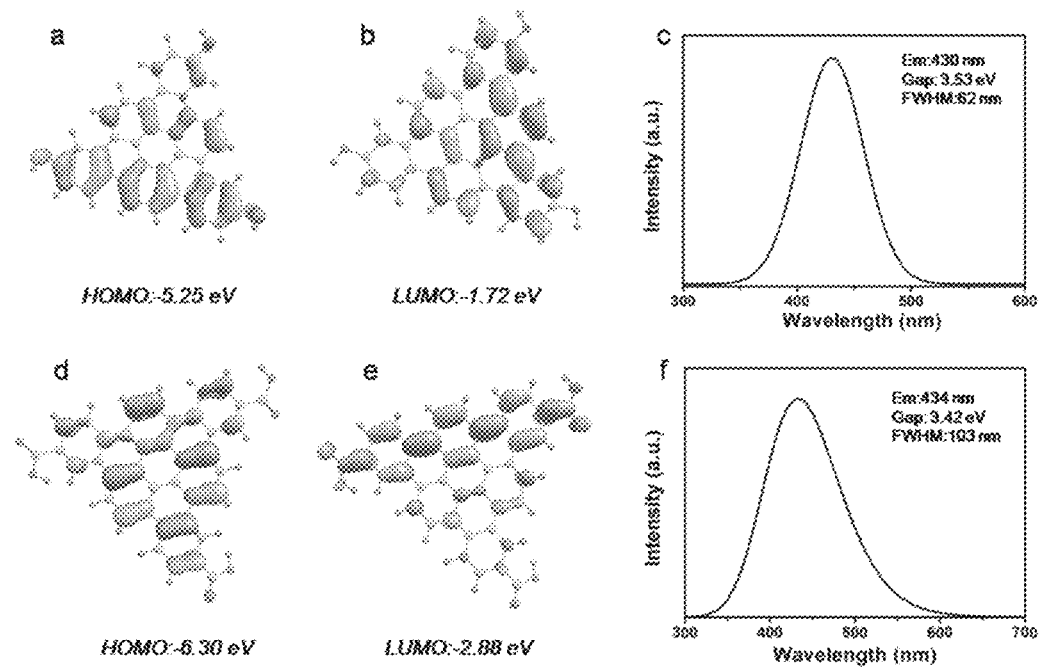
FIG. 60 shows the calculated molecular orbitals for HOMO (a) and LUMO (b) and PL spectra (c) of T-CQDs-OH-2. The calculated molecular orbitals for HOMO (d) and LUMO (e) and PL spectra (f) of T-CQDs-COOH-2.

Detailed structural characterizations were conducted so as to further shed light on the high color-purity and reveal its intrinsic relation with the structure of the NBE-T-CQDs. It should be emphasized again that the aberration-corrected HAADF-STEM images of the NBE-T-CQDs were obtained for the first time, which clearly demonstrate the high crystalline triangular structure of the NBE-T-CQDs (FIG. 3a). The wide-area TEM images of NBE-T-CQDs all show a narrow size distribution of the nanoparticles with the obvious high crystalline triangular structure as highlighted by the white contour lines (FIG. 3b, FIG. 32). The sixfold symmetric fast Fourier transform (FFT) patterns of the HRTEM images as well as the identical well-resolved lattice fringes with a spacing of 0.21 nm corresponding to the (100) inter-planar spacing further demonstrate the almost defect-free graphene crystalline structure of the NBE-T-CQDs (FIG. 33)[3,7,10,18]. The gradually increased average sizes from 1.9 to 3.9 nm are well consistent with the red-shifted emission colors from blue to red of the triangular CQDs, manifesting the quantum confinement effect[18]. The X-ray powder diffraction (XRD) patterns of the NBE-T-CQDs show a narrow (002) peak centered at around 24° (FIG. 3c) in contrast to the ultrabroad (002) peak of the previously reported CQDs[9-11,15-18], which confirms the graphene structure of the NBE-T-CQDs with high crystallinity. The high degree of graphitization of the NBE-T-CQDs is reflected in their Raman spectra (FIG. 34), where the crystalline G band at 1615 cm$^{-1}$ is much stronger than the disordered D band at 1380 cm$^{-1}$ with a large G to D intensity ratio ($I_G/I_D$) of about 1.5-1.8, indicating the high quality of the graphene structure of the NBE-T-CQDs, and is well consistent with the high crystalline graphene structure determined by HAADF-STEM and HRTEM images. To the best of our knowledge, the $I_G/I_D$ values of the NBE-T-CQDs are among the largest ever reported to date for CQDs[18]. In the $^1$H-nuclear magnetic resonance (NMR) spectra (acetone-d6, ppm) (FIG. 3d, FIGS. 35-37), apart from the obvious aromatic hydrogen signals detected in the rang of 7-8 ppm, active hydrogen signals from hydroxy groups with broad peaks as black arrow indicated in FIG. 3d are also observed[47]. Moreover, $^{13}$C-NMR spectra (methanol-d4, ppm) of the NBE-T-CQDs (FIG. 3e, FIGS. 38-41) further confirm the functionalization with pure electron-donating hydroxy groups at the edge sites. The clearly observed resonance signals in the range of 155-170 ppm are indicative of the sp$^2$ carbon atoms bonded with hydroxy groups at the edge sites of the NBE-T-CQDs[47]. In addition, the emerging numerous signals observed in the range of 115-140 ppm in the $^{13}$C-NMR spectra compared with that of PG (FIG. 38) further demonstrates the formation of intact sp$^2$ domains during the synthesis of the NBE-T-CQDs. Note that the NBE-T-CQDs with different emission colors all exhibit similar Fourier transform infrared (FT-R) spectra, attesting to their similar chemical compositions. Besides, the strong stretching vibration bands of O—H, C=C, and C—O, characteristic of the NBE-T-CQDs are also observed at 3435, 1630, and 1100 cm$^{-1}$, respectively (FIG. 42). The X-ray photoelectron spectroscopy (XPS) surveys further confirm the FT-IR data and demonstrate that the NBE-T-CQDs all have the same elemental composition (i.e. C and O) (FIG. 43). The deconvoluted high-resolution XPS spectra for C1s (FIG. 3g, FIG. 44) and O1s (FIG. 45) indicate that they contain the same C=C and O—H chemical bonds. The similar structure and chemical compositions indicate that the optical properties of the NBE-T-CQDs are dominated by their sizes due to the quantum confinement effect[18].

Taken together, it is evident that under the given reaction conditions in tandem with the elaborate separation and purification, the as-prepared NBE-T-CQDs are highly crystalline and have a unique triangular structure functionalized with pure electron-donating hydroxyl groups at the edge sites. Significantly, the NBE-T-CQDs show almost no surface defects due to the highly crystalline structure and the absence of such electron-withdrawing oxygen-containing groups as carboxyl, carbonyl and epoxy groups, which could act as surface defects and trap sites usually observed in conventional CQDs. The sharply reduced electron-phonon coupling confirmed by detailed optical characterizations coupled with the absence of surface defects due to the unique triangular structure of the NBE-T-CQDs yield the strong high color-purity excitonic emission[27-33].

Example 3: Theoretical Investigation

Theoretical Calculations:

All the optical properties of different kinds of model CQDs were calculated using time-dependent density functional theory (TDDFT) method as implemented in the Gaussian09 software package. The 6-311G(d) basis set was selected to combine with the functional B3LYP throughout all calculations (B3LYP/6-311 G(d)). The first excited state was optimized in vacuum to calculate the emission energy (wavelength) which is the energy difference between the ground and the first excited state.

Device Fabrication and Characterization:

Indium-tin-oxide (ITO) coated glass substrates was cleaned ultrasonically in organic solvents (acetone and isopropyl alcohol), rinsed in deionized water, and then dried in an oven at 150° C. for 10 min. The substrates were cleaned with a UV-ozone treatment to enrich the ITO surface with oxygen to increase the ITO work function. The poly(3,4-ethylenedioxythiophene):poly(styrenesulfonate) (PEDOT:PSS) hole injection layer (HIL) was spin coated at 2000 rpm for 35 s on the ITO with a thickness of about 30 nm, followed by annealing in an oven at 150° C. for 15 min. Subsequently, the emissive layer of NBE-T-CQDs blended poly(N-vinyl carbazole) (PVK) was spin coated at 3000 rpm for 45 s over the surface of PEDOT:PSS film from the mixed solution of o-dichlorobenzene and ethanol solution, followed by baking on a hot plate at 80° C. for 30 min to form the active region of the NBE-T-CQDs-based monochrome LEDs. Finally, the substrates were transferred to a vacuum chamber and a 30 nm thick 1,3,5-tris(N-phenylbenzimidazol-2-yl) benzene (TPBI) electron transport layer (ETL) was thermally deposited with base pressure of 3×10$^{-4}$ Pa. After that, a 20 nm Ca and 100 nm thick Al cathode was deposited using a shadow mask with 2 mm width. The active area of the devices was thus 4 mm2. The thermal deposition rates for TPBI and Ca/Al are 1, 1, and 3 Å s-1, respectively. PEDOT:PSS was used as a buffer layer on the anode mainly to increase the anode work function from 4.7 (ITO) to 5.0 eV and to reduce the surface roughness of the anode to obtain stable and pinhole free electrical conduction across the device. TPBI was chosen as the ETL because of its good electron transport capability and its interfacial phase compatibility with the active emission layer. The thickness of films was measured using a Dektak XT (Bruker) surface profilometer and a spectroscopic ellipsometer (Suntech). The luminance-current-voltage (L-I-V) characteristics were measured using a computer-controlled Keithley 236 SMU and Keithley 200 multimeter coupled with a calibrated Si photodiode. Electroluminescence (EL) spectra were measured by an Ocean Optics 2000 spectrometer, which couples a linear charge coupled device (CCD)-array detector ranging from 350 to 1100 nm.

Figure 4:
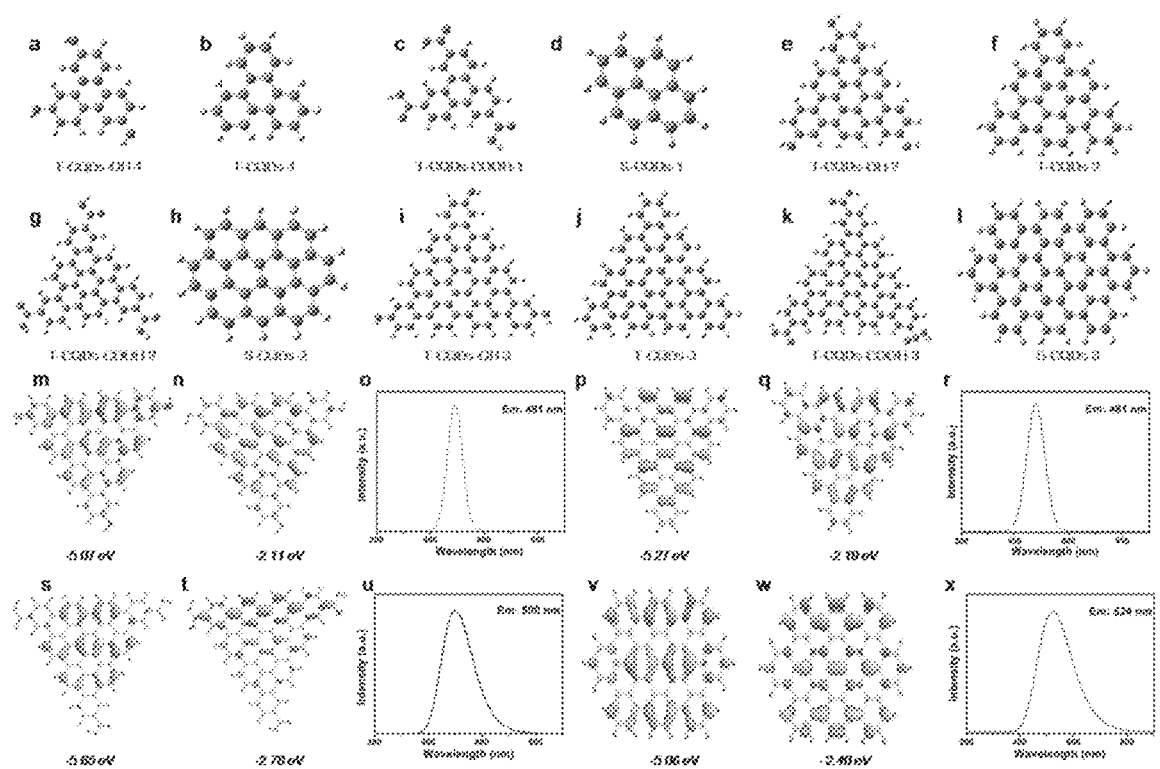
FIG. 4 shows the time-dependent DFT calculation results.

Without being bound by any theory, in some embodiments, our proposal that the unique highly crystalline triangular structure functionalized with pure electron-donating hydroxyl groups at the edge sites are responsible for the high color-purity excitonic emission of the NBE-T-CQDs was further confirmed by DFT theory calculations. The optical properties of different kinds of model CQDs with triangular structure consisting of 4, 10 and 19 fused benzene rings functionalized with electron-donating hydroxyl groups (T-CQDs-OH) (FIGS. 4a, e, i) or electron-withdrawing carboxyl groups (T-CQDs-COOH) (FIGS. 4c, g, k) or without functionalization (T-CQDs) (FIGS. 4b, f, j) as well as the square-like structure consisting of 4, 10 and 20 fused benzene rings (S-CQDs) (FIGS. 4d, h, l) were all calculated for comparison (FIGS. 46-49). Remarkably, the T-CQDs-OH and T-CQDs show distinct charge delocalization and optical properties compared with T-CQDs-COOH and S-CQDs. The calculated molecular orbitals demonstrate the highly delocalized charges of NBE-T-CQDs-OH and T-CQDs compared with T-CQDs-COOH and S-CQDs (FIGS. 4m-x, FIGS. 50-56). For the optical properties of different kinds of model CQDs, apart from the differences in the emission peaks and energy levels such as the HOMO, LUMO and bandgap energies (FIGS. 4m-x, FIGS. 50-56), the FWHM of the PL spectra of T-CQDs-OH is slightly smaller than that of T-CQDs, but much smaller than those of T-CQDs-COOH and S-CQDs. At the fundamental level, it stands as a universal law that the T-CQDs-OH and T-CQDs show much higher color-purity emission than T-CQDs-COOH and S-CQDs, which is observed by all these different kinds of model CQDs consisting of different number of fused benzene rings (FIGS. 57-60). Take for example, the PL spectra of T-CQDs-OH-3 consisting of 19 fused benzene rings shows a narrow FWHM of 64 nm (FIG. 4o), which is slightly smaller than that of T-CQDs-3 (FWHM: 73 nm) (FIG. 4r), but is even smaller than half of the FWHM of the PL spectra of T-CQDs-COOH-3 (FWHM: 135 nm) (FIG. 4u) and S-CQDs-3 (FWHM: 149 nm) (FIG. 4x). More significantly, the increased thermodynamic stability of T-CQDs-OH compared with T-CQDs and S-CQDs are also demonstrated by theoretical calculations (Table 3), which directly show the outstanding structural stability of T-CQDs-OH.

TABLE 3

Calculated energy of different kinds of CQDs
(Hartree, 1Hartree = 2625.5 kJ/mol).

|  | 1 | 2 | 3 |
| --- | --- | --- | --- |
| S-CQDs | −615.9 | −1228.2 | −2300.4 |
| T-CQDs | −693.3 | −1383.1 | −2301.5 |
| T-CQDs-OH | −1144.8 | −1608.8 | −2527.3 |

These elaborately designed theoretical calculations demonstrate that the triangular structure and electron-donating hydroxyl groups play significant roles in determining the high color-purity of the NBE-T-CQDs which can be explained in detail as follows: (1) The highly delocalized charges and outstanding structural stability of the unique triangular structure of the NBE-T-CQDs could result in dramatically reduced electron-phonon coupling, and thus lead to the increased color-purity of the excitonic emission of the NBE-T-CQDs. (2) In addition, the pure electron-donating hydroxyl groups at the edge sites of the NBE-T-CQDs can also greatly increase the π electron cloud density and facilitate the pure radiative recombination of confined electrons and holes. On the contrary, the electron-withdrawing carboxyl groups on $sp^2$-hybridized carbons can induce significant local distortions as well as acting as surface defects simultaneously, which could trap carriers and finally result in dramatically increased FWHM of the PL spectra of CQDs (FIGS. 4s-u, FIGS. 58-60). Summarizing the above, the theoretical investigation demonstrates that the unique highly crystalline triangular structure functionalized with pure electron-donating hydroxyl groups at the edge sites show highly delocalized charges, outstanding structural stability, and thus dramatically reduced electron-phonon coupling, which are responsible for the high color-purity excitonic emission of the NBE-T-CQDs.

Example 4: LED Performance

Figure 5:
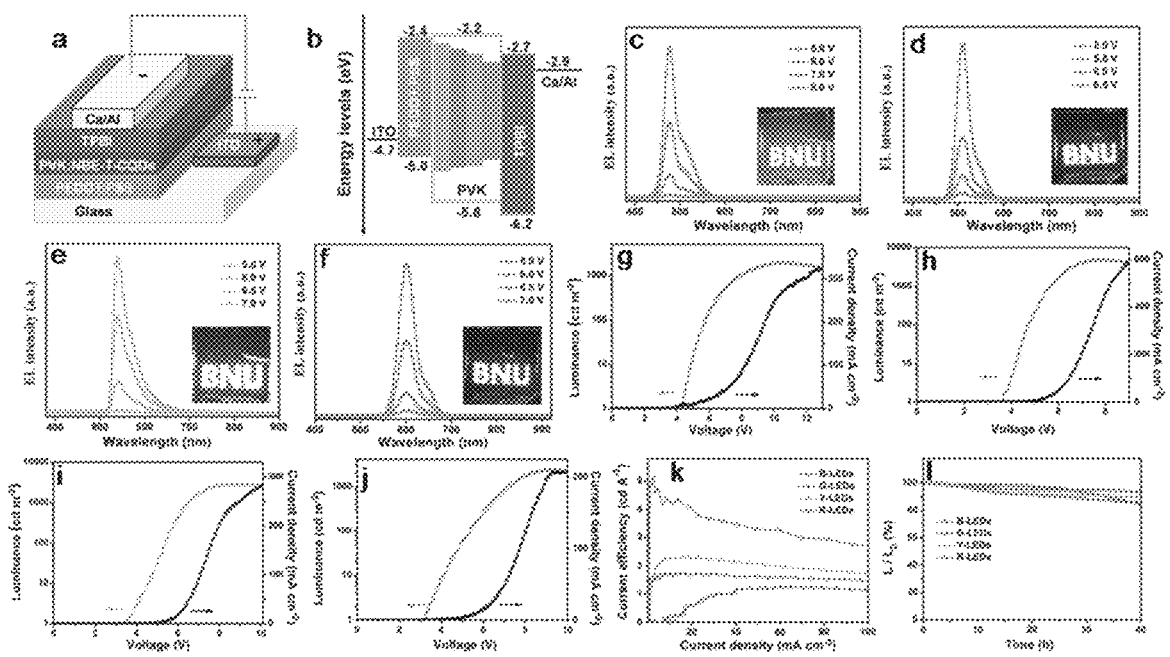
FIG. 5 depicts the structure, energy diagram and performance characterization of the NBE-T-CQDs-based LEDs.
Figure 61:
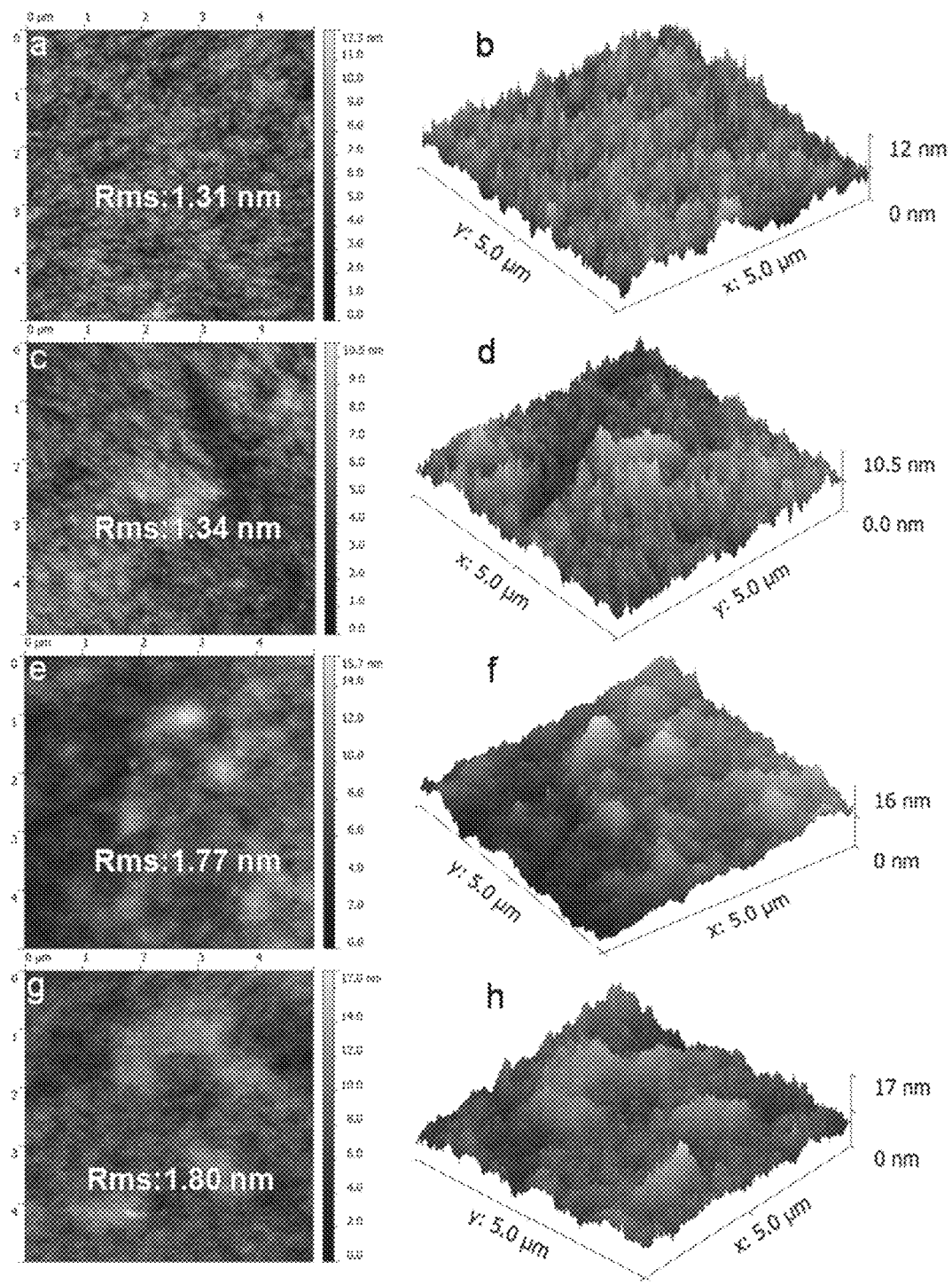
FIG. 61 shows the AFM height images of active emission layers of B- (a, b), G- (c, d), Y- (e, f), and R-LEDs (g, h).
Figure 62:
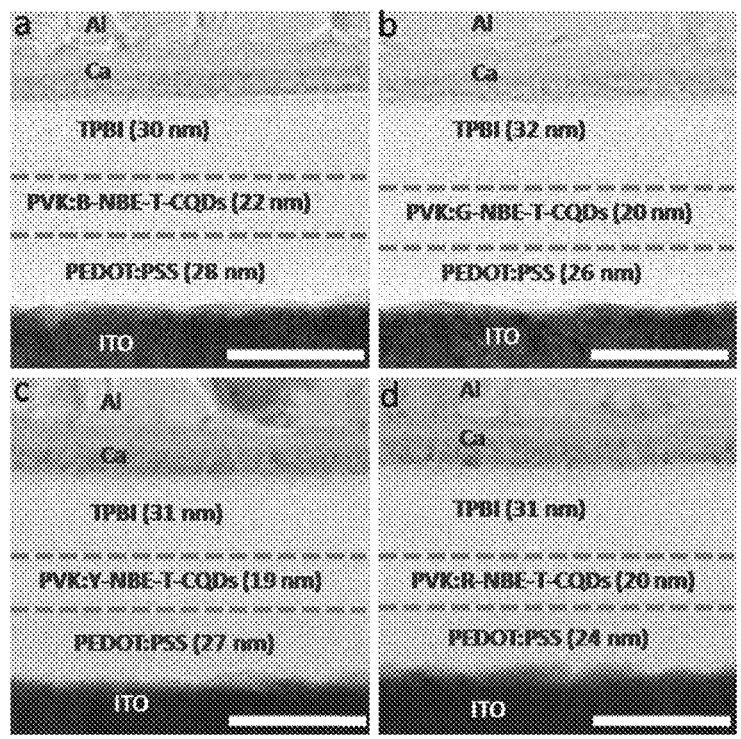
FIG. 62 shows the cross-sectional TEM images of B- (a), G- (b), Y- (c), and R-LED (d) devices based on the ITO/PEDOT:PSS/PVK:NBE-T-CQDs/TPBi/Ca/Al structure. Scale bar: 50 nm.
Figure 63:
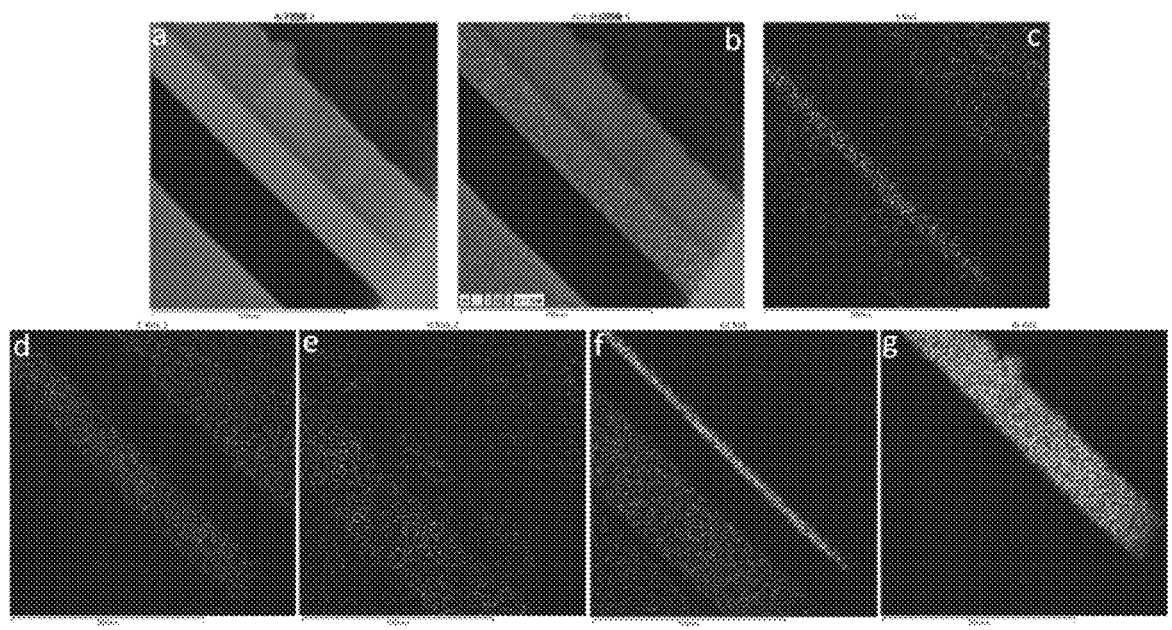
FIG. 63 shows the cross-sectional TEM image (a) and corresponding EDX map (b) of a typical LED device. The individual layers can be clearly distinguished based on their elemental composition such as S (c), C (d), N (e). Ca (f), and Al (g).

The bright and high color-purity excitonic emission of the NBE-T-CQDs has prompted us to exploit their applications in LEDs for the development of next-generation display technology. A conventional simple structure was used for fabrication of the LEDs from blue to red with the NBE-T-CQDs blended poly(N-vinyl carbazole) (PVK) as the active emission layer, as shown in FIG. 5a. PVK was selected as host material due to its excellent hole transporting properties as well as favourable film forming properties[48]. Atomic force microscopy (AFM) measurements show that the NBE-T-CQDs blended PVK film has a smooth and uniform surface coverage with small root-mean-square (rms) roughness in the range of 1.31-1.80 nm (FIG. 61). The QY of B-, G-, Y-, and R-NBE-T-CQDs blended PVK films were determined to be about 56, 62, 48 and 42%, respectively. The device structure consists of, from the bottom up, a ITO glass substrate anode, a poly(3,4-ethylenedioxythiophene):poly(styrenesulfonate) (PEDOT:PSS) hole injection layer (HIL), an active NBE-T-CQDs:PVK blended emission layer, a 1,3,5-tris(N-phenylbenzimidazol-2-yl) benzene (TPBI) electron transport layer (ETL), and a Ca/Al double-layered cathode. The thickness of PEDOT:PSS, PVK:NBE-T-CQDs, and TPBI layers in LED devices are determined to be about 24-28, 19-22, and 30-32 nm, respectively, as confirmed by the cross-sectional TEM images and the EDX maps of LED devices (FIGS. 62-63). As observed in the energy level diagram of the NBE-T-CQDs-based LEDs shown in FIG. 5b, the HOMO and LUMO energy levels of NBE-T-CQDs are located within those of the PVK, and have a small energy barrier for charge injection from both electrodes to the PVK host[48]. Then, the electrons and holes can be efficiently transferred from PVK to NBE-T-CQDs emitter in the active layer. The transferred electrons and holes can undergo radiative recombination in the NBE-T-CQDs, giving rise to the electroluminescence (EL)[48].

Figure 64:
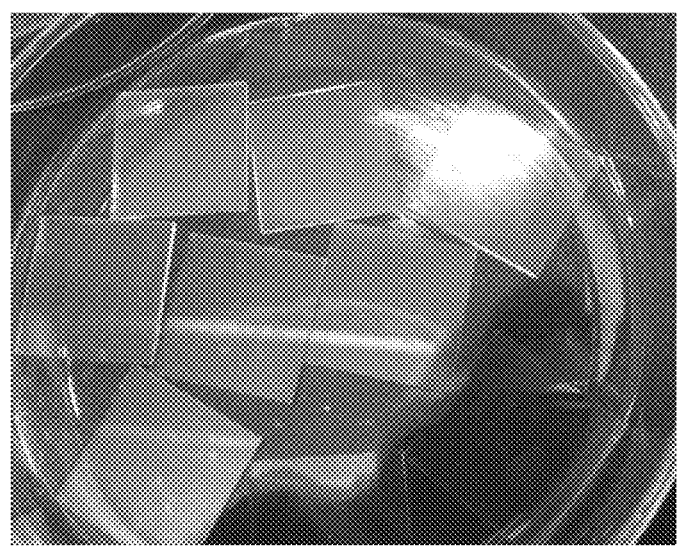
FIG. 64 shows photographs of the ITO with Beijing Normal University (BNU) logo.
Figure 65:
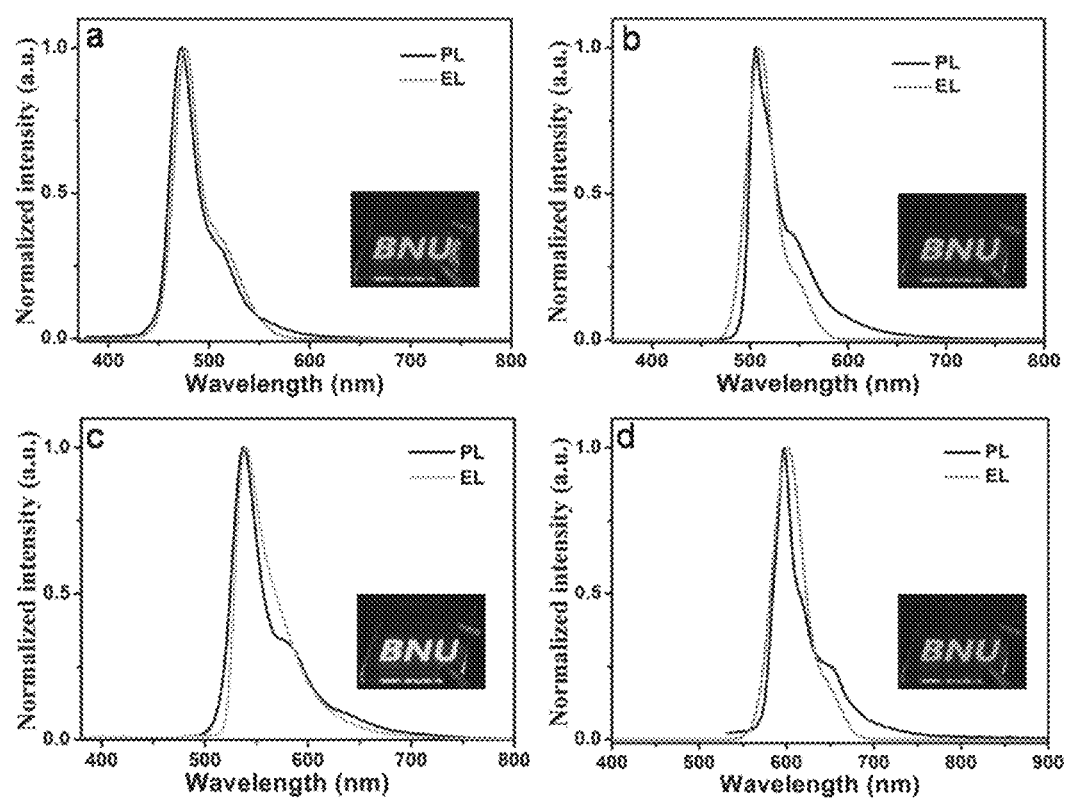
FIG. 65 shows the normalized PL spectra and the corresponding output EL spectra of B- (a), G- (b), Y- (c), and R-LEDs (d). The insets are the operation photographs of B-, G-, Y-, and R-LEDs with the logo of the BNU.
Figure 66:
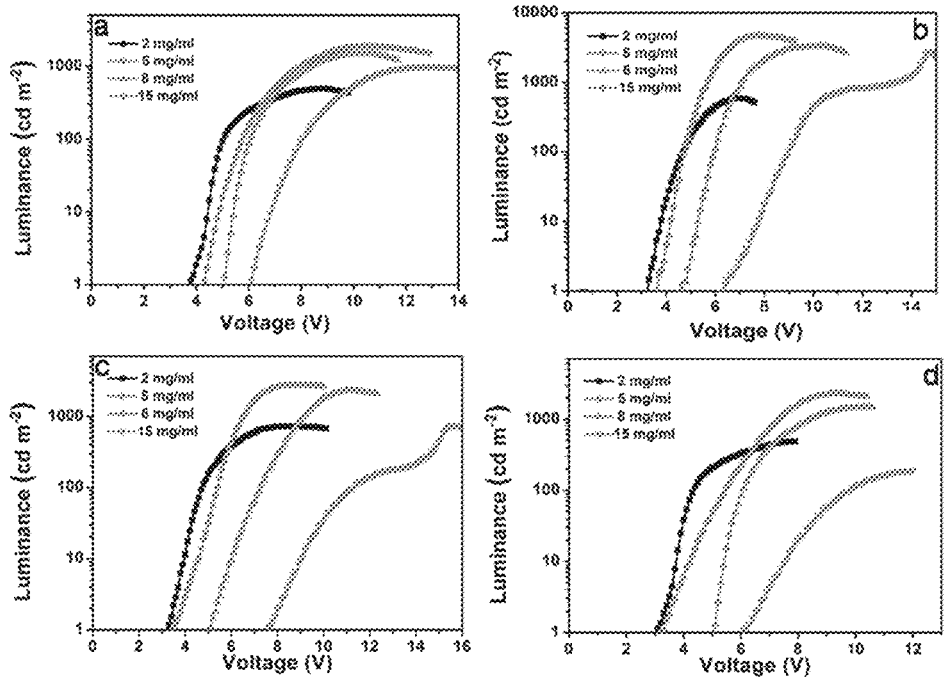
FIG. 66 shows the impact of the concentration of NBE-T-CQDs blended PVK on the performance of B- (a), G- (b), Y- (c), and R-LEDs (d).

The EL spectra of the NBE-T-CQDs-based LEDs are presented in FIGS. 5c-f. They exhibit peak wavelengths at 476, 510, 540, and 602 nm, respectively, and are in good agreement with the PL emission peaks measured in the solution, indicating the excellent dispersion of the NBE-T-CQDs in the host material of PVK (FIGS. 64-65). More significantly, the NBE-T-CQDs-based LEDs show high color-purity EL emission with narrow FWHM of 30, 32, 38 and 39 nm for the B-, G-, Y-, and R-LEDs, respectively, which is even comparable to the well-developed high color-purity inorganic QDs-based LEDs[49,50]. The operation photographs with Beijing Normal University (BNU) logo (insets of FIGS. 5c-f, FIG. 65) display the close-up view of the bright, uniform and defect-free surface high color-purity EL emission from blue, green, yellow, to red of the NBE-T-CQDs-based LEDs. The apparently voltage-independent emission color (FIGS. 5c-f) indicates the high color-stability of the LEDs, which is of great significance for display technology. To the best of our knowledge, this is the first report for the fabrication of high color-purity CQDs-based LEDs (FWHM<40 nm) with stable emission color from blue to red with the NBE-T-CQDs blended PVK as active emission layer.

The typical luminance and current density curves as a function of applied voltage for the NBE-T-CQDs-based LEDs are shown in FIGS. 5g-j and FIG. 66. Table 4 shows the performance of high color-purity NBE-T-CQDs-based LEDs from blue to red.

TABLE 4

| LEDs | PL/FWHM (nm) | EL/FWHM (nm) | $V_{ON}$ (V) | $L_{max}$ (cd m$^{-2}$) | $\eta_c$ (cd A$^{-1}$) |
|---|---|---|---|---|---|
| B-LEDs | 472/30 | 476/30 | 4.3 | 1882 | 1.22 |
| G-LEDs | 507/29 | 510/32 | 3.7 | 4762 | 5.11 |
| Y-LEDs | 538/30 | 540/38 | 3.5 | 2784 | 2.31 |
| R-LEDs | 598/30 | 602/39 | 3.1 | 2344 | 1.73 |

Figure 67:
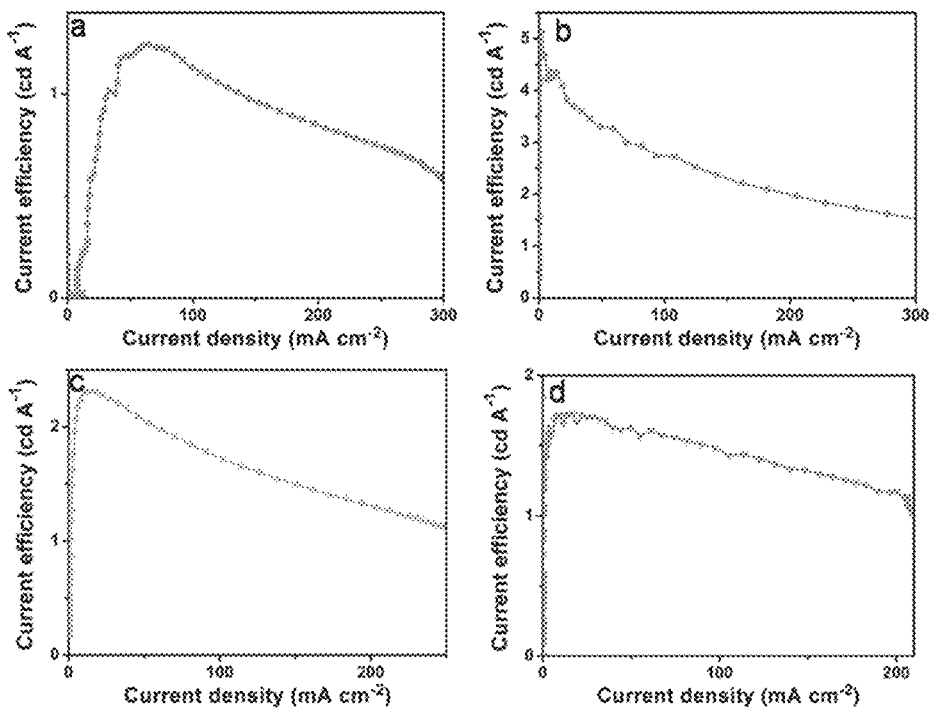
FIG. 67 shows the current efficiency vs current density of B- (a), G- (b), Y- (c), and R-LEDs (d).

The $V_{on}$, defined as the bias voltage applied to a LEDs producing a brightness of 1 cd/m$^2$, decreased from 4.3 to 3.1 V for the LEDs from blue to red, which are much lower than the previous reported CQDs-based LEDs (see. e.g., Yuan et al., *Adv. Mater.* 29, 1604436 (2017) and Kim et al., *Sci. Rep.* 5, 11032 (2015)) due to the maching energy levels of the related materials (FIG. 5b). The $L_{max}$ and $\eta_c$ reach about 4762 cd/m$^2$ and 5.1 cd/A for green LEDs (G-LEDs) (FIGS. 5h, k), respectively, which are the best performance ever reported for the CQDs-based LEDs, and is about 50 and 110 times higher than our previous reported G-LEDs which directly used bandgap fluorescent CQDs as the active emission layer without using the PVK host. Other colored high color-purity LEDs based on the NBE-T-CQDs fabricated with the same device structure also show high-performance with $L_{max}$, reaching 1882, 2784, and 2344 cd/m$^2$ for the B-, Y-, and R-LEDs coupled with corresponding 11 of 1.22, 2.31, and 1.73 cd/A (FIGS. 5g, i-k, FIG. 67), respectively, which are to some extent comparable to the QDs-based LEDs (Table 5).

TABLE 5

Comparison of our high color-purity NBE-T-CQDs-based LEDs with other previously reported high-performance semiconductor QDs-based LEDs.

| LEDs | EL/FWHM (nm) | $V_{ON}$ (V) | $L_{max}$ (cd m$^{-2}$) | $\eta_c$ (cd A$^{-1}$) | Reference |
|---|---|---|---|---|---|
| B-LEDs | 476/30 | 4.3 | 1882 | 1.22 | This work |
| G-LEDs | 510/32 | 3.7 | 4762 | 5.11 | |
| Y-LEDs | 540/38 | 3.5 | 2784 | 2.31 | |
| R-LEDs | 602/39 | 3.1 | 2344 | 1.73 | |
| blue | 470/28 | 2.4 | 4200 | 0.32 | 51 |
| green | 525/32 | 3-4 | 3700 | 1.1 | 50 |
| yellow | 576/35 | | 4470 | 1.3 | |
| orange | 595/28 | | 3200 | 1.8 | |
| red | 619/28 | | 9064 | 2.8 | |
| green | 517/N/A | N/A | 154 | 0.3 | 53 |
| blue | 455/20 | 5.1 | 742 | 0.14 | |
| green | 516/23 | 4.2 | 946 | 0.43 | |
| orange | 586/23 | 4.6 | 528 | 0.08 | |
| blue | 490/19 | 3.0 | 35 | N/A | 54 |
| green | 515/19 | 3.0 | 330 | | |
| green | 510/N/A | N/A | 2935 | 4.9 | 55 |
| green | 518/64 | 2.8 | 4182 | 1.53 | 56 |

Figure 68:
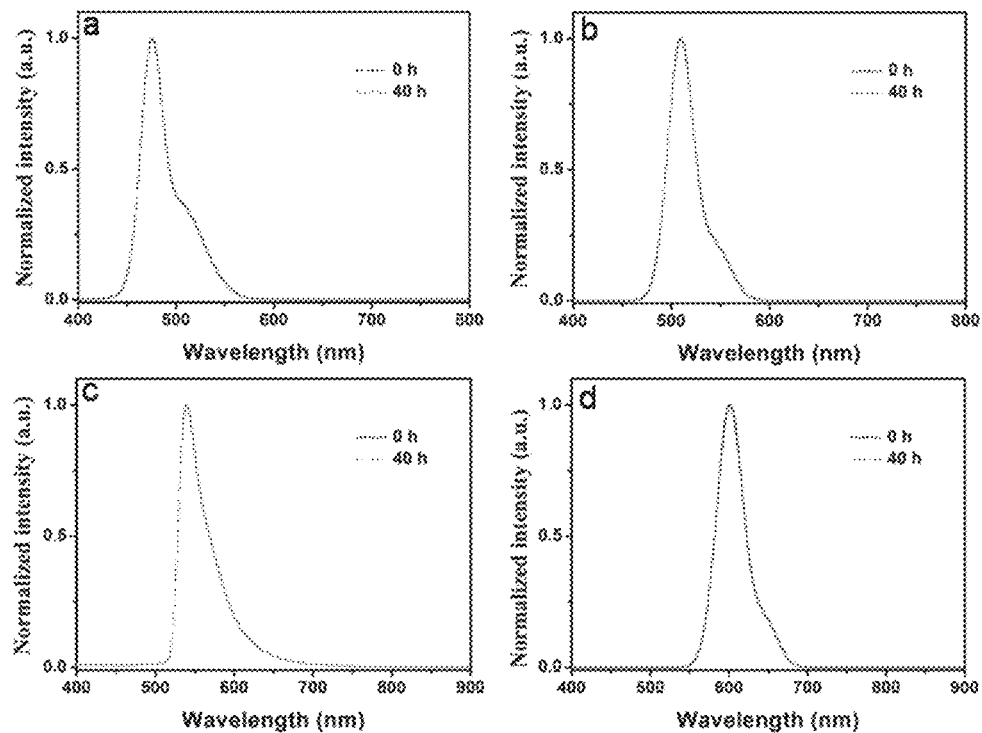
FIG. 68 shows the normalized EL spectra of B- (a), G- (b). Y- (c), and R-LEDs (d) at 0 and 40 h under operation at 6 V.
Figure 69:
FIG. 69 shows the photograph of G-LEDs under operation at an extremely high voltage of 25.83 V.

Besides the bright fluorescence inherent to the NBE-T-CQDs, the remarkable performance of our LEDs can also be attributed to the optimized charge balance in the emission layer with the hole-transport PVK as host materials. As an ultrastable feature of the fluorescence of the NBE-T-CQDs, the high color-purity NBE-T-CQDs-based LEDs exhibit outstanding ambient stability. After operation for 40 h, more than 85% of initial luminance ($L_0$: 500 cd/m$^2$) are retained (FIG. 5l) without degradation of the high color-purity (FIG. 68). Moreover, the LEDs also show high stability at extremely high voltage, further demonstrating the great potential applications of the NBE-T-CQDs-based LEDs for the development of next-generation display technology (FIG. 69).

The examples and preparations provided below further illustrate and exemplify the compounds of the present invention and methods of preparing such compounds. It is to be understood that the scope of the present invention is not limited in any way by the scope of the following examples and preparations. In the following examples molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

Provided herein is the first subversive demonstration of high color-purity NBE-T-CQDs (FWHM of 29 nm) from blue to red with a QY up to 72%. The NBE-T-CQDs were prepared by facilely controlling the fusion and carbonization of three-fold symmetric PG triangulogen which possesses a unique structure with three highly reactive hydrogen atoms at the three meta-positions activated by three electron-donating hydroxyl groups in a single molecule. Detailed structural and optical characterizations together with elaborate theoretical calculations reveal that the unique rigid triangular structure, molecular purity, crystalline perfection and most importantly, the resulting weak electron-phonon interaction of the NBE-T-CQDs surrounded by hydroxy groups are the key points to the high color-purity. The multicolored LEDs based on the NBE-T-CQDs demonstrated high color-purity (FWHM of 30 nm), a $L_{max}$ of 4762 cd/m$^2$ and q, of 5.11 cd/A, rivaling the well-developed inorganic QDs-based LEDs. Moreover, the LEDs demonstrate outstanding stability. This work will inspire further research on and more optimizations of the charge injection (holes and electrons) as well as better designed devices, leading to a greatly improved performance for the high color-purity NBE-T-CQDs-based LEDs ideal for next-generation display technology.

REFERENCES

1. Lim S. Y. et al. Carbon quantum dots and their applications. *Chem. Soc. Rev.* 44, 362-381 (2015).
2. Ding, C. et al. Functional surface engineering of C-Dots for fluorescent biosensing and in vivo bioimaging. *Acc. Chem. Res.* 47, 20-30 (2014).

3. Yuan, F. L. et al. Shining carbon dots: Synthesis and biomedical and optoelectronic applications. *Nano Today* 11, 565-586 (2016).
4. Liu, J. et al. Metal-free efficient photocatalyst for stable visible water splitting via a two-electron pathway. *Science* 347, 970-974 (2015).
5. Hola, K. et al. Carbon dots-Emerging light emitters for bioimaging, cancer therapy and optoelectronics. *Nano Today* 9, 590-603 (2014).
6. Choi, H. et al. Versatile surface plasmon resonance of carbon-dot-supported silver nanoparticles in polymer optoelectronic devices. *Nat. Photonics* 7, 732-738 (2013).
7. Wang, L et al. Gram-scale synthesis of single-crystalline graphene quantum dots with superior optical properties. *Nat. Commun.* 5, 5357 (2014).
8. Sun, Y.-P. et al. Quantum-Sized Carbon Dots for Bright and Colorful Photoluminescence. *J. Am. Chem. Soc.* 128, 7756-7757 (2006).
9. Zhang, M. et al. Facile synthesis of water-soluble, highly fluorescent graphene quantum dots as a robust biological label for stem cells. *J. Mater. Chem.* 22, 7461-7467 (2012).
10. Yuan, F. L. et al. Multicolor fluorescent graphene quantum dots colorimetrically responsive to all-pH and a wide temperature range. *Nanoscale* 7, 11727-11733 (2015).
11. Fan, Z. T. et al. pH-Responsive fluorescent graphene quantum dots for fluorescence-guided cancer surgery and diagnosis. *Nanoscale* 9, 4928-4933 (2017).
12. Hutton, G. A. M. et al. Carbon Dots as Versatile Photosensitizers for Solar-Driven Catalysis with Redox Enzymes. *J. Am. Chem. Soc.* 138, 16722-16730 (2016).
13. Jiang, K. et al. Triple-Mode Emission of Carbon Dots: Applications for Advanced Anti-Counterfeiting *Angew. Chem. Int. Ed.* 55, 7231-7235 (2016).
14. Martindale, B. C. M. et al. Clean Donor Oxidation Enhances the H-2 Evolution Activity of a Carbon Quantum Dot-Molecular Catalyst Photosystem. *Angew. Chem. Int. Ed.* 55, 9402-9406 (2016).
15. Wang, Z. F. et al. 53% Efficient Red Emissive Carbon Quantum Dots for High Color Rendering and Stable Warm White-Light-Emitting Diodes. *Adv. Mater.* 29, 1702910 (2017).
16. Jiang, K. et al. Red, Green, and Blue Luminescence by Carbon Dots: Full-Color Emission Tuning and Multicolor Cellular Imaging. *Angew. Chem. Int. Ed.* 54, 5360-5363 (2015).
17. Qu, S. N. et al. Toward Efficient Orange Emissive Carbon Nanodots through Conjugated $sp^2$-Domain Controlling and Surface Charges Engineering. *Adv. Mater.* 28, 3516-3521 (2016).
18. Yuan, F. L. et al. Bright Multicolor Bandgap Fluorescent Carbon Quantum Dots for Electroluminescent Light-Emitting Diodes. *Adv. Mater.* 29, 1604436 (2017).
19. Zhu, Z. et al. Efficiency Enhancement of Perovskite Solar Cells through Fast Electron Extraction: The Role of Graphene Quantum Dots. *J. Am. Chem. Soc.* 136, 3760-3763 (2014).
20. Ye, K.-H. et al. Carbon quantum dots as a visible light sensitizer to significantly increase the solar water splitting performance of bismuth vanadate photoanodes. *Energy Environ. Sci.* 5, 772-779 (2017).
21. Tang, Q. W. et al. Rapid Conversion from Carbohydrates to Large-Scale Carbon Quantum Dots for All-Weather Solar Cells. *ACS Nano* 11, 1540-1547 (2017).
22. Li, H. et al. Carbon Quantum Dots/TiOx Electron Transport Layer Boosts Efficiency of Planar Heterojunction Perovskite Solar Cells to 19. *Nano Lett.* 17, 2328-2335 (2017).
23 Lu, S. Y. et al. Near-Infrared Photoluminescent Polymer-Carbon Nanodots with Two-Photon Fluorescence. *Adv. Mater.* 29, 1603443 (2017).
24. Dai, X. L. et al. Solution-processed, high-performance light-emitting diodes based on quantum dots. *Science* 515, 96-99 (2014).
25. Li, G. G. et al. Recent progress in low-voltage cathodoluminescent materials: synthesis, improvement and emission properties. *Chem. Soc. Rev.* 43, 7099-7131 (2014).
26. Li, H. et al. Full-Color Light-Emitting Carbon Dots with a Surface-State-Controlled Luminescence Mechanism. *ACS Nano* 10, 484-491 (2016).
27. Cortecchia, D. et al. Broadband Emission in Two-Dimensional Hybrid Perovskites: The Role of Structural Deformation. *J. Am. Chem. Soc.* 139, 39-42 (2017).
28. Emma, R. D. et al. Intrinsic White-Light Emission from Layered Hybrid Perovskites *J. Am. Chem. Soc.* 136, 13154-13157 (2014).
29. Yuan, Z. et al. One-dimensional organic lead halide perovskites with efficient bluish white-light emission. *Nat. Commun.* 8, 14051 (2017).
30. Khan, S. et al. Time-Resolved Emission Reveals Ensemble of Emissive States as the Origin of Multicolor Fluorescence in Carbon Dots. *Nano Lett.* 15, 8300-8305 (2015).
31. Bao, L. et al. Photoluminescence-Tunable Carbon Nanodots: Surface-State Energy-Gap Tuning. *Adv. Mater.* 27, 1663-1667 (2015).
32. Pan, L. L. et al. Truly Fluorescent Excitation-Dependent Carbon Dots and Their Applications in Multicolor Cellular Imaging and Multidimensional Sensing. *Adv. Mater.* 27, 7782-7787 (2015).
33. Hu, S. L. et al. Tunable Photoluminescence Across the Entire Visible Spectrum from Carbon Dots Excited by White Light. *Angew. Chem. Int. Ed.* 54, 2970-2974 (2015).
34. Povie, G. et al. Synthesis of a carbon nanobelt. *Science* 356, 172-175 (2017).
35. Fleetham, T. et al. Phosphorescent Pt(II) and Pd(II) Complexes for Efficient, High-Color-Quality, and Stable OLEDs. *Adv. Mater.* 29, 1601861 (2017).
36. Xu, Y. Q. et al. Two-Photon-Pumped Perovskite Semiconductor Nanocrystal Lasers. *J. Am. Chem. Soc.* 138, 3761-3768 (2016).
37. George, P. A. et al. Ultrafast Optical-Pump Terahertz-Probe Spectroscopy of the Carrier Relaxation and Recombination Dynamics in Epitaxial Graphene. *Nano Lett.* 8, 4248-4251 (2008).
38. Gao, B. et al. Studies of Intrinsic Hot Phonon Dynamics in Suspended Graphene by Transient Absorption Microscopy. *Nano Lett.* 11, 3184-3189 (2011).
39. Wen, X. M. et al. Intrinsic and Extrinsic Fluorescence in Carbon Nanodots: Ultrafast Time-Resolved Fluorescence and Carrier Dynamics. *Adv. Opt. Mater.* 1, 173-178 (2013).
40. Li, Q. et al. Silicon Nanoparticles with Surface Nitrogen: 90% Quantum Yield with Narrow Luminescence Bandwidth and the Ligand Structure Based Energy Law. *ACS Nano* 10, 8385-8393 (2016).
41. Sui, L. Z. et al. Ultrafast carrier dynamics of carbon nanodots in different pH environments. *Phys. Chem. Chem. Phys.* 18.3838-3845 (2016).

42. Adam, D. W. et al. Electron-phonon coupling in hybrid lead halide perovskites. *Nat. Commun.* 7, 11755 (2016).
43. Balan, A. D. et al. Effect of Thermal Fluctuations on the Radiative Rate in Core/Shell Quantum Dots. *Nano Lett.* 17, 1629-1636 (2017).
44. Villegas, C. E. P. et al. Anomalous Temperature Dependence of the Band Gap in Black Phosphorus. *Nano Left.* 16, 5095-5101 (2016).
45. Wang, Y. et al. Blue Liquid Lasers from Solution of CdZnS/ZnS Ternary Alloy Quantum Dots with Quasi-Continuous Pumping. *Adv. Mater.* 27, 169-175 (2015).
46. Manser, J. S et al. Intriguing Optoelectronic Properties of Metal Halide Perovskites. *Chem. Rev.* 116, 12956-13008 (2016).
47. Arcudi, F. et al. Synthesis, Separation, and Characterization of Small and Highly Fluorescent Nitrogen-Doped Carbon NanoDots. *Angew. Chem. Int. Ed.* 55, 2107-2112 (2016).
48. Kim, J. K. et al. Origin of White Electroluminescence in Graphene Quantum Dots Embedded Host/Guest Polymer Light Emitting Diodes. *Sci. Rep.* 5, 11032 (2015).
49. Dai, X. L. et al. Quantum-Dot Light-Emitting Diodes for Large-Area Displays: Towards the Dawn of Commercialization. *Adv. Mater.* 29, 1607022 (2017).
50. Sun, Q. J. et al. Bright, Multicolored Light-Emitting Diodes Based on Quantum Dots. *Nat. Photonics,* 1, 717-722 (2007).
51. Qian, L. et al. Stable and efficient quantum-dot light-emitting diodes based on solution-processed multilayer structures. Nat. Photonics 5, 543-548 (2011).
52. Tan. Z. K. et al. Bright light-emitting diodes based on organometal halide perovskite. Nat. Mater. 9, 687-692 (2014).
53. Song, J. Z. et al. Quantum Dot Light-Emitting Diodes Based on Inorganic Perovskite Cesium Lead Halides (CsPbX3). Adv. Mater. 27, 7162-7167 (2015).
54. Pan, J. et al. Highly Efficient Perovskite-Quantum-Dot Light-Emitting Diodes by Surface Engineering. Adv. Mater. 28, 8718-8725 (2016).
55. Byun, J. et al. Efficient Visible Quasi-2D Perovskite Light-Emitting Diodes. Adv. Mater. 28, 7515-7520 (2016).
56. Lim, J. et al. Highly Efficient Cadmium-Free Quantum Dot Light-Emitting Diodes Enabled by the Direct Formation of Excitons within InP@ZnSeS Quantum Dots. ACS Nano 7, 9019-9026 (2013).

The invention claimed is:

1. A triangular carbon quantum dot, which comprises a conjugated triangular structure comprising at least four aromatic rings,
wherein said conjugated triangular structure comprises a side functional group and the content of carbon atoms in said triangular carbon quantum dot is 50 weight % or more.

2. The triangular carbon quantum dot of claim 1, wherein the conjugated triangular structure comprises a plurality of the 6-member aromatic core rings fused to the at least three aromatic rings.

3. The triangular carbon quantum dot of claim 1, wherein the core ring is formed by conjugation of at least three aromatic ring precursors.

4. The triangular carbon quantum dot of claim 1, wherein at least one of the three aromatic ring precursors is selected from the group consisting of benzene-1,3,5-triol (phloroglucinol), resorcinol, 5-aminobenzene- 1,3-diol, 5-(dimethylamino)benzene-1,3-diol, 5-(diethylamino)benzene- 1,3-diol, 5- (dipropylamino)benzene-1,3-diol, 5-(methylthio)benzene-1,3-diol, 5-methoxybenzene- 1,3-diol, 3,5-dihydroxyphenylboronic acid, pyridine-3,5-diol, phosphinine-3,5-diol, and borinine-3,5-diol.

5. The triangular carbon quantum dot of claim 1, which is prepared by solvothermal synthesis using at least three precursor molecules each comprising an aromatic ring.

6. The triangular carbon quantum dot of claim 5, wherein each of the precursor molecules comprises a 6-member aromatic ring.

7. The triangular carbon quantum dot of claim 6, wherein each of the precursor molecules is a compound having a structure of Formula A:

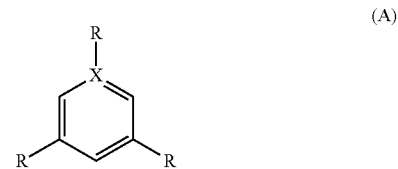

wherein X is selected from the group consisting of C, N, P, and B; and each R is independently selected from the group consisting of —OR$^a$, —NR$^b$R$^c$, —SR$^d$, —COOR$^e$, and —B(OR$^f$)(OR$^g$), wherein R$^a$, R$^b$, R$^c$, R$^d$, R$^e$, R$^f$ and R$^g$ are each independently H or C$_{1-6}$alkyl, or R is absent.

8. The triangular carbon quantum dot of claim 7, wherein each of the precursor molecules is selected from the group consisting of

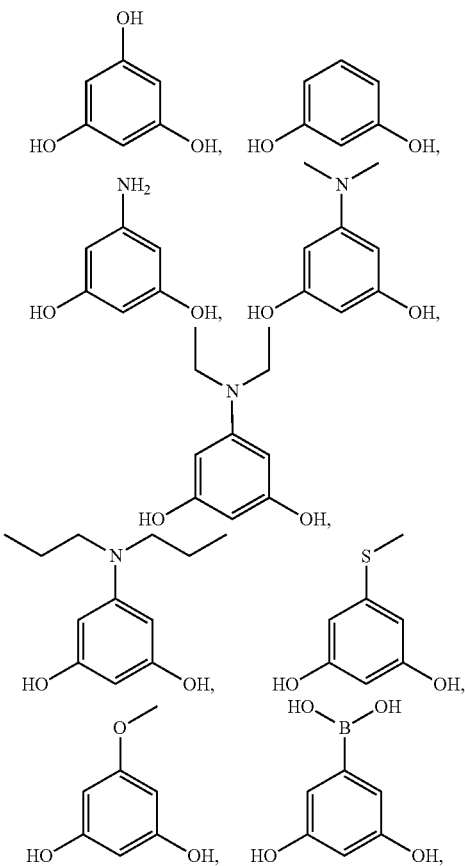

-continued

[Structures: 3,5-dihydroxypyridine; 3,5-dihydroxyphosphinine; and]

[Structure: 3,5-dihydroxyborinine]

9. The triangular carbon quantum dot of claim 8, wherein each of the precursor molecules is

[Structure: phloroglucinol / 1,3,5-trihydroxybenzene]

10. The triangular carbon quantum dot of claim 6, wherein the precursor molecules are used to form a conjugated triangular structure comprising a structure of Formula I:

(I)

[Structure of Formula I: triphenylene with R substituents]

wherein
each R is independently selected from the group consisting of —OR$^a$, —NR$^b$R$^c$, —SR$^d$, COOR$^e$, and —B(OR$^f$)(OR$^g$), wherein R$^a$, R$^b$, R$^c$, R$^d$, R$^e$, R$^f$ and R$^g$ are each independently H or C$_{1-6}$alkyl; and/or
the structure of Formula I serves as a core structure for further conjugation with the precursor molecules to form a larger conjugated triangular structure.

11. The triangular carbon quantum dot of claim 6, wherein the precursor molecules are used to form a conjugated triangular structure comprising a structure of Formula I-A:

(I-A)

[Structure of Formula I-A with R substituents]

wherein
each R is independently selected from the group consisting of —OR$^a$, —NR$^b$R$^c$, —SR$^d$, COOR$^e$, and —B(OR$^f$)(OR$^g$), wherein R$^a$, R$^b$, R$^c$, R$^d$, R$^e$, R$^f$ and R$^g$ are each independently H or C$_{1-6}$alkyl; and/or
the structure of Formula I-A serves as a core structure for further conjugation with the precursor molecules to form a larger conjugated triangular structure.

12. The triangular carbon quantum dot of claim 6, wherein the precursor molecules are used to form a conjugated triangular structure comprising a structure of Formula I-B:

(I-B)

[Structure of Formula I-B with R substituents]

wherein
each R is independently selected from the group consisting of —OR$^a$, —NR$^b$R$^c$, —SR$^d$, COOR$^e$, and —B(OR$^f$)(OR$^g$), wherein R$^a$, R$^b$, R$^c$, R$^d$, R$^e$, R$^f$ and R$^g$ are each independently H or C$_{1-6}$alkyl; and/or
the structure of Formula I-B serves as a core structure for further conjugation with the precursor molecules to form a larger conjugated triangular structure.

13. The triangular carbon quantum dot of claim 6, wherein the precursor molecules are used to form a conjugated triangular structure comprising a structure of Formula II:

(II)

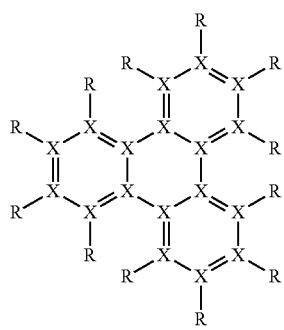

wherein each X is independently selected from the group consisting of C, N, P, and B;

each R is independently selected from the group consisting of —OR$^a$, —NR$^b$R$^c$, —SR$^d$, COOR$^e$, and —B(OR$^f$)(OR$^g$), wherein R$^a$, R$^b$, R$^c$, R$^d$, R$^e$, R$^f$ and R$^g$ are each independently H or C$_{1-6}$alkyl, or R is absent; and/or the structure of Formula II serves as a core structure for further conjugation with the precursor molecules to form a larger conjugated triangular structure.

14. The triangular carbon quantum dot of claim 6, wherein the precursor molecules are used to form a conjugated triangular structure comprising a structure of Formula II-A:

(II-A)

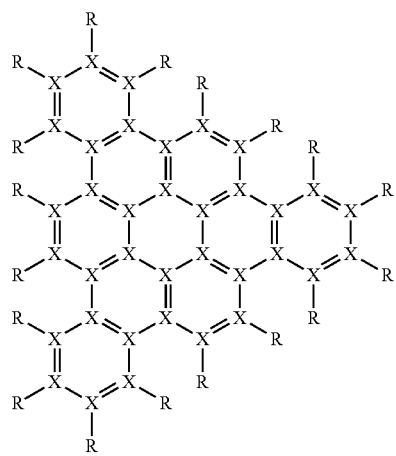

wherein each X is independently selected from the group consisting of C, N, P, and B;

each R is independently selected from the group consisting of —OR$^a$, —NR$^b$R$^c$, —SR$^d$, COOR$^e$, and —B(OR$^f$)(OR$^g$), wherein R$^a$, R$^b$, R$^c$, R$^d$, R$^e$, R$^f$ and R$^g$ are each independently H or C$_{1-6}$alkyl, or R is absent; and/or the structure of Formula II-A serves as a core structure for further conjugation with the precursor molecules to form a larger conjugated triangular structure.

15. The triangular carbon quantum dot of claim 6, wherein the precursor molecules are used to form a conjugated triangular structure comprising a structure of Formula II-B:

(II-B)

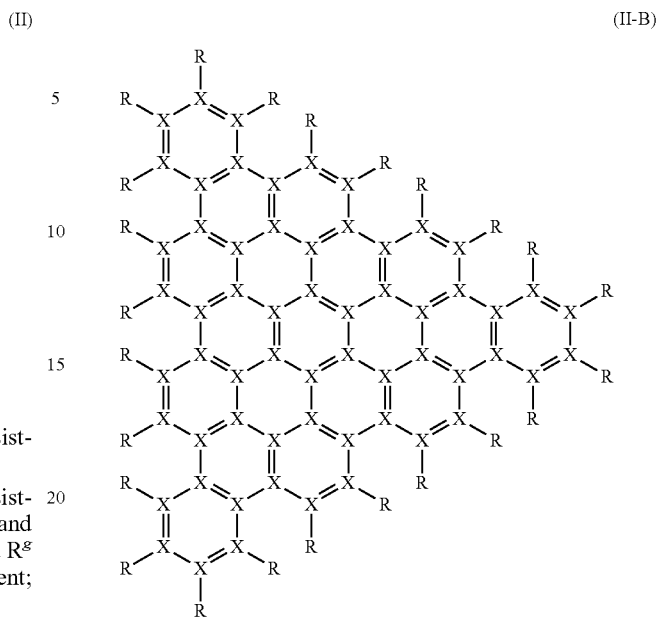

wherein each X is independently selected from the group consisting of C, N, P, and B;

each R is independently selected from the group consisting of —OR$^a$, —NR$^b$R$^c$, —SR$^d$, COOR$^e$, and —B(OR$^f$)(OR$^g$), wherein R$^a$, R$^b$, R$^c$, R$^d$, R$^e$, R$^f$ and R$^g$ are each independently H or C$_{1-6}$alkyl, or R is absent; and/or the structure of Formula II-B serves as a core structure for further conjugation with the precursor molecules to form a larger conjugated triangular structure.

16. The triangular carbon quantum dot of any of claim 1, which has an emission peak ranging from about 400 nm to about 700 nm.

17. The triangular carbon quantum dot of any of claim 1, which has a full width at half maximum (FWHM) ranging from about 20 nm to about 70 nm.

18. The triangular carbon quantum dot of any claim 1, which has a size or diameter ranging from about 1 nm to about 6 nm.

19. The triangular carbon quantum dot of claim 1, which has a quantum yield (QY) ranging from about 50% to about 75%.

20. A method for preparing a triangular carbon quantum dot, e.g., a triangular carbon quantum dot of claim 1, which method comprises solvothermal synthesis using at least three precursor molecules each comprising an aromatic ring, e.g., a 6-member aromatic ring, to form a triangular carbon quantum dot.

21. An article of manufacture, which comprises a triangular carbon quantum dot of claim 1.

22. The article of manufacture of claim 21, which is comprised in photoelectric device, a transistor, a solar cell, a light emitting device, a light-emitting diode (LED), a diode laser, a qubit in quantum computing, a display, e.g., a television or a phone, a head-up display, e.g., a transparent head-up display, or a paint, e.g., a fluorescent paint or a luminescent paint.

23. A light-emitting diode (LED), which comprises a triangular carbon quantum dot of claim 1.

24. The LED of claim 23, which comprises, from one side to an opposite side, e.g., from the bottom up, a ITO glass substrate anode, a poly(3,4-ethylenedioxythiophene):poly(styrenesulfonate) (PEDOT:PSS) hole injection layer (HIL), an active triangular carbon quantum dot:PVK blended emission layer, a 1,3,5-tris(N-phenylbenzimidazol-2-yl) benzene (TPBI) electron transport layer (ETL), and a Ca/Al double-layered cathode.

25. The LED of claim 23, which has a maximum luminance from about 500 cd/m$^2$ to about 10,000 cd/m$^2$.

26. The LED of claim 23, which has a current efficiency from about 1 cd/A to about 10 cd/A.

27. The LED of claim 23, which has a turn on voltage from about 2 V to about 5 V.

28. The LED of claim 23, which has an emission range from about 460 nm to about 610 nm.

29. A method for displaying a color, which comprises displaying a color of a triangular carbon quantum dot of claim 1.

\* \* \* \* \*